(12) United States Patent
Jana et al.

(10) Patent No.: US 9,359,367 B2
(45) Date of Patent: Jun. 7, 2016

(54) TETRAHYDROQUINAZOLINONE DERIVATIVES AS PARP INHIBITORS

(71) Applicant: Lupin Limited, Mumbai (IN)

(72) Inventors: Gourhari Jana, Pune (IN); Sanjay Pralhad Kurhade, Pune (IN); Arun Rangnath Jagdale, Pune (IN); Gagan Kukreja, Pune (IN); Neelima Sinha, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/411,968

(22) PCT Filed: Jul. 9, 2013

(86) PCT No.: PCT/IB2013/055618
§ 371 (c)(1),
(2) Date: Dec. 30, 2014

(87) PCT Pub. No.: WO2014/009872
PCT Pub. Date: Jan. 16, 2014

(65) Prior Publication Data
US 2015/0152118 A1    Jun. 4, 2015

(30) Foreign Application Priority Data

Jul. 9, 2012 (IN) .............................. 762/KOL/2012

(51) Int. Cl.
| | | |
|---|---|---|
| A01N 43/54 | (2006.01) | |
| A61K 31/517 | (2006.01) | |
| C07D 239/72 | (2006.01) | |
| C07D 487/08 | (2006.01) | |
| C07D 239/88 | (2006.01) | |
| C07D 239/90 | (2006.01) | |
| A61K 31/527 | (2006.01) | |
| A61K 45/06 | (2006.01) | |
| C07D 239/91 | (2006.01) | |
| C07D 401/12 | (2006.01) | |

(52) U.S. Cl.
CPC ............ *C07D 487/08* (2013.01); *A61K 31/517* (2013.01); *A61K 31/527* (2013.01); *A61K 45/06* (2013.01); *C07D 239/88* (2013.01); *C07D 239/90* (2013.01); *C07D 239/91* (2013.01); *C07D 401/12* (2013.01)

(58) Field of Classification Search
None
See application file for complete search history.

(56) References Cited

U.S. PATENT DOCUMENTS

| | | |
|---|---|---|
| 3,984,555 A | 10/1976 | Amschler et al. |
| 4,108,982 A | 8/1978 | Amschler |
| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 5,021,420 A | 6/1991 | Comte et al. |
| 5,675,005 A | 10/1997 | Küfner-Mühl et al. |
| 8,143,241 B2 | 3/2012 | Ashworth et al. |
| 8,859,562 B2 | 10/2014 | Helleday |
| 2002/0068748 A1 | 6/2002 | Fliri et al. |
| 2005/0065178 A1 | 3/2005 | Basha et al. |
| 2005/0222166 A1 | 10/2005 | Elmaleh et al. |
| 2005/0245534 A1 | 11/2005 | Link et al. |
| 2007/0015792 A1 | 1/2007 | Hashimoto et al. |
| 2007/0197551 A1 | 8/2007 | Sato et al. |
| 2008/0076758 A1 | 3/2008 | Folkes et al. |
| 2008/0076760 A1 | 3/2008 | Ohtake |
| 2008/0161564 A1 | 7/2008 | Schwindt et al. |
| 2008/0176926 A1 | 7/2008 | Bolli et al. |
| 2009/0163545 A1 | 6/2009 | Goldfarb |
| 2009/0226412 A1 | 9/2009 | Yasuhiro et al. |
| 2010/0144745 A1 | 6/2010 | Bamberg et al. |

(Continued)

FOREIGN PATENT DOCUMENTS

| | | |
|---|---|---|
| DE | 2638184 A1 | 3/1977 |
| DE | 4312832 C1 | 10/1994 |

(Continued)

OTHER PUBLICATIONS http://en.wikipedia.org/wiki/Leukemia, last accessed Oct. 5, 2015.*
International Search Report in corresponding International Patent Application No. PCT/IB2013/055618, mailed Aug. 26, 2013.
Abou-Seri, Sahar Mahmoud, et al., "Molecular modeling study and synthesis of quinazolinone-arylpiperazine derivatives $\alpha_1$-adrenoreceptor antagonists," *European Journal of Medicinal Chemistry*, vol. 46, No. 2, pp. 647-658 (2011).

(Continued)

*Primary Examiner* — Jeffrey H Murray
(74) *Attorney, Agent, or Firm* — Leydig, Voit & Mayer, Ltd.

(57) ABSTRACT

Disclosed are compounds of formula (I), their tautomeric forms, stereoisomers, and pharmaceutically acceptable salts thereof, wherein $R^1$-$R^6$, $R^{7a-d}$, $R^{8a-d}$, A, M, n, and p are as defined in the specification, pharmaceutical compositions including a compound, tautomer, stereoisomer, or salt thereof, and methods of treating or preventing diseases or disorders, for example, cancer, that are amenable to treatment or prevention by inhibiting the PARP enzyme of a subject.

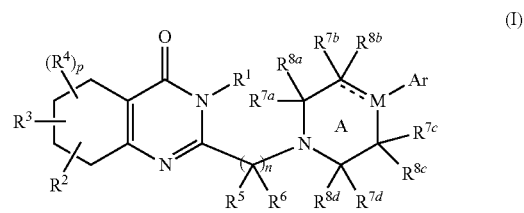

(I)

19 Claims, No Drawings

(56) References Cited

U.S. PATENT DOCUMENTS

| | | |
|---|---|---|
| 2010/0226943 A1 | 9/2010 | Brennan et al. |
| 2011/0237553 A1 | 9/2011 | Ding et al. |
| 2012/0157306 A1 | 6/2012 | Frackenpohl et al. |

FOREIGN PATENT DOCUMENTS

| | | |
|---|---|---|
| EP | 1396488 A1 | 3/2004 |
| EP | 2208728 A1 | 7/2010 |
| JP | 2005504737 A1 | 2/2005 |
| WO | WO 95/16682 | 6/1995 |
| WO | WO 00/50417 | 8/2000 |
| WO | WO 01/70737 A | 9/2001 |
| WO | WO 02/48117 A1 | 6/2002 |
| WO | WO 03/006423 A1 | 1/2003 |
| WO | WO 03/055865 A1 | 7/2003 |
| WO | WO 03/063874 A1 | 8/2003 |
| WO | WO 2004/018058 A2 | 3/2004 |
| WO | WO 2005/016900 A1 | 2/2005 |
| WO | WO 2005/082887 A1 | 9/2005 |
| WO | WO 2005/105760 A1 | 11/2005 |
| WO | WO 2006/003150 A1 | 1/2006 |
| WO | WO 2006/039545 A2 | 4/2006 |
| WO | WO 2006/051851 A1 | 5/2006 |
| WO | WO 2006/064251 A1 | 6/2006 |
| WO | WO 2006/137510 A1 | 12/2006 |
| WO | WO 2007/011623 A1 | 1/2007 |
| WO | WO 2007/062413 A2 | 5/2007 |
| WO | WO 2007/071055 A2 | 6/2007 |
| WO | WO 2007/076055 A2 | 7/2007 |
| WO | WO 2007/110868 A2 | 10/2007 |
| WO | WO 2009/041565 A1 | 4/2009 |
| WO | WO 2009/041566 A1 | 4/2009 |
| WO | WO 2009/090556 A2 | 7/2009 |
| WO | WO 2009/114459 A2 | 9/2009 |
| WO | WO 2010/082813 A1 | 7/2010 |
| WO | WO 2010/082821 A1 | 7/2010 |
| WO | WO 2012/028578 A1 | 3/2012 |

OTHER PUBLICATIONS

Asagarasu, Akira, et al., "Discovery of a Novel 5-HT$_3$ Antagonist/5-HT$_{1A}$ Agonist 3-Amino-5,6,7,8-tetrahydro-2-{4-[4-(quinolin-2-yl)piperazin-1-yl]butyl}quinazolin-4(3H)-one (TZB-30878) as an Orally Bioavailable Agent for Irritable Bowel Syndrome," *Journal of Medicinal Chemistry*, vol. 53, No. 21, pp. 7549-7563 (2010).

Avis, Kenneth E., "Parenteral Preparations," *Remington's Pharmaceutical Sciences*, 17th Edition, Chapter 85, Mack Publishing Company, Easton, PA, pp. 1518-1541 (1985).

Bavetsias, V., et al., "The Design and Synthesis of Water-Soluble Analogues of CB30865, a Quinazolin-4-one-Based Antitumor Agent," *Journal of Medicinal Chemistry*, vol. 45, No. 17, pp. 3692-3702 (2002).

Bellocchi, Daniele, et al., "Docking studies on PARP-1 inhibitors: insights into the role of a binding pocket water molecule," *Bioorganic & Medicinal Chemistry*, vol. 13, No. 4, pp. 1151-1157 (2005).

Berge, Stephen M., et al., "Pharmaceutical Salts," Review Article from *Journal of Pharmaceutical Sciences*, vol. 66, No. 1, pp. 1-19 (Jan. 1977).

Chang, Chih-Shiang, et al., "Design, Synthesis, and Antipicornavirus Activity of 1-[5-(4-Arylphenoxy)alkyl]-3-pyridin-4-ylimidazolidin-2-one Derivatives," *Journal of Medicinal Chemistry*, vol. 48, pp. 3522-3535 (2005).

Chiba, Jun et al. "Synthesis, biological evaluation and pharmacokinetic study of prolyl-1-piperazinylacetic acid and prolyl-4-piperidinylacetic acid derivatives as VLA-4 antagonist," *Bioorganic & Medicinal Chemistry*, vol 14, pp. 2725-2746 (2006).

D'Amours, Damien, et al., "Poly(ADP-ribosyl)ation reactions in the regulation of nuclear functions," *Biochemical Journal*, vol. 342, pp. 249-268 (1999).

Deluca, Patrick P., ed al. Parenteral Drug-Delivery Systems, *Pharmaceutics and Pharmacy Practice*, Chapter 8, J.B. Lippincott Company, Philadelphia, PA, pp. 238-250 (1982).

Eissa, Amal Abdel Haleem Mohamed, et al., "Design, Synthesis and Anti-inflammatory activity of structurally simple anthranilic acid congeners devoid of ulcerogenic side effects," *Chemical and Pharmaceutical Bulletin*, p. 1-29 (Aug. 2, 2012).

Gabrielsen, Mari, et al. "Molecular mechanism of serotonin transporter inhibition elucidated by a new flexible protocol," *European Journal of Medicinal Chemistry*, vol. 47, pp. 24-37 (2012).

Geng, Feng, et al., "Three-Component Coupling via the Squarate Ester Cascade as a Concise Route to the Bioactive Triquinane Sesquiterpene Hypnophilin," *Organic Letters*, vol. 4, No. 1, pp. 71-73 (2002).

Greene, Theodora W., et al., *Protective Groups in Organic Synthesis*, Third Edition, Wiley Interscience, pp. 1-779 (1999).

Gupta, C.M., et al., "A Novel Class of Hypoglycaemic Agents: Syntheses & SAR in 2-Substituted 4(3H)-Quinazolones, 2-Substituted 4-Hydroxypolymethylene[5,6]pyrimidines & 3-Substituted 4-Oxopyrido[1,2-a]pyrimidines," *Indian Journal of Chemistry*, vol. 9, No. 3, pp. 201-206 (Mar. 1971).

Gupta, C.M., et al., "Drugs Acting on the Central Nervous System. Synthesis of Substituted Quinazolones and Quinazolines and Triazepino- and Triazocinoquinazolones," *Journal of Medicinal Chemistry*, vol. 11, No. 2, pp. 392-395 (1968).

Hattori, Kouji, et al., "Rational design of conformationally restricted quinazolinone inhibitors of poly(ADP-ribose)poymerase," *Bioorganic & Medicinal Chemistry Letters*, vol. 17, No. 20, pp. 5577-5581 (2007).

Hattori, Kouji, et al., "Rational Approaches to Discovery of Orally Active and Brain-Penetrable Quinazolinone Inhibitors of Poly(ADP-ribose)polymerase," *Journal of Medicinal Chemistry*, vol. 47, No. 17, pp. 4151-4154 (2004).

Hayaishi, Osamu, et al., "Poly(ADP-Ribose) and ADP-Ribosylation of Proteins," , *Annual Review of Biochemistry*, vol. 46, pp. 95-116 (1977).

Ishida, Junya, et al., "Discovery of potent and selective PARP-1 and PARP-2 inhibitors: SBDD analysis via a combination of X-ray structural study and homology modeling," *Bioorganic & Medicinal Chemistry*, vol. 14, No. 5, pp. 1378-1390 (2006).

Ishida, Junya, et al., "4-Phenyl-1,2,3,6-tetrahydropyridine, an excellent fragment to improve the potency of PARP-1 inhibitors," *Bioorganic & Medicinal Chemistry Letters*, vol. 15, No. 19, pp. 4221-4225 (2005).

Iwashita, Akinori, et al., "Discovery of quinazolinone and quinoxaline derivatives as potent and selective poly(ADP-ribose) polymerase-1/2 inhibitors," *FEBS Letters*, vol, 579, No. 6, pp. 1389-1393 (2005).

Iwashita, Akinori, et al., "Neuroprotective Effects of a Novel Poly(ADP-Ribose) Polymerase-1 Inhibitor, 2-{3-4[4-(4-Chlorophenyl)-1-piperazinyl] propyl}-4(3H)- quinazolinone (FR255595), in an in Vitro Model of Cell Death and in Mouse 1-Methyl-4-phenyl-1,2,3,6-tetrahydropyridine Model of Parkinson's Disease," *The Journal of Pharmacology and Experimental Therapeutics*, vol. 309, No. 3, pp. 1067-1078 (2004).

Iwashita, Akinori, et al., "A Novel and Potent Poly(ADP-Ribose) Polymerase-1 Inhibitor, FR247304 (5-Chloro-2-[3-(4-phenyl-3,6-dihydro-1(2H)-pyridinyl)propyl]-4(3H)-quinazolinone), Attenuates Neuronal Damage in in Vitro and in Vivo Models of Cerebral Ischemia," *The Journal of Pharmacology and Experimental Therapeutics*, vol. 310, No. 2, pp. 425-436 (2004).

Jain, Sanjay, et al., "Lactam & Amide Acetals XXI. Use of Pyroglutamic Acid and Proline in Chiral Synthesis of Conformationally Constrained Piperazinones," *Tetrahedron*, vol. 48, No. 23, pp. 4985-4998 (1992).

Kinoshta, Takayoshi, et al., "Inhibitor-induced structural change of the active site of human poly (ADP-ribose) polymerase," *FEBS Letters*, vol. 556, pp. 43-46 (2004).

Kohl, Hans, et al., "Cyclisierungsreaktionen von o-Acylaminobenzhydroxamsäure-O-alkylestern," *Justus Liebigs Annalen der Chemie*, vol. 766, pp. 106-115 (1972).

Kozhevnikov, et al., "Synthesis in the 2-aminoethyl-3-(2'-tolyl)-4-quinazolone," *Khimiko-Farmatsevticheskii Zhurnal*, vol. 4, No. 11, pp. 22-25 (1970).

(56) References Cited

OTHER PUBLICATIONS

Last, Larry A., et al., "Synthesis of Polycyclic Homocyclopropylcarbinols by Reductive Cyclization of Bromocyclopropyl Epoxides," *The Journal of Organic Chemistry*, vol. 47, pp. 3211-3219 (1982).
Minato, Kouichi, et al., "Biotransformation of 3-Amino-5,6,7,8-tetrahydro-2-{4-[4-(quinolin-2-yl)piperazin-1-yl]butyl}quinazolin-4(3H)-one (TZB-30878), a Novel 5-Hydroxytryptamine (5-HT)$_{1A}$ Agonist/5-HT$_3$ Antagonist, in Human Hepatic Cytochrome P450 Enzymes," *Drug Metabolism and Disposition*, vol. 36, No. 5, pp. 831-840 (2008).
Moss, Robert A., et al., "Conversion of 'Obstinate' Nitrites to Amidines by Garigipati's Reaction," *Tetrahedron Letters*, vol. 36, No. 48, pp. 8761-8764 (1995).
Ohno, Kazuki, et al., "Docking study and binding free energy calculation of poly (ADP-ribose) polymerase inhibitors," *Journal of Molecular Modeling*, vol. 17, No. 2, pp. 383-389 (2011).
Pellicciari, Roberto, et al., "On the Way to Selective PARP-2 Inhibitors. Design, Synthesis, and Preliminary Evaluation of a Series of Isoquinolinone Derivatives," *ChemMedChem*, vol. 3, No. 6, pp. 914-923 (2008).
"Product Identification Guide," *Physicians' Desk Reference*, 58th Edition, Thomson PDR, Montvale, NJ, pp. 303-340 (2004).
"Product Information—Eisai,"*Physicians' Desk Reference*, 58th Edition, Thomson PDR, Montval, NJ, pp. 1221-1223 (2004).
"Product information—Janssen," *Physicians' Desk Reference*, 58th Edition, Thomson PDR, Montvale, NJ, pp. 1759-1769 (2004).
"Product Information—Novartis Pharmaceuticals," *Physicians' Desk Reference*, 58th Edition, Thomson PDR, Montvale, NJ, pp. 2252-2259 (2004).
"Product Information—Pfizer,"*Physicians' Desk Reference*, 58th Edition, Thomson PDR, Montvale, NJ. pp. 2570-2573 (2004).
Remington's Pharmaceutical Sciences, 18th Edition, p. 1445 (1990).
Sandhu, Shahneen K., et al., "Poly(ADP-ribose) polymerase inhibitors in cancer treatment: A clinical perspective," *European Journal of Cancer*, vol. 46, pp. 9-20 (2010).
Sathi, Garima et al., "CNS Activity of Some Newer Quinazolone Derivatives," *Indian Drugs*, vol. 18, No. 3, pp. 90-93 (Dec. 1980).
Saxena, Sushma, et al., "New Quinazolone Congeners," *Journal of the Indian Chemical Society*, vol. 68, No. 3, pp. 142-143 (Mar. 1991).
Shelat, C.D., et al., "Synthesis, Characterization, Chelatino Properties and Anti-Fungal Activity of 2-(4-Phenylpiperazinyi) Methyl-3-(8-Quinolinol-5-Yl)-4(3h)-Quinazolinone," *E-Journal of Chemistry*, vol. 2, No. 1, pp. 86-90 (Jan. 2005).
Singh, Inder Pal, et al., "Synthesis of Antiinflammatory Activity of 2-Substituted-phenethyl-3-substituted-phenyl-4(3H)-quinazolinones," *Indian Journal of Chemistry, Section B: Organic Chemistry Including Medicinal Chemistry*, vol. 23B, No. 6, pp. 592-594 (Jun. 1984).
Stahl, P. Heinrich, et al., *Handbook of Pharmaceutical Salts: Properties, Selection, and Use*, Wiley-VCH, Weinheim, pp. 1-374 (2002).
Szoka, Jr., Francis, et al., "Comparative Properties and Methods of Preparation of Lipid Vesicles (Liposomes)," *Annual Review of Biophysics & Bioengineering*, vol. 9, pp. 467-508 (1980).
Tamaoki, Satoru, et al., "Pharmacological Properties of 3-Amino-5,6,7,8-tetrahydro-2-{4-[-(quinolin-2-yl)piperazin-1-yl]butyl}quinazolin-4(3H)-one (TZB-30878), a Novel Therapeutic Agent for Diarrhea-Predominant Irritable Bowel Syndrome (IBS) and Its Effects on an Experimental IBS Model," *The Journal of Pharmacology and Experimental Therapeutics*, vol. 322, No. 3, pp. 1315-1323 (2007).
Tani, Junichi, et al., "Studies on biologically Active Halogenated Compounds. II. [1]) Chemical Modifications of 6-Amino-2-fluoromethyl-3-(o-tolyl)-4(3H)-quinazolinone and the CNS Depressant Activities of Related Compounds," *Chemical & Pharmaceutical Bulletin*, vol. 27, No. 11, pp. 2675-2687 (1979).
Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).
Tusco, Salvatore J., et al., "Intravenous Admixtures," *Remington's Pharmaceutical Sciences*, 17th Edition, Chapter 86, Mack Publishing Company, Easton, PA, pp. 1542-1552 (1985).
Vashi, R.T., et al., "Synthesis, Characterization and Antifungal Activity Studies on Quinazoline-4-one Derivatives Containing 8-Hydroxy Quinazoline Ligand and its Metal Chelates," *Asian Journal of Chemistry*, vol. 22, No. 10, pp. 7693-7698 (2010).
Vashi, R.T., et al., "Synthesis, Spectroscopic Studies and Antifungal Activity of 2-[(4(3-Chlorophenyl)piperazine-1-yl)methyl]-3-[8-hydroxoy quinolin-5-yl]-3(H)-quinazolin-4-one Ligand and its Chelates," *E-Journal of Chemistry*, vol. 1, supplement 1, pp. S163-S168 (2010).
Vashi, R.T., et al., "Synthesis and Antifungal Activity of 6-bromo-2[(4-phenyl)-1-yl)methyl]-3-[8-hydroxy quinoline-5-yl]-3-quinazolin-4-one Ligand and its Metal Chelates," *international Journal of Current Pharmaceutical Research*, vol. 2, No. 3, pp. 57-60 (2010).
Vashi, R.T., et al., "Synthesis and antifungal activity of quinazoline-4-one derivatives containing 8-hydroxy quinazoline ligand and its transition metal chelates,"*Der Pharma Chemica*, vol. 2, No. 2, pp. 216-222 (2010).
Vashi, R.T., et al., "Synthesis and antifungal activity of 6-bromo-2[(4-pyridinyl)-1-yl) methyl]-3-[8-hydroxy quinolin-5-yl]-3-quinazolin-4-one ligand and its metal chelates," *Research Journal of Pharmaceutical, Biological and Chemical Sciences*, vol. 2, No. 2, pp. 85-92 (2011).
Verma, M., et al., "A New Potent Anti-Inflammatory Quinazolone," *Pharmacological Research Communications*, vol. 13, No. 10, pp. 967-979 (1981).
Wang, Dan, et al., "Support Vector Machine and KStar Models Predict the o-Dealkylation Reaction Mediated by Cytochrome P450," *Acta Physico-Chimica Sinica (Wili Huaxue Xuebao)*, vol. 27, No. 2, pp. 343-351 (2011).
Wasserman, Todd H., at al, "Clinical Comparison of the Nitrosoureas," *Cancer*, vol. 36, pp. 1258-1268 (1975).
Whalen, Michael J., et al., "Reduction of Cognitive and Motor Deficits After Traumatic Brain Injury in Mice Deficient in Poly(ADP-Ribose) Polymerase," *Journal of Cerebral Blood Flow and Metabolism*, vol. 19, pp. 835-842 (1999).
Zhang, Wen-Ting, et al., "Design, Synthesis, and Cytoprotective Effect of 2-Aminothiazole Analogues as Potent Poly(ADP-Ribose) Polymerase-1 Inhibitors," *Journal of Medicinal Chemistry*, vol. 52, No. 3, pp. 718-725 (2009).

* cited by examiner

TETRAHYDROQUINAZOLINONE DERIVATIVES AS PARP INHIBITORS

FIELD OF THE INVENTION

The present invention relates to tetrahydroquinazolinone derivatives, their tautomeric forms, their stereoisomers, their pharmaceutically acceptable salts, combinations with suitable medicament, pharmaceutical compositions containing them, methods of making of tetrahydroquinazolinone derivatives, and their use as PARP inhibitors.

CROSS-REFERENCE TO RELATED APPLICATIONS

The present application is the U.S. National Phase of International Patent Application No. PCT/IB2013/055618, filed Jul. 9, 2013, which claims the benefit of Indian Provisional Patent Application No. 0762/KOL/2012, filed Jul. 9, 2012, the disclosures of which are incorporated herein by reference in their entireties.

BACKGROUND OF THE INVENTION

Poly (ADP-ribose) Polymerase (PARP; 113 kDa) is an enzyme that catalyzes the addition of ADP-ribose residues to various target proteins. The reaction requires $NAD^+$ as substrate. As many as 18 isoforms of PARP are known. PARP1 and PARP2 are the closest relatives [60% identical in PARP1 is activated by SSB (single-strand breaks) in DNA]. ADP-ribosylation occurs at the carboxylate groups of glutamic acid or aspartic acid residues in acceptor proteins and results in the modulation of catalytic activity and protein-protein interactions of the target proteins (e.g., modulation of chromatin structure, DNA synthesis, DNA repair (Base Excision Repair or BER), transcription, and/or cell cycle progression. PARP binds to DNA single strand as well as double strand breaks. The binding of PARP to damaged DNA leads to activation of the enzyme. PARP carries out ADP ribosylation of proteins involved in DNA repair (e.g., BER) including itself. Automodification of PARP results in its release from DNA which allows the DNA repair machinery to access the DNA damage site and carry out the repair process.

Overactivation of PARP leads to necrotic cell death as a result of $NAD^+$ and ATP depletion.

Cancer patients who have undergone radiotherapy or have been treated with chemotherapeutic agents that damage DNA (e.g. cisplatin, irinotecan, temozolomide) harbour DNA strand breaks. Activation of PARP in such cases allows the repair of the damaged DNA, thus leading to an undesirable resistance to the chemotherapeutic agents (and the consequent inefficacy). In such a scenario, treatment with a PARP inhibitor is expected to make the repair process inefficient and cause cell death.

BRCA1 and BRCA2 play an important role in HR (Homologous Recombination). DNA breaks arising during DNA replication can only be repaired by HR.

Continuous exposure of BRCA1/BRCA2 deficient cells to PARP inhibitor results in accumulation of DNA DSB followed by apoptosis (Synthetic Lethality). Triple Negative Breast Cancers (TNBC) are also acutely sensitive to PARP since they also harbor defects in the DNA repair machinery. Recently, cancer cells deficient in USP11 and endometrial cancer cells deficient in PTEN have also been shown to be sensitive to PARP inhibitors. PARP inhibitors thus have immense potential to be used for anticancer chemotherapy. [Biochem. J., (1999) 342, 249-268; Ann. Rev. Biochem., 1977, 46:95-116; E. Journal Cancer 4 6 (2010) 9-20]. Additionally, PARP has been implicated in a number of disease conditions other than cancer. These include disorders such as stroke, traumatic brain injury, Parkinson's disease, meningitis, myocardial infarction, ischaemic cardiomyopathy and other vasculature-related disorders. In animal experiments, PARP−/−mice demonstrated improved motor and memory function after CCI (Controlled Cortical Impact) versus PARP+/+ mice (J Cereb Blood Flow Metab. 1999, Vol. 19. No. 8, 835).

While attempts have been made to develop PARP inhibitors for treating cancer and other diseases, satisfactory treatment has not been achieved. Therefore, there exists an unmet need for new PARP inhibitors and treatment regimen therewith.

BRIEF SUMMARY OF THE INVENTION

In one aspect, the present invention provides a compound of formula (I), its tautomeric form, its stereoisomer, its pharmaceutically acceptable salt, its combination with suitable medicament, its pharmaceutical composition and its use as PARP inhibitor,

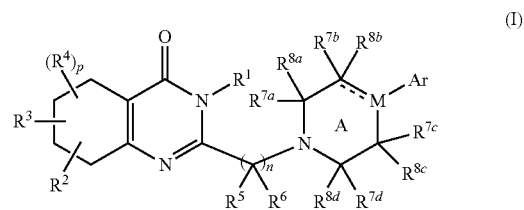

(I)

wherein,

M is selected from C, CH, and N;

------ is a single bond when M is selected as N, and ------ is either a single or a double bond when M is selected as CH or C respectively;

$R^1$ is selected from hydrogen, and substituted- or unsubstituted-alkyl;

$R^2$ and $R^3$ groups are attached either to the same carbon atom or adjacent or non-adjacent carbon atoms of the carbocylic ring, and $R^2$ and $R^3$ together with the carbon atom(s) to which they are attached form a substituted- or unsubstituted carbocycle;

$R^4$ is selected independently at each occurrence from halogen, cyano, substituted- or unsubstituted-alkyl, $-OR^9$, and $-N(R^{10})R^{11}$;

$R^5$ and $R^6$ are each independently selected from hydrogen, halogen, substituted- or unsubstituted-alkyl, perhaloalkyl, substituted- or unsubstituted-cycloalkyl, $-OR^9$, and $-N(R^{10})R^{11}$, or $R^5$ and $R^6$ together constitute oxo (=O), or both $R^5$ and $R^6$ attached to the same carbon atom or adjacent or non-adjacent carbon atoms together with the carbon atom(s) to which they are attached form a substituted- or unsubstituted-carbocycle, or when they are attached to adjacent carbon atoms, form a pi bond linking the said carbon atoms.

$R^{7a}$, $R^{8a}$, $R^{7b}$, $R^{8b}$, $R^{7c}$, $R^{8c}$, $R^{7d}$, and $R^{8d}$ are each independently selected from hydrogen, halogen, substituted- or unsubstituted-alkyl, $-OR^9$, and $-N(R^{10})R^{11}$;

or any two groups out of $R^{7a}$, $R^{8a}$, $R^{7b}$, $R^{8b}$, $R^{7c}$, $R^{8c}$, $R^{7d}$, and $R^{8d}$ form oxo (=O), or any two groups out of $R^{7a}$, $R^{8a}$, $R^{7b}$, $R^{8b}$, $R^{7c}$, $R^{8c}$, $R^{7d}$, and $R^{8d}$ taken together with the carbon atom(s) to which they are attached form a substituted- or unsubstituted-carbocycle, or a substituted- or unsubstituted heterocycle, thereby making ring 'A' either a spiro-bicycle or a fused-bicycle or a bridged-bicycle;

Ar is selected from substituted- or unsubstituted-aryl and substituted- or unsubstituted heteroaryl;

p is an integer selected from 0, 1, 2 and 3;

n is an integer selected from 1, 2, 3, and 4;

$R^9$ is selected from hydrogen and substituted- or unsubstituted-alkyl;

$R^{10}$ and $R^{11}$ are each independently selected from hydrogen and substituted- or unsubstituted-alkyl;

In second aspect the invention provides a pharmaceutical composition comprising the compound of formula (I) and a pharmaceutically acceptable carrier.

In third aspect the invention provides a method of treating or preventing a disorder responsive to the inhibition of PARP activity in a mammal suffering therefrom, comprising administering to the mammal in need of such treatment a therapeutically effective amount of a compound of formula (I).

DETAILED DESCRIPTION OF THE INVENTION

The present invention relates to novel compound of the general formula (I), its tautomeric form, its stereoisomer, its pharmaceutically acceptable salt, its combination with suitable medicament, its pharmaceutical composition, process and intermediates for the preparation of the above said compound having PARP inhibitory activity,

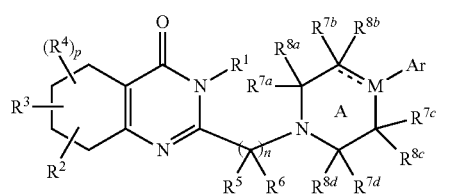

(I)

wherein,

M is selected from C, CH, and N;

▬▬▬ is a single bond when M is selected as N, and

▬▬▬ is either a single or a double bond when M is selected as CH or C respectively;

$R^1$ is selected from hydrogen, and substituted- or unsubstituted-alkyl;

$R^2$ and $R^3$ groups are attached either to the same carbon atom or adjacent or non-adjacent carbon atoms of the carbocyclic ring, and $R^2$ and $R^3$ together with the carbon atom(s) to which they are attached form a substituted- or unsubstituted carbocycle;

$R^4$ is selected independently at each occurrence from halogen, cyano, substituted- or unsubstituted-alkyl, —$OR^9$, and —$N(R^{10})R^{11}$;

$R^5$ and $R^6$ are each independently selected from hydrogen, halogen, substituted- or unsubstituted-alkyl, perhaloalkyl, substituted- or unsubstituted-cycloalkyl, —$OR^9$, and —$N(R^{10})R^{11}$, or $R^5$ and $R^6$ together constitute oxo (=O), or both $R^5$ and $R^6$ attached to the same carbon atom or adjacent or non-adjacent carbon atoms together with the carbon atom(s) to which they are attached form a substituted- or unsubstituted-carbocycle, or when they are attached to adjacent carbon atoms, form a pi bond linking the said carbon atoms.

$R^{7a}$, $R^{8a}$, $R^{7b}$, $R^{8b}$, $R^{7c}$, $R^{8c}$, $R^{7d}$, and $R^{8d}$ are each independently selected from hydrogen, halogen, substituted- or unsubstituted-alkyl, —$OR^9$, and —$N(R^{10})R^{11}$;

or any two groups out of $R^{7a}$, $R^{8a}$, $R^{7b}$, $R^{8b}$, $R^{7c}$, $R^{8c}$, $R^{7d}$, and $R^{8d}$ form oxo (=O), or any two groups out of $R^{7a}$, $R^{8a}$, $R^{7b}$, $R^{8b}$, $R^{7c}$, $R^{8c}$, $R^{7d}$, and $R^{8d}$ taken together with the carbon atom(s) to which they are attached form a substituted- or unsubstituted-carbocycle, or a substituted- or unsubstituted heterocycle, thereby making ring 'A' either a spiro-bicycle or a fused-bicycle or a bridged-bicycle;

Ar is selected from substituted- or unsubstituted-aryl and substituted- or unsubstituted heteroaryl;

p is an integer selected from 0, 1, 2 and 3;

n is an integer selected from 1, 2, 3, and 4;

$R^9$ is selected from hydrogen and substituted- or unsubstituted-alkyl;

$R^{10}$ and $R^{11}$ are each independently selected from hydrogen and substituted- or unsubstituted-alkyl;

when an alkyl group or alkenyl group is substituted, each of them is substituted with 1 to 4 substituents independently selected from oxo (=O), halogen, cyano, perhaloalkyl, cycloalkyl, cycloalkenyl, aryl, heteroaryl, heterocyclyl, —$OR^{12a}$, —$SO_2$(alkyl), —C(=O)O(alkyl), —C(=O)N(H)$R^{12}$, —C(=O)N(alkyl)$_2$, —N(H)C(=O)(alkyl), —N(H)$R^{12}$, and —N(alkyl)$R^{12}$;

when 'cycloalkyl', 'cycloalkenyl' and 'carbocycle' is substituted, the cycloalkyl, cycloalkenyl, or carbocycle group is substituted with 1 to 4 substituents independently selected from oxo (=O), halogen, cyano, alkyl, alkenyl, perhaloalkyl, —$OR^{12}$, —$SO_2$(alkyl), —C(=O)O(alkyl), —C(=O)N(H)$R^{12}$, —C(=O)N(alkyl)$R^{12}$, —N(H)C(=O)(alkyl), —N(H)$R^{12}$, —N(alkyl)$_2$;

when the aryl group is substituted, it is substituted with 1 to 4 substituents independently selected from halogen, nitro, cyano, hydroxy, alkyl, alkenyl, perhaloalkyl, cycloalkyl, cycloalkenyl, heterocyclyl, aryl, heteroaryl, —O-alkyl, —O— perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)N(H)cycloalkyl, —C(=O)NH$_2$, —SO$_2$N(alkyl)alkyl, —SO$_2$N(H)alkyl, —SO$_2$NH$_2$, —C(=O)OH, —C(=O)O-alkyl, —O(C=O)N(alkyl)H, —O(C=O)N(alkyl)$_2$, —O(C=O)N(cycloalkyl)H, —N(H)C(=O)N(aryl)H, —N(H)C(=O)N(alkyl)H, and —N(H)C(=O)NH$_2$;

when the heteroaryl group is substituted, it is substituted with 1 to 4 substituents independently selected from halogen, nitro, cyano, hydroxy, alkyl, alkenyl, perhaloalkyl, cycloalkyl, cycloalkenyl, heterocyclyl, aryl, heteroaryl, —O— alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)N(H)cycloalkyl, —C(=O)NH$_2$, —SO$_2$N(alkyl)alkyl, —SO$_2$N(H)alkyl, —SO$_2$NH$_2$, —C(=O)OH, —C(=O)O-alkyl, —O(C=O)N(alkyl)H, —O(C=O)N(alkyl)$_2$, —O(C=O)N(cycloalkyl)H, —N(H)C(=O)N(aryl)H, —N(H)C(=O)N(alkyl)H, and —N(H)C(=O)NH$_2$;

when the heterocyclic group is substituted, it is substituted either on a ring carbon atom or on a ring hetero atom, and when it is substituted on a ring carbon atom, it is substituted with 1 to 4 substituents independently selected from oxo (=O), halogen, cyano, alkyl, alkenyl, perhaloalkyl, —$OR^{12}$, —$SO_2$(alkyl), —C(=O)O(alkyl), —C(=O)N(H)$R^{12}$, —C(=O)N(alkyl)$R^{12}$, —N(H)C(=O)(alkyl), —N(H)$R^{12}$, N(alkyl)$_2$; and when the heterocyclic group is substituted on a ring nitrogen, it is substituted with substituents independently selected from alkyl, alkenyl, cycloalkyl, cycloalkenyl, aryl, heteroaryl, —SO₂(alkyl), —C(=O)(alkyl), C(=O)O(alkyl), —C(=O)N(H)R¹², and —C(=O)N(alkyl)R¹²;

R¹² is selected from hydrogen and alkyl; and
R¹²ᵃ is selected from hydrogen, alkyl, alkenyl, perhaloalkyl.
'n' is particularly selected as 3.
R⁵ and R⁶ are each independently selected from hydrogen and methyl; or R⁵, R⁶ and the carbon atom(s) to which they are attached together forming a carbocycle, which may be substituted with 1 to 3 alkyl groups.
R⁵, R⁶ and the carbon atoms to which they are attached together form a substituted- or unsubstituted carbocycle, wherein the said carbocycle is particularly selected from

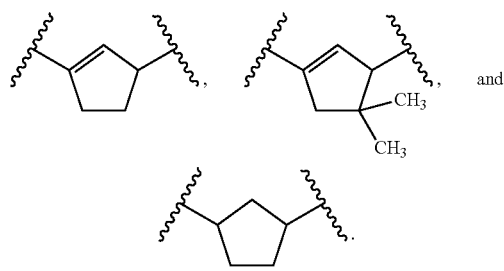

Ar is particularly selected from substituted- or unsubstituted-phenyl, substituted- or unsubstituted-pyridinyl, substituted- or unsubstituted-thiazolyl, substituted- or unsubstituted-thiophenyl, and substituted- or unsubstituted-benzothiazolyl, wherein the substituted-phenyl, substituted-pyridinyl, substituted-thiazolyl, or substituted-benzothiazolyl group is substituted with 1-3 substituents independently selected from halo, cyano, thiophenyl, phenyl, methyl, ethyl, trifluoromethyl, methoxy, N-methylcarbamoyl, N,N-dimethylcarbamoyl, and N-cyclopropylcarbamoyl.
Ar is more particularly selected from

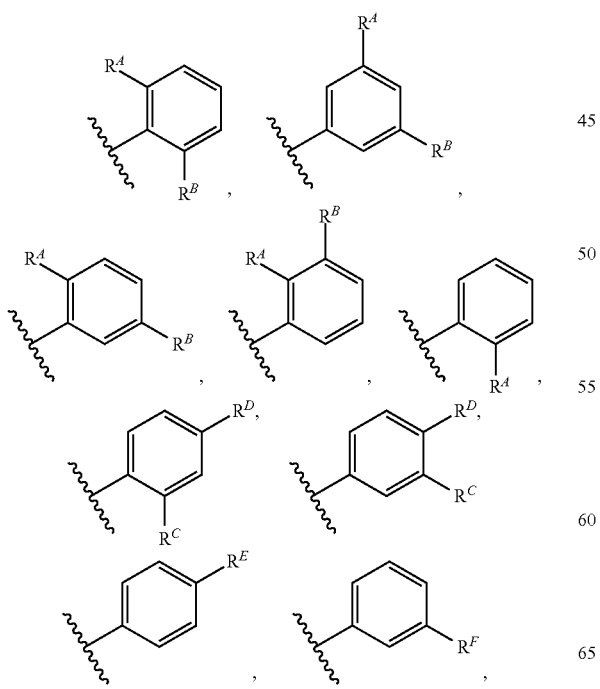

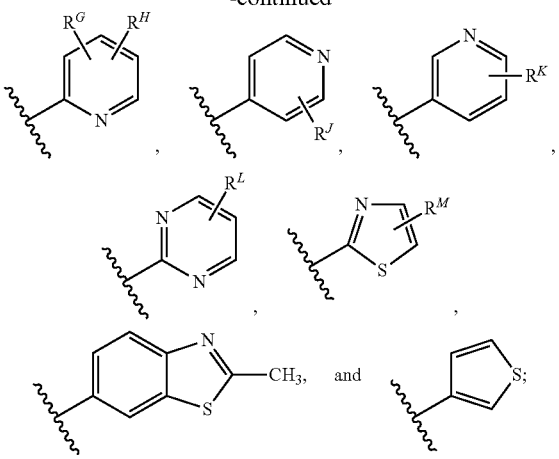

wherein, $R^A$ and $R^B$ are independently selected from halogen and methyl, $R^C$ is selected from halogen, methyl and methoxy, $R^D$ is selected from halogen, cyano, methyl, N-methylcarbamoyl, $R^E$ is selected from hydrogen, halogen, methyl, N-cyclopropylcarbamoyl, N-methylcarbamoyl, N,N-dimethylcarbamoyl, and 3-thiophenyl, $R^F$ is selected from halogen, methyl, N-methylcarbamoyl, and trifluoromethyl, $R^G$ and $R^H$ are independently selected from hydrogen, halogen, methyl, and N-methylcarbamoyl, $R^J$ is selected from hydrogen and methyl, $R^K$ is selected from hydrogen, halogen, methyl and phenyl, $R^L$ is selected from hydrogen and ethyl, and $R^M$ is selected from hydrogen, methyl and N-methylcarbamoyl.

Ring A is more particularly selected from

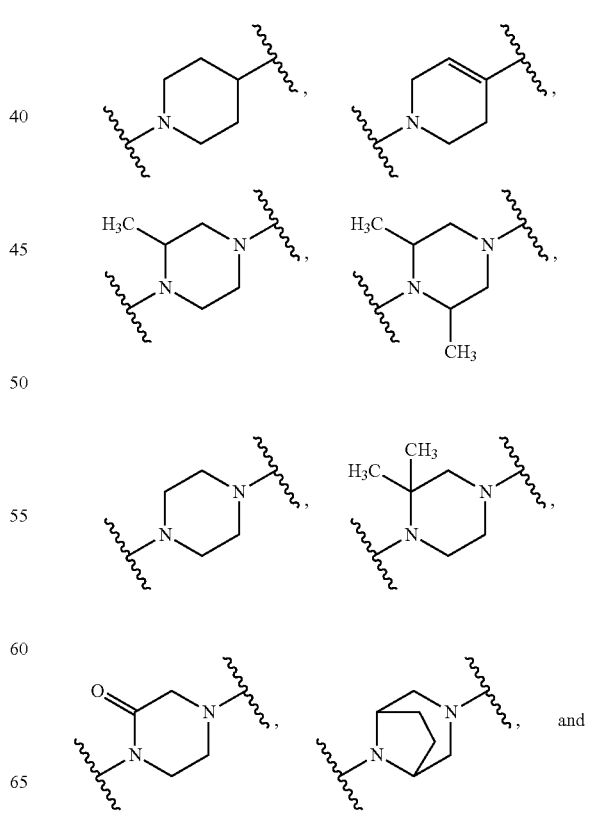

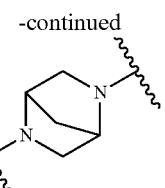

General terms used in formula can be defined as follows; however, the meaning stated should not be interpreted as limiting the scope of the term per se.

The term 'alkyl', as used herein, means a straight chain or branched hydrocarbon containing from 1 to 20 carbon atoms. Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term 'alkenyl', as used herein, means an alkyl group containing at least one double bond.

The 'alkyl', and 'alkenyl' as defined hereinabove may be substituted with 1 to 4 substituents independently selected from oxo (=O), halogen, cyano, perhaloalkyl, cycloalkyl, cycloalkenyl, aryl, heteroaryl, heterocyclyl, —OR$^{12a}$, SO$_2$(alkyl), —C(=O)O(alkyl), —C(=O)N(H)R$^{12}$, —C(=O)N(alkyl)$_2$, —N(H)C(=O)(alkyl), N(H)R$^{12}$, and —N(alkyl)R$^{12}$; R$^{12}$ is selected from hydrogen and alkyl; and R$^{12a}$ is selected from hydrogen, alkyl, alkenyl, and perhaloalkyl.

The term 'perhaloalkyl', as used herein, means an alkyl group as defined hereinabove wherein all the hydrogen atoms of the said alkyl group are substituted with halogen. The perhaloalkyl group is exemplified by trifluoromethyl, pentafluoroethyl, and the like.

The term 'cycloalkyl' as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo [2.2.1]heptane, bicyclo[2.2.2]octane, bicyclo[3.2.2]nonane, bicyclo[3.3.1]nonane, and bicyclo[4.2.1]nonane, bicyclo [3.3.2]decane, bicyclo[3.1.0]hexane, bicyclo[410]heptane, bicyclo[3.2.0]heptanes, octahydro-1H-indene, spiro[2.5]octane, spiro[4.5]decane, spiro[bicyclo[4.1.0]heptane-2,1'-cyclopentane], hexahydro-2'H-spiro[cyclopropane-1,1'-pentalene]. Tricyclic ring systems are the systems wherein the bicyclic systems as described above are further annulated with third ring, which may be an alicyclic ring or aromatic ring. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3.7}$]nonane, and tricyclo [3.3.1.1$^{3.7}$]decane (adamantane).

The term 'cycloalkenyl', as used herein, means a cycloalkyl group containing at least one double bond.

The term 'carbocycle', as used herein, means a cyclic system made up of carbon atoms, which includes cycloalkyl, cycloalkenyl and aryl.

The 'cycloalkyl', 'cycloalkenyl' and 'carbocycle' as defined hereinabove may be substituted with 1 to 4 substituents independently selected from oxo (=O), halogen, cyano, alkyl, alkenyl, perhaloalkyl, —OR$^{12}$, —SO$_2$(alkyl), —C(=O)O(alkyl), —C(=O)N(H)R$^{12}$, —C(=O)N(alkyl) R$^{12}$, —N(H)C(=O)(alkyl), —N(H)R$^{12}$, —N(alkyl)$_2$; R$^{12}$ is selected from hydrogen and alkyl; and R$^{12a}$ is selected from hydrogen, alkyl, alkenyl, perhaloalkyl.

The term 'aryl', as used herein, refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons, e.g., tetrahydro-naphthalene.

The 'aryl' as defined hereinabove may be substituted with 1 to 4 substituents selected from halogen, nitro, cyano, hydroxy, alkyl, alkenyl, perhaloalkyl, cycloalkyl, cycloalkenyl, heterocyclyl, aryl, heteroaryl, —O-alkyl, —O-perhaloalkyl, —N(alkyl)alkyl, —N(H)alkyl, —NH$_2$, —SO$_2$-alkyl, —SO$_2$-perhaloalkyl, N(alkyl)C(=O)alkyl, —N(H)C(=O) alkyl, —C(=O)N(alkyl)alkyl, —C(=O)N(H)alkyl, C(=O) N(H)cycloalkyl, —C(=O)NH$_2$, —SO$_2$N(alkyl)alkyl, —SO$_2$N(H)alkyl, —SO$_2$NH$_2$, —C(=O)OH, —C(=O)O-alkyl, —O(C=O)N(alkyl)H, —O(C=O)N(alkyl)$_2$, O(C=O)N(cycloalkyl)H, —N(H)C(=O)N(aryl)H, —N(H) C(=O)N(alkyl)H, and N(H)C(=O)NH$_2$.

The term 'heteroaryl', as used herein, refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include, but not limited to, pyridyl, 1-oxopyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1,3]dioxol-4-yl, benzo[1,3]dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl and the like.

The 'heteroaryl' as defined hereinabove may be optionally substituted with 1 to 4 substituents selected from halogen, nitro, cyano, hydroxy, alkyl, alkenyl, perhaloalkyl, cycloalkyl, cycloalkenyl, heterocyclyl, aryl, heteroaryl, —O-alkyl, —O— perhaloalkyl, —N(alkyl)alkyl, —N(H)alkyl, —NH$_2$, —SO$_2$-alkyl, —SO$_2$-perhaloalkyl, —N(alkyl)C (=O)alkyl, —N(H)C(=O)alkyl, —C(=O)N(alkyl)alkyl, —C(=O)N(H)alkyl, C(=O)N(H)cycloalkyl, —C(=O) NH$_2$, —SO$_2$N(alkyl)alkyl, —SO$_2$N(H)alkyl, —SO$_2$NH$_2$, —C(=O)OH, —C(=O)O-alkyl, —O(C=O)N(alkyl)H, —O(C=O)N(alkyl)$_2$, O(C=O)N(cycloalkyl)H, —N(H)C(=O)N(aryl)H, —N(H)C(=O)N(alkyl)H, and N(H)C(=O)NH$_2$.

The term 'heterocycle' or 'heterocyclic' as used herein, means a 'cycloalkyl' group wherein one or more of the carbon atoms replaced by heteroatom selected from N, S and O. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl(thiomorpholine sulfone), thiopyranyl, and trithianyl. Representative examples of bicyclic heterocycle include, but are not limited to, 1,2,3,4-tetrahydroisoquinolin-2-yl, 1,2,3,4-tetrahydroquinolin-1-yl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The term heterocycle also includes bridged and spiro heterocyclic systems such as azabicyclo[3.2.1]octane, azabicyclo[3.3.1]nonane, 8-oxa-3-azabicyclo[3.2.1]octan-3-yl, 3-oxa-8-azabicyclo[3.2.1]octan-8-yl, 6-oxa-3-azabicyclo[3.1.1]heptan-3-yl, 8-azabicyclo[3.2.1]octan-8-yl, 3-azabicyclo[3.2.1]octan-3-yl, 3-azabicyclo[3.1.0]hexan-3-yl, 6-azaspiro[2.5]octan-6-yl, 5-azaspiro[2.5]octan-5-yl, 4-azaspiro[2.4]heptan-4-yl, and the like.

The 'heterocycle' as defined hereinabove, wherein the ring carbon may be optionally substituted with 1 to 4 substituents selected from oxo (=O), halogen, cyano, alkyl, alkenyl, perhaloalkyl, —OR$^{12}$, —SO$_2$(alkyl), —C(=O)O(alkyl), C(=O)N(H)R$^{12}$, —C(=O)N(alkyl)R$^{12}$, —N(H)C(=O)(alkyl), —N(H)R$^{12}$, —N(alkyl)$_2$; R$^{12}$ is selected from hydrogen and alkyl;

The 'heterocycle' as defined hereinabove, wherein the ring nitrogen may be optionally substituted with a substituent selected from alkyl, alkenyl, cycloalkyl, cycloalkenyl, aryl, heteroaryl, —SO$_2$(alkyl), —C(=O)(alkyl), C(=O)O(alkyl), C(=O)N(H)R$^{12}$, and —C(=O)N(alkyl)R$^{12}$; R$^{12}$ is selected from hydrogen and alkyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non-adjacent ring atoms.

Whenever a range of the number of atoms in a structure is indicated (e.g., a $C_1$ to $C_{20}$ alkyl, $C_2$ to $C_{20}$ alkenyl etc.), it is specifically contemplated that any sub-range or individual number of carbon atoms falling within the indicated range also can be used. Thus, for instance, the recitation of a range of 1-6 carbon atoms (e.g., $C_1$ to $C_6$), 2-6 carbon atoms (e.g., $C_2$ to $C_6$), 3-6 carbon atoms (e.g., $C_3$ to $C_6$), as used with respect to any chemical group (e.g., alkyl, alkenyl, etc.) referenced herein encompasses and specifically describes 1, 2, 3, 4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, 4-6 carbon atoms as appropriate).

In accordance with an embodiment, the invention provides a compound, its stereoisomers, racemates, and pharmaceutically acceptable salt thereof as described hereinabove wherein the compound of general formula (I) is selected from:

2'-(3-(4-(4-fluorophenyl)piperazin-1-yl)propyl)-6',7'-dihydro-3'H-spiro[cyclopropane-1,8'-quinazolin]-4'(5'H)-one (Compound 1);

2'-(3-(4-(4-chlorophenyl)piperazin-1-yl)propyl)-6',7'-dihydro-3'H-spiro[cyclopropane-1,8'-quinazolin]-4'(5'H)-one (Compound 2);

2'-(3-(4-phenyl-5,6-dihydropyridin-1(2H)-yl)propyl)-6',7'-dihydro-3'H-spiro[cyclopropane-1,8'-quinazolin]-4'(5'H)-one (Compound 3);

2'-(3-(3-(4-fluorophenyl)-3,8-diazabicyclo[3.2.1]octan-8-yl)propyl)-4a',5',6',7'-tetrahydro-3'H-spiro[cyclopropane-1,8'-quinazolin]-4'(8a'H)-one (Compound 4);

2'-(3-(4-(4-fluorophenyl)piperazin-1-yl)propyl)-7',8'-dihydro-3'H-spiro[cyclopropane-1,6'-quinazolin]-4'(5'H)-one (Compound 5);

2'-(3-(4-(4-chlorophenyl) piperazin-1-yl)propyl)-7',8'-dihydro-3'H-spiro[cyclopropane-1,6'-quinazolin]-4'(5'H)-one (Compound 6);

2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one (Compound 7);

2'-(3-(8-(4-fluorophenyl)-3,8-diazabicyclo[3.2.1]octan-3-yl)propyl)-7',8'-dihydro-3'H-spiro[cyclopropane-1,6'-quinazolin]-4'(5'H)-one (Compound 8);

2'-(3-(4-(4-fluorophenyl)-5,6-dihydropyridin-1(2H)-yl)propyl)-7',8'-dihydro-3'H-spiro[cyclopropane-1,6'-quinazolin]-4'(5'H)-one (Compound 9);

2'-(3-(4-(3,4-dichlorophenyl)piperazin-1-yl)propyl)-7',8'-dihydro-3'H-spiro[cyclopropane-1,6'-quinazolin]-4'(5'H)-one (Compound 10);

2'-(3-(5-(4-fluorophenyl)-2,5-diazabicyclo[2.2.1]heptan-2-yl)propyl)-7',8'-dihydro-3'H-spiro[cyclopropane-1,6'-quinazolin]-4'(5'H)-one (Compound 11);

2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one (Compound 12);

2'-(3-(4-phenylpiperazin-1-yl)propyl)-7',8'-dihydro-3'H-spiro[cyclopropane-1,6'-quinazolin]-4'(5'H)-one (Compound 13);

2'-(3-(4-(2-chlorophenyl) piperazin-1-yl)propyl)-7',8'-dihydro-3'H-spiro[cyclopropane-1,6'-quinazolin]-4'(5'H)-one (Compound 14);

2'-(3-(4-(4-fluorophenyl)piperazin-1-yl)propyl)-5',6'-dihydro-3'H-spiro[cyclopropane-1,7'-quinazolin]-4'(8'H)-one (Compound 15);

2'-(3-(4-(4-fluorophenyl)-5,6-dihydropyridin-1(2H)-yl)propyl)-5',6'-dihydro-3'H-spiro[cyclopropane-1,7'-quinazolin]-4'(8'H)-one (Compound 16);

2'-(3-(4-phenyl-5,6-dihydropyridin-1(2H)-yl)propyl)-5',6'-dihydro-3'H-spiro[cyclopropane-1,7'-quinazolin]-4'(8'H)-one (Compound 17);

2'-(3-(4-(3-chlorophenyl) piperazin-1-yl)propyl)-7',8'-dihydro-3'H-spiro[cyclopropane-1,6'-quinazolin]-4'(5'H)-one (Compound 18);

2'-(3-(4-phenylpiperidin-1-yl)propyl)-7',8'-dihydro-3'H-spiro[cyclopropane-1,6'-quinazolin]-4'(5'H)-one (Compound 19);

2'-(3-(4-(pyridin-2-yl)piperazin-1-yl)propyl)-7',8'-dihydro-3'H-spiro[cyclopropane-1,6'-quinazolin]-4'(5'H)-one (Compound 20);

2'-(3-(4-(4-fluorophenyl)piperazin-1-yl)butyl)-7',8'-dihydro-3'H-spiro[cyclopropane-1,6'-quinazolin]-4'(5'H)-one (Compound 21);

2'-(3-(4-(3-(trifluoromethyl)phenyl)piperazin-1-yl)propyl)-7',8'-dihydro-3'H-spiro[cyclopropane-1,6'-quinazolin]-4'(5'H)-one (Compound 22);

2'-(3-(4-(m-tolyl)piperazin-1-yl)propyl)-7',8'-dihydro-3'H-spiro[cyclopropane-1,6'-quinazolin]-4'(5'H)-one (Compound 23);

2-(3-(4-(4-fluorophenyl)piperazin-1-yl)propyl)-5a,6,6a,7-tetrahydro-3H-cyclopropa[g]quinazolin-4(5H)-one (Compound 24);

2-(3-(4-phenylpiperazin-1-yl)propyl)-5a,6,6a,7-tetrahydro-3H-cyclopropa[g]quinazolin-4(5H)-one (Compound 25);

2'-(3-(4-(4-fluorophenyl)-2,6-dimethylpiperazin-1-yl)propyl)-7',8'-dihydro-3'H-spiro[cyclopropane-1,6'-quinazolin]-4'(5'H)-one (Compound 26);

2'-(3-(4-(4-fluorophenyl)-2-methylpiperazin-1-yl)propyl)-7',8'-dihydro-3'H-spiro[cyclopropane-1,6'-quinazolin]-4'(5'H)-one (Compound 27);

2'-(3-(4-(2-fluorophenyl)piperazin-1-yl)propyl)-7',8'-dihydro-3'H-spiro[cyclopropane-1,6'-quinazolin]-4'(5'H)-one (Compound 28);

2'-(3-(4-(pyridin-4-yl)piperazin-1-yl)propyl)-7',8'-dihydro-3'H-spiro[cyclopropane-1,6'-quinazolin]-4'(5'H)-one (Compound 29);

2'-(3-(4-(4-fluorophenyl)piperazin-1-yl)-3-methylbutyl)-7',8'-dihydro-3'H-spiro[cyclopropane-1,6'-quinazolin]-4'(5'H)-one (Compound 30);

(E)-2'-(3-(4-(4-fluorophenyl)piperazin-1-yl)-3-methylbut-1-en-1-yl)-7',8'-dihydro-3'H-spiro[cyclopropane-1,6'-quinazolin]-4'(5'H)-one (Compound 31);

2'-(3-(4-(p-tolyl)piperazin-1-yl)propyl)-7',8'-dihydro-3'H-spiro[cyclopropane-1,6'-quinazolin]-4'(5'H)-one (Compound 32);

2'-(3-(4-(4-fluorophenyl)-2-oxopiperazin-1-yl)propyl)-7',8'-dihydro-3'H-spiro[cyclopropane-1,6'-quinazolin]-4'(5'H)-one (Compound 33);

2'-(3-(4-(2,4-dichlorophenyl)piperazin-1-yl)propyl)-7',8'-dihydro-3'H-spiro[cyclopropane-1,6'-quinazolin]-4'(5'H)-one (Compound 34);

2-(3-(4-(4-fluorophenyl)piperazin-1-yl)propyl)-5,6,7,8-tetrahydro-5,8-methanoquinazolin-4(3H)-one (Compound 35);

2-(3-(4-(4-chlorophenyl)piperazin-1-yl)propyl)-5,6,7,8-tetrahydro-5,8-methanoquinazolin-4(3H)-one (Compound 36);

(R)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one (Compound 37);

(S)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one (Compound 38);

2'-(3-(4-(pyridin-4-yl)piperazin-1-yl)cyclopent-1-en-1-yl)-7',8'-dihydro-3'H-spiro[cyclopropane-1,6'-quinazolin]-4'(5'H)-one (Compound 39);

(S)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 40);

(R)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 41);

(R)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 42);

(S)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 43);

N-cyclopropyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 44);

2'-(3-(4-(4-fluorophenyl)-3-oxopiperazin-1-yl)cyclopent-1-en-1-yl)-7',8'-dihydro-3'H-spiro[cyclopropane-1,6'-quinazolin]-4'(5'H)-one (Compound 45);

(R)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 46);

(S)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 47);

(R)-2'-(3-(4-(4-fluorophenyl)piperazin-1-yl)cyclopent-1-en-1-yl)-6',7'-dihydro-3'H-spiro[cyclopropane-1,8'-quinazolin]-4'(5'H)-one (Compound 48);

(S)-2'-(3-(4-(4-fluorophenyl)piperazin-1-yl)cyclopent-1-en-1-yl)-6',7'-dihydro-3'H-spiro[cyclopropane-1,8'-quinazolin]-4'(5'H)-one (Compound 49);

2'-(3-(4-(4-bromophenyl)piperazin-1-yl)cyclopent-1-en-1-yl)-7',8'-dihydro-3'H-spiro[cyclopropane-1,6'-quinazolin]-4'(5'H)-one (Compound 50);

(S)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 51);

(R)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 52);

(S)—N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 53);

(R)—N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 54);

(S)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 55);

(R)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 56);

(R)-2'-(3-(4-(5-chloropyridin-2-yl)piperazin-1-yl)cyclopent-1-en-1-yl)-7',8'-dihydro-3'H-spiro[cyclopropane-1,6'-quinazolin]-4'(5'H)-one (Compound 57);

(R)-2'-(3-(4-(5-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 58);

(R)-2'-(3-(4-(3,4-dichlorophenyl)piperazin-1-yl)cyclopent-1-en-1-yl)-7',8'-dihydro-3'H-spiro[cyclopropane-1,6'-quinazolin]-4'(5'H)-one (Compound 59);

(R)-2'-(3-(4-(3-chlorophenyl)piperazin-1-yl)cyclopent-1-en-1-yl)-7',8'-dihydro-3'H-spiro[cyclopropane-1,6'-quinazolin]-4'(5'H)-one (Compound 60);

(R)-2'-(3-(4-(2,4-difluorophenyl)piperazin-1-yl)cyclopent-1-en-1-yl)-7',8'-dihydro-3'H-spiro[cyclopropane-1,6'-quinazolin]-4'(5'H)-one (Compound 61);

(R)-2'-(3-(4-(3,4-difluorophenyl)piperazin-1-yl)cyclopent-1-en-1-yl)-7',8'-dihydro-3'H-spiro[cyclopropane-1,6'-quinazolin]-4'(5'H)-one (Compound 62);

(R)-2'-(3-(4-(4-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 63);

(R)-2'-(3-(4-(3-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 64);

(R)-2'-(3-(4-(2,4-dichlorophenyl)piperazin-1-yl)cyclopent-1-en-1-yl)-7',8'-dihydro-3'H-spiro[cyclopropane-1,6'-quinazolin]-4'(5'H)-one (Compound 65);

(R)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 66);

(R)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 67);

(R)-3-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 68);

(R)—N,N-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 69);

(R)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 70);

(S)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 71);

(R)—N-methyl-4-(1-(3-(4'-oxo-4',5',7',8'-tetrahydro-3'H-spiro[cyclopropane-1,6'-quinazolin]-2'-yl)cyclopent-2-en-1-yl)-1,2,3,6-tetrahydropyridin-4-yl)benzamide (Compound 72);

(R)-2'-(3-(4-(p-tolyl) piperazin-1-yl)cyclopent-1-en-1-yl)-7',8'-dihydro-3'H-spiro[cyclopropane-1,6'-quinazolin]-4'(5'H)-one (Compound 73);

(R)-2'-(3-(4-(4-methoxyphenyl)piperazin-1-yl)cyclopent-1-en-1-yl)-7',8'-dihydro-3'H-spiro[cyclopropane-1,6'-quinazolin]-4'(5'H)-one (Compound 74);

(R)-2'-(3-(4-(4-fluorophenyl)piperidin-1-yl)cyclopent-1-en-1-yl)-7',8'-dihydro-3'H-spiro[cyclopropane-1,6'-quinazolin]-4'(5'H)-one (Compound 75);

(R)—N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 76);

(R)-2'-(3-(4-(p-tolyl)piperidin-1-yl)cyclopent-1-en-1-yl)-7',8'-dihydro-3'H-spiro[cyclopropane-1,6'-quinazolin]-4'(5'H)-one (Compound 77);

(R)-2'-(3-(4-(3-fluorophenyl)piperazin-1-yl)cyclopent-1-en-1-yl)-7',8'-dihydro-3'H-spiro[cyclopropane-1,6'-quinazolin]-4'(5'H)-one (Compound 78);

(R)-2'-(3-(4-(2-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 79);

(R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 80);

(R)-2'-(3-(4-(2-methylbenzo[d]thiazol-6-yl)piperazin-1-yl)cyclopent-1-en-1-yl)-7',8'-dihydro-3'H-spiro[cyclopropane-1,6'-quinazolin]-4'(5'H)-one (Compound 81);

(R)-2'-(3-(4-(3-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 82);

(R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 83);

(R)-2'-(3-(4-(3-fluoro-4-methylphenyl) piperazin-1-yl)cyclopent-1-en-1-yl)-7',8'-dihydro-3'H-spiro[cyclopropane-1,6'-quinazolin]-4'(5'H)-one (Compound 84);

(R)-2'-(3-(4-(m-tolyl)piperazin-1-yl)cyclopent-1-en-1-yl)-7',8'-dihydro-3'H-spiro[cyclopropane-1,6'-quinazolin]-4'(5'H)-one (Compound 85);

(R)-2'-(3-(4-(4-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 86);

(R)—N-methyl-3-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 87);

(R)-2'-(3-(4-(2-fluoro-4-methylphenyl)piperazin-1-yl)cyclopent-1-en-1-yl)-7',8'-dihydro-3'H-spiro[cyclopropane-1,6'-quinazolin]-4'(5'H)-one (Compound 88);

(R)-2-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 89);

(R)-2'-(3-(4-(o-tolyl)piperazin-1-yl)cyclopent-1-en-1-yl)-7',8'-dihydro-3'H-spiro[cyclopropane-1,6'-quinazolin]-4'(5'H)-one (Compound 90);

(R)-2'-(3-(4-(thiophen-3-yl)piperazin-1-yl)cyclopent-1-en-1-yl)-7',8'-dihydro-3'H-spiro[cyclopropane-1,6'-quinazolin]-4'(5'H)-one (Compound 91);

(R)-2'-(3-(4-(2-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 92);

(R)-2'-(3-(4-(2-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 93);

(R)-2-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 94);

(R)-2'-(3-(4-(4-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 95);

(R)-2'-(3-(4-(4-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 96);

(R)—N, 3-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 97);

(R)—N, 2-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 98);

(R)-2'-(3-(4-(3-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 99);

(R)-2'-(3-(4-(2,3-difluorophenyl)piperazin-1-yl)cyclopent-1-en-1-yl)-7',8'-dihydro-3'H-spiro[cyclopropane-1,6'-quinazolin]-4'(5'H)-one (Compound 100);

(R)-2'-(3-(4-(thiazol-2-yl)piperazin-1-yl)cyclopent-1-en-1-yl)-7',8'-dihydro-3'H-spiro[cyclopropane-1,6'-quinazolin]-4'(5'H)-one (Compound 101);

(R)-2'-(3-(4-(4-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 102);

(R)-5-chloro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 103);

(R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-5-carboxamide (Compound 104);

(R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-4-carboxamide (Compound 105);

(R)-2'-(3-(4-(2,5-difluorophenyl)piperazin-1-yl)cyclopent-1-en-1-yl)-7',8'-dihydro-3'H-spiro[cyclopropane-1,6'-quinazolin]-4'(5'H)-one (Compound 106);

(R)-2'-(3-(4-(3,5-dichloropyridin-2-yl)piperazin-1-yl)cyclopent-1-en-1-yl)-7',8'-dihydro-3'H-spiro[cyclopropane-1,6'-quinazolin]-4'(5'H)-one (Compound 107);

(R)-2'-(3-(4-(3-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 108);

(R)-2'-(3-(4-(3,5-difluorophenyl)piperazin-1-yl)cyclopent-1-en-1-yl)-7',8'-dihydro-3'H-spiro[cyclopropane-1,6'-quinazolin]-4'(5'H)-one (Compound 109);

(R)-2'-(3-(4-(2,6-difluorophenyl)piperazin-1-yl)cyclopent-1-en-1-yl)-7',8'-dihydro-3'H-spiro[cyclopropane-1,6'-quinazolin]-4'(5'H)-one (Compound 110);

(R)-3-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzonitrile (Compound 111);

(R)-5-fluoro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 112);

(R)-2'-(3-(4-(5-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 113);

(R)-2'-(3-(4-(4-fluoro-3-methoxyphenyl)piperazin-1-yl)cyclopent-1-en-1-yl)-7',8'-dihydro-3'H-spiro[cyclopropane-1,6'-quinazolin]-4'(5'H)-one (Compound 114);

(R)-2'-(3-(4-(3-chloro-5-fluorophenyl)piperazin-1-yl)cyclopent-1-en-1-yl)-7',8'-dihydro-3'H-spiro[cyclopropane-1,6'-quinazolin]-4'(5'H)-one (Compound 115);

(R)-2'-(3-(4-(2-fluorophenyl)piperazin-1-yl)cyclopent-1-en-1-yl)-7',8'-dihydro-3'H-spiro[cyclopropane-1,6'-quinazolin]-4'(5'H)-one (Compound 116);

(R)-2'-(3-(4-phenylpiperazin-1-yl)cyclopent-1-en-1-yl)-7',8'-dihydro-3'H-spiro[cyclopropane-1,6'-quinazolin]-4'(5'H)-one (Compound 117);

2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one (Compound 118);

2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one (Compound 119);

2'-((1S,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 120);

2'-((1R,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 121);

(R)-2'-(3-(4-(2-chlorophenyl)piperazin-1-yl)cyclopent-1-en-1-yl)-7',8'-dihydro-3'H-spiro[cyclopropane-1,6'-quinazolin]-4'(5'H)-one (Compound 122);

(R)-2'-(3-(4-(5-fluoro-2-methylphenyl) piperazin-1-yl)cyclopent-1-en-1-yl)-7',8'-dihydro-3'H-spiro[cyclopropane-1,6'-quinazolin]-4'(5'H)-one (Compound 123);

(R)-2'-(3-(4-(5-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 124);

(R)-2'-(3-(4-(4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 125);

(R)-2'-(3-(4-(3-fluoro-5-methylphenyl) piperazin-1-yl)cyclopent-1-en-1-yl)-7',8'-dihydro-3'H-spiro[cyclopropane-1,6'-quinazolin]-4'(5'H)-one (Compound 126);

(R)-2-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzonitrile (Compound 127);

(R)-2'-(3-(4-(pyrimidin-2-yl)piperazin-1-yl)cyclopent-1-en-1-yl)-7',8'-dihydro-3'H-spiro[cyclopropane-1,6'-quinazolin]-4'(5'H)-one (Compound 128);

(R)-2'-(3-(4-(2-methylpyridin-3-yl)piperazin-1-yl)cyclopent-1-en-1-yl)-7',8'-dihydro-3'H-spiro[cyclopropane-1,6'-quinazolin]-4'(5'H)-one (Compound 129);

(R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)isonicotinamide (Compound 130);

(R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 131);

(R)-2'-(3-(4-(3-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 132);

(R)-2'-(3-(4-(4-fluoro-2-methoxyphenyl)piperazin-1-yl)cyclopent-1-en-1-yl)-7',8'-dihydro-3'H-spiro[cyclopropane-1,6'-quinazolin]-4'(5'H)-one (Compound 133);

(R)-3-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 134);

(R)-2'-(3-(4-(5-ethylpyrimidin-2-yl)piperazin-1-yl)cyclopent-1-en-1-yl)-7',8'-dihydro-3'H-spiro[cyclopropane-1,6'-quinazolin]-4'(5'H)-one (Compound 135);

(R)-2'-(3-(4-(3,4-dimethylphenyl)piperazin-1-yl)cyclopent-1-en-1-yl)-7',8'-dihydro-3'H-spiro[cyclopropane-1,6'-quinazolin]-4'(5'H)-one (Compound 136);

(R)-2'-(3-(4-(5-fluoro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 137);

(R)-2'-(3-(4-(5-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 138);

(R)-2'-(3-(4-(2-chloro-6-fluorophenyl)piperazin-1-yl)cyclopent-1-en-1-yl)-7',8'-dihydro-3'H-spiro[cyclopropane-1,6'-quinazolin]-4'(5'H)-one (Compound 139);

(R)-2'-(3-(4-(2,3-dimethylphenyl)piperazin-1-yl)cyclopent-1-en-1-yl)-7',8'-dihydro-3'H-spiro[cyclopropane-1,6'-quinazolin]-4'(5'H)-one (Compound 140);

(R)-2'-(3-(4-(5-chloro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 141);

(R)-2'-(3-(4-(5-fluoropyridin-3-yl)piperazin-1-yl)cyclopent-1-en-1-yl)-7',8'-dihydro-3'H-spiro[cyclopropane-1,6'-quinazolin]-4'(5'H)-one (Compound 142);

(R)-2'-(3-(4-(3-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 143);

(R)-2'-(3-(4-(2,5-dimethylphenyl)piperazin-1-yl)cyclopent-1-en-1-yl)-7',8'-dihydro-3'H-spiro[cyclopropane-1,6'-quinazolin]-4'(5'H)-one (Compound 144);

(R)-2'-(3-(4-(6-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 145);

(R)-2'-(3-(4-(5-chloro-3-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 146);

(R)-2'-(3-(4-(2-methylpyridin-4-yl)piperazin-1-yl)cyclopent-1-en-1-yl)-7',8'-dihydro-3'H-spiro[cyclopropane-1,6'-quinazolin]-4'(5'H)-one (Compound 147);

(R)-2'-(3-(4-(4-((thiophen-3-yl)phenyl)piperazin-1-yl)cyclopent-1-en-1-yl)-7',8'-dihydro-3'H-spiro[cyclopropane-1,6'-quinazolin]-4'(5'H)-one (Compound 148);

2'-((1S,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 149);

2'-((1R,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 150);

According a feature of the present invention, the compound of general formula (I) where all the symbols are defined earlier, can be prepared by methods given below.

Scheme 1 shows a method of preparation of a compound in accordance with an embodiment of the formula I. Compound of formula I can be prepared from compound of formula II where symbols are the same as described under generic formula I.

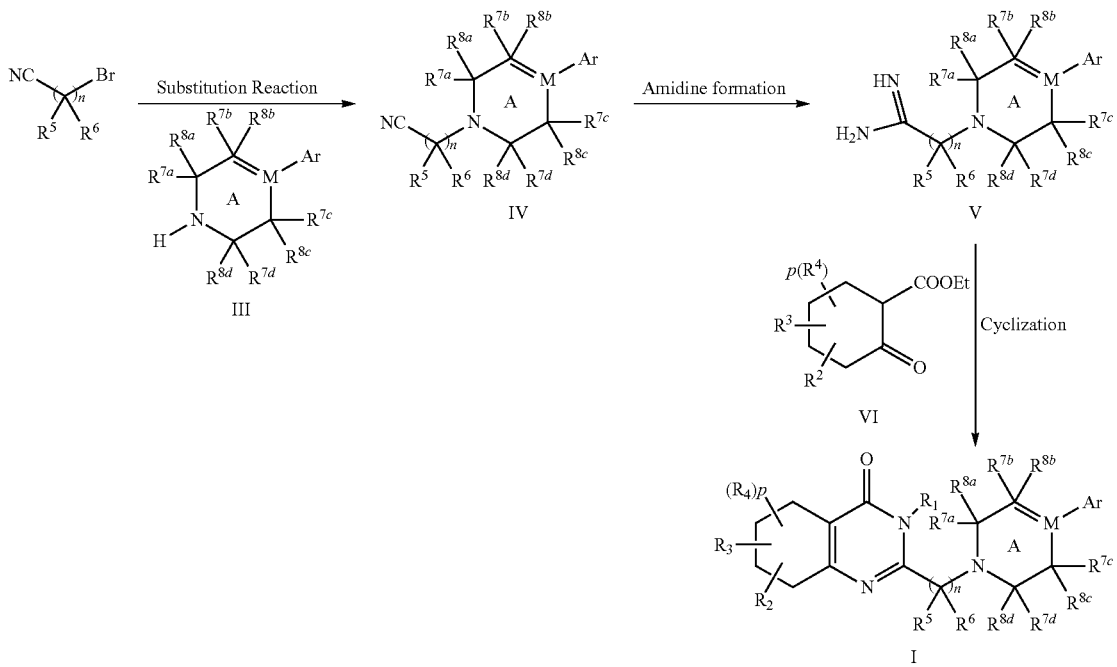

Scheme 1

2'-((1S,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 151);

2'-((1R,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 152);

2'-((1R,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 153);

2'-((1S,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 154);

2'-((1S,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 155);

2'-((1R,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 156);

(R)-2'-(3-(4-(6-phenylpyridin-3-yl)piperazin-1-yl)cyclopent-1-en-1-yl)-7',8'-dihydro-3'H-spiro[cyclopropane-1,6'-quinazolin]-4'(5'H)-one (Compound 157);

(R)-2'-(3-(4-([1,1'-biphenyl]-4-yl)piperazin-1-yl)cyclopent-1-en-1-yl)-7',8'-dihydro-3'H-spiro[cyclopropane-1,6'-quinazolin]-4'(5'H)-one (Compound 158); and 2'-(3-(3-(4-chlorophenyl)-3,8-diazabicyclo[3.2.1]octan-8-yl)cyclopent-1-en-1-yl)-7',8'-dihydro-3'H-spiro[cyclopropane-1,6'-quinazolin]-4'(5'H)-one (Compound 159).

The compound of formula II is reacted with a compound of formula III, where all symbols are as defined under formula I, under a suitable condition required or generally used in synthetic organic chemistry in presence of suitable solvents, for example, a halogenated hydrocarbon such as chloroform and dichloromethane, an aromatic hydrocarbon such as xylene, benzene and toluene, an ether type solvent such as diethyl ether, tetrahydrofuran and 1,4-dioxane, an aprotic polar solvent such as dimethylformamide, N-methyl-2-pyrrolidinone, dimethylsulfoxide, acetonitrile, in presence of suitable base such as potassium carbonate, triethylamine, diethylisopropylamine, to give compound of formula IV.

Compounds of formula IV where all symbols are same as defined earlier in compounds of formula I was subjected to amidine formation reaction in presence of methanolic HCl followed by methanolic ammonia or directly with methylchloroaluminium amide (MeAl(Cl)NH$_2$) in toluene to give compound of formula V. The reaction may be carried out according to the procedure given in the literature such as *Tetrahedron Letter* 1995, 36, 8761.

Compound of formula V or its salt where all symbols are defined in the general formula I can be reacted with a cyclic keto ester of compound of formula VI or its tautomer, where symbols are the same as for general formula I, in the presence of suitable solvents, for example, methanol or ethanol in the presence of appropriate base like, such as inorganic bases, for example, an alkali metal alkoxide, hydroxide, carbonate or bicarbonate thereof, or organic bases such as a trialkyl amine or the like at a temperature between 0-120° C. over a period of 1-12 h to give compounds for formula I.

More preferably, compound of formula II is selected from compound IIA and IIB.

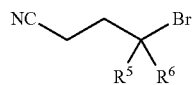

IIA

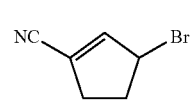

IIB

More preferably compound of formula III is selected from IIIA, IIIB, IIIC, IIID, IIIE, IIIF, and IIIG.

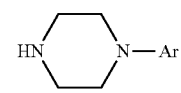

IIIA

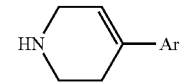

IIIB

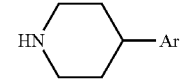

IIIC

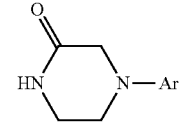

IIID

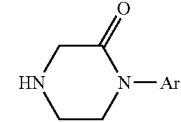

IIIE

IIIF

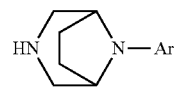

IIIG

More preferably compound of formula VI is selected from compounds VIA, VIB, VIC, VID, and VIE. These compounds can be synthesized by following the procedures reported in EP2208728, US2010144745, US200715792, *J. Org. Chem.* 1982, 47, 3211.

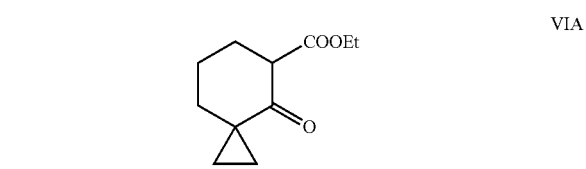

VIA

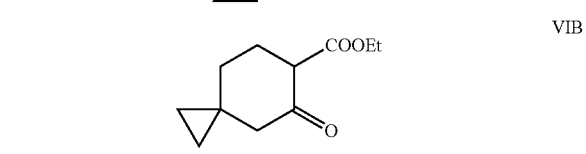

VIB

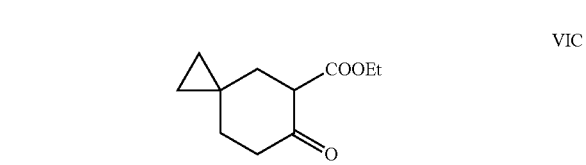

VIC

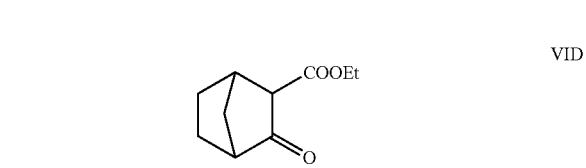

VID

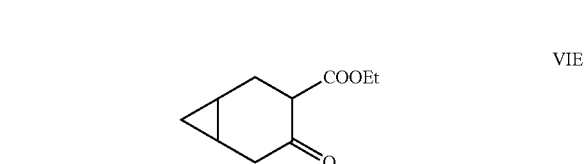

VIE

Scheme 2 shows a method of preparation of a compound of formula III starting from compound of formula (i a) and (i b).

Scheme 2

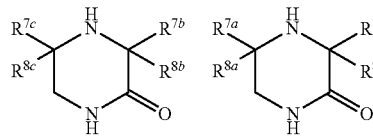

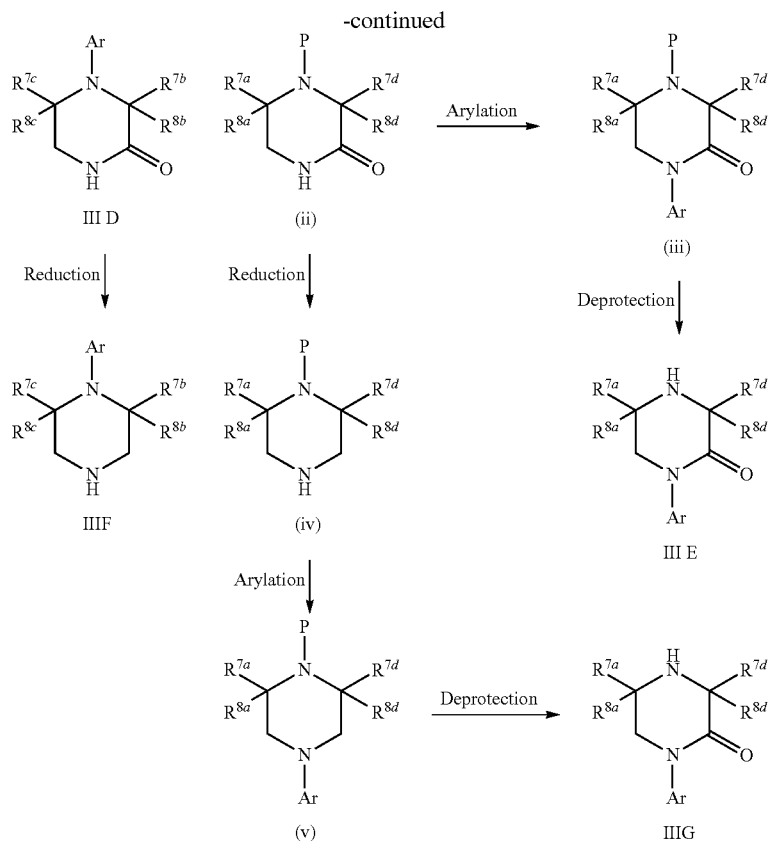

The compound of formula III can be prepared from the compound represented by general formula (i a) and (i b). Compounds of formula (i a) and (i b) were in turn prepared by the procedures described in the literature such as US2002068748, WO2005016900, US20050222166, WO2006051851, and *Tetrahedron*. 1992, 48, 4985.

The compound of formula (I b) can be protected by any suitable N-protecting groups known in literature to give compound of formula (ii). In an embodiment, the protection reaction was carried out using benzyl halide in presence of triethylamine in dichloromethane.

The compound of formula (ii) was subjected to Buchwald coupling with Ar-L, where Ar is as defined in the formula I and L is Cl, Br, or I to obtain a compound of formula (iii). Buchwald coupling can be can be carried out under any reaction condition known in the art. Preferably, the Buchwald coupling is carried out in a solvent such as toluene, tert-butanol, dimethylformamide, iso-propyl alcohol, 1,4-dioxane, 1,2-dimethoxyethane, tetrahydrofuran, and/or acetonitrile, in presence of a base such as potassium phosphate, potassium carbonate, sodium tert-butoxide, cesium carbonate, lithium hexamethyl disilazane or the like, palladium catalysts such as [Pd$_2$(dba)$_3$], Pd(OAc)$_2$ at a temperature between 50-160° C. and ligand such as 2,2'-Bis(diphenylphosphino)-1,1'-binaphthyl (BINAP) 2-Dicyclohexylphosphino-2',4',6'-triisopropylbiphenyl (XPhos), 2-Dicyclohexylphosphino-2'-(N,N-dimethylamino)biphenyl (DavePhos), (2-Biphenyl)di-tert-butylphosphine (JohnPhos), 2-Dicyclohexylphosphino-2',6'-dimethoxybiphenyl (SPhos), 2-Dicyclohexylphosphino-2'-methylbiphenyl (MePhos) or the like.

Any suitable protecting groups such as but not limited to Boc, Cbz, Bn can be utilized, and they can be removed from compound of formula (iii) to obtain compound of formula IIIE. Deprotection reaction of the N-protecting groups can be carried out by standard procedures generally used in synthetic organic chemistry or well known in literature such as *Protecting Groups in Organic Synthesis*, 2$^{rd}$ Edition, Greene, T. W. and Wuts, P. G. M.; Wiley Interscience, 1999.

The compound of formula (ii) can be treated with a suitable reducing agent known for converting amide to amine to give compound of formula (iv). The reaction may be carried out using reducing agent such as LiAlH$_4$, BH$_3$ in the presence of solvents such as tetrahydrofuran or diethyl ether at a temperature between 0-100° C.

The compound of formula (iv) was subjected to Buchwald coupling with Ar-L, where Ar is as defined in the formula I and L is Cl, Br, I to obtain the compound of formula (v).

Any protecting groups such as but not limited to Boc, Cbz, Bn can be removed from compound of formula (v) to obtain the compound of formula IIIG. The deprotection reaction for N-protecting groups can be carried out by standard procedures generally used in synthetic organic chemistry or well known in the literature; e.g., Greene T. W., et al., 1999.

The compound of formula IIID can be prepared from compound of formula (i a) by Buchwald coupling with Ar-L as described above for the synthesis of compound of formula (iii) from compound of formula (ii). Also, the compound of formula IIIF can be prepared from compound of formula IIID by reduction of the amide group to an amine group following the procedures described above for synthesis of compound of formula (iv) from compound of formula (i b).

Scheme 3 shows alternative methods of preparation of a compound of formula IV, where A ring is IIIA, from compound of formula IIB:

Scheme 3

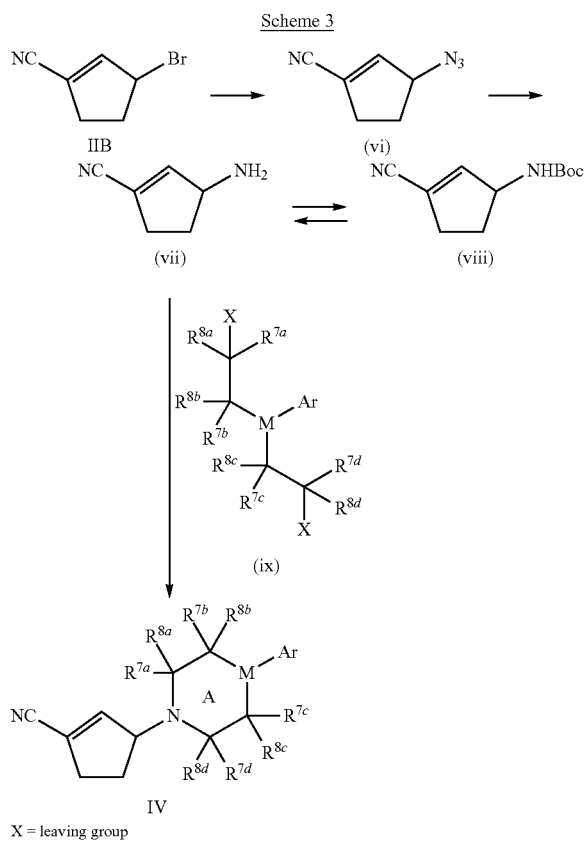

X = leaving group

The compound of formula IIB is reacted with NaN₃ under suitable condition in presence of suitable solvent(s), e.g., a halogenated hydrocarbon such as chloroform and dichloromethane, an aromatic hydrocarbon such as xylene, benzene and toluene, an ether such as diethyl ether, tetrahydrofuran and 1,4-dioxane, an aprotic polar solvent such as dimethylformamide, N-methyl-2-pyrrolidinone, dimethylsulfoxide, acetonitrile, in presence of a suitable base such as potassium carbonate, triethylamine, or diethylisopropylamine, to give compound of formula (vi).

The compound of formula (vii) or its salt can be produced from compound of formula (vi) under suitable reaction conditions usually applied in Staudinger reaction. This involves formation of phosphazenes from corresponding azido compound upon reaction with phosphane, e.g., triphenyl phosphphene, trialkyl phosphite or like, followed by hydrolysis of the phosphazenes, which may be conveniently accomplished by reaction with water. The reaction was carried out in the presence of suitable solvents such as THF, DMF, halogenated hydrocarbon, aromatic hydrocarbon, water or mixtures thereof or the like at a temperature between 0-120° C. over a period of 1-12 h.

The compound of formula (vii) can be further reacted with any N-protecting reagents known in literature to give compound of formula (viii). In an embodiment, protection reaction can be carried out by using (Boc)₂O in the presence of triethylamine in dichloromethane.

Protecting groups such as Boc, Cbz, Bn can be removed from the compound of formula (viii) to obtain compound of formula (vii). Deprotection reaction of N-protecting groups can be carried out by using standard procedures generally used in synthetic organic chemistry or well known in the literature, e.g., Greene, T. W., et al., 1999.

The compound of formula (vii) may be treated with compound of formula (ix) where, X is any leaving group, for example Cl, Br, I, OTs, OMs, or OTf, and other symbols are as defined earlier in formula I in the presence of a base such as diisopropylethylamine, triethylamine, or sodium carbonate at a temperature between 20-120° C. to obtain the compound of formula IV. The compound of formula (ix) can be prepared using procedures described in US20050245534, *J. Med. Chem.* 2005, 48, 3525.

Scheme 4 shows yet another alternative method of preparation of compound of IV from compound of IIB:

Scheme 4

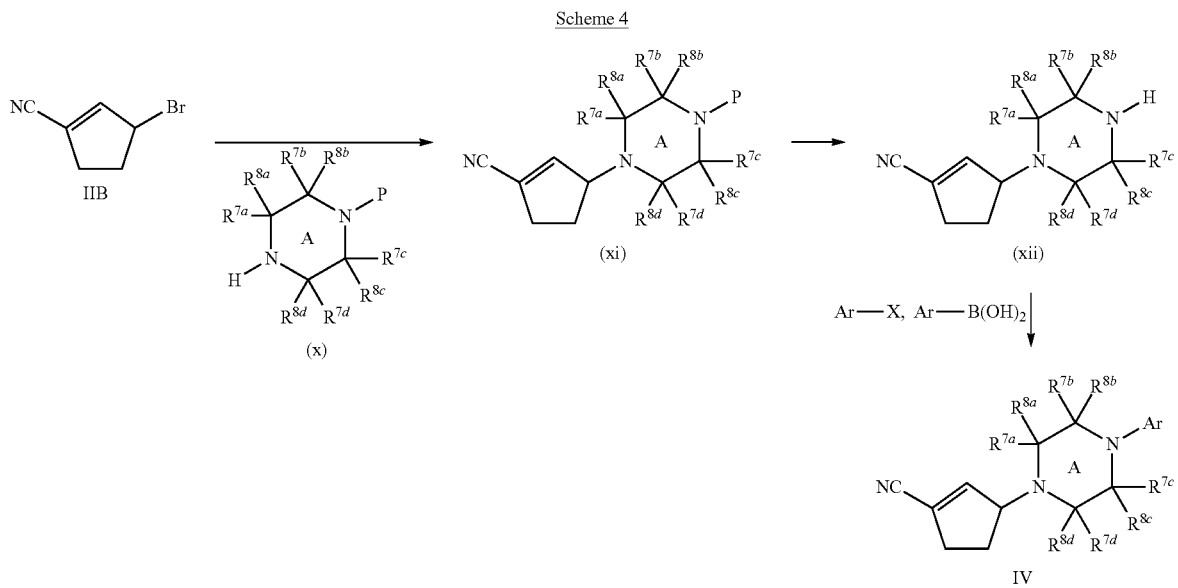

P = Protecting group

The compound of formula IV can be prepared alternatively from compound of formula IIB and compound of formula (x). Compound of formula IIB was reacted with compound of formula (x) under the condition described above for the synthesis of IV from II in scheme 1 to obtain compound of formula (xi). Compound of formula (xi) was then subjected to deprotection of N-protecting group to obtain compound of formula (xii). Deprotection reaction of N-protecting groups can be carried out using standard procedure generally used in synthetic organic chemistry or well known in the literature e.g., Greene T. W. et al., 1999.

The compound of formula (xii) was then subjected to Buchwald coupling with Ar-L, where Ar is as defined in the general formula I and L is Cl, Br, I to obtain compound of formula IV.

Scheme 5 outlines a method of preparation of a compounds 118, 119, 120 and 121. These compounds were prepared using the compound of formula (xiii a) or (xiii b).

Ester hydrolysis of compound of formula (xiv) gave compound of formula (xv), where all symbols are the same as defined for the compound of formula I. Ester hydrolysis can be carried out using procedures generally used in synthetic organic chemistry or well known in the art using regents such as sodium hydroxide, potassium hydroxide, lithium hydroxide or the like in a solvent such as water, alcohol, or THF or the like or mixture thereof. Preferably, lithium hydroxide is used for the reaction.

The compound of formula (xv) is reacted with a compound of formula (xvi), where all symbols are as defined under the compound of formula I to obtain compound of formula (xvii). The reaction was carried out using the conditions generally used for converting carboxylic acids to amides by a person skilled in art. The reaction may be carried out in the presence of solvents such as DMF, THF, chloroform, dichloromethane, xylene, benzene or mixtures there of or the like in the pres-

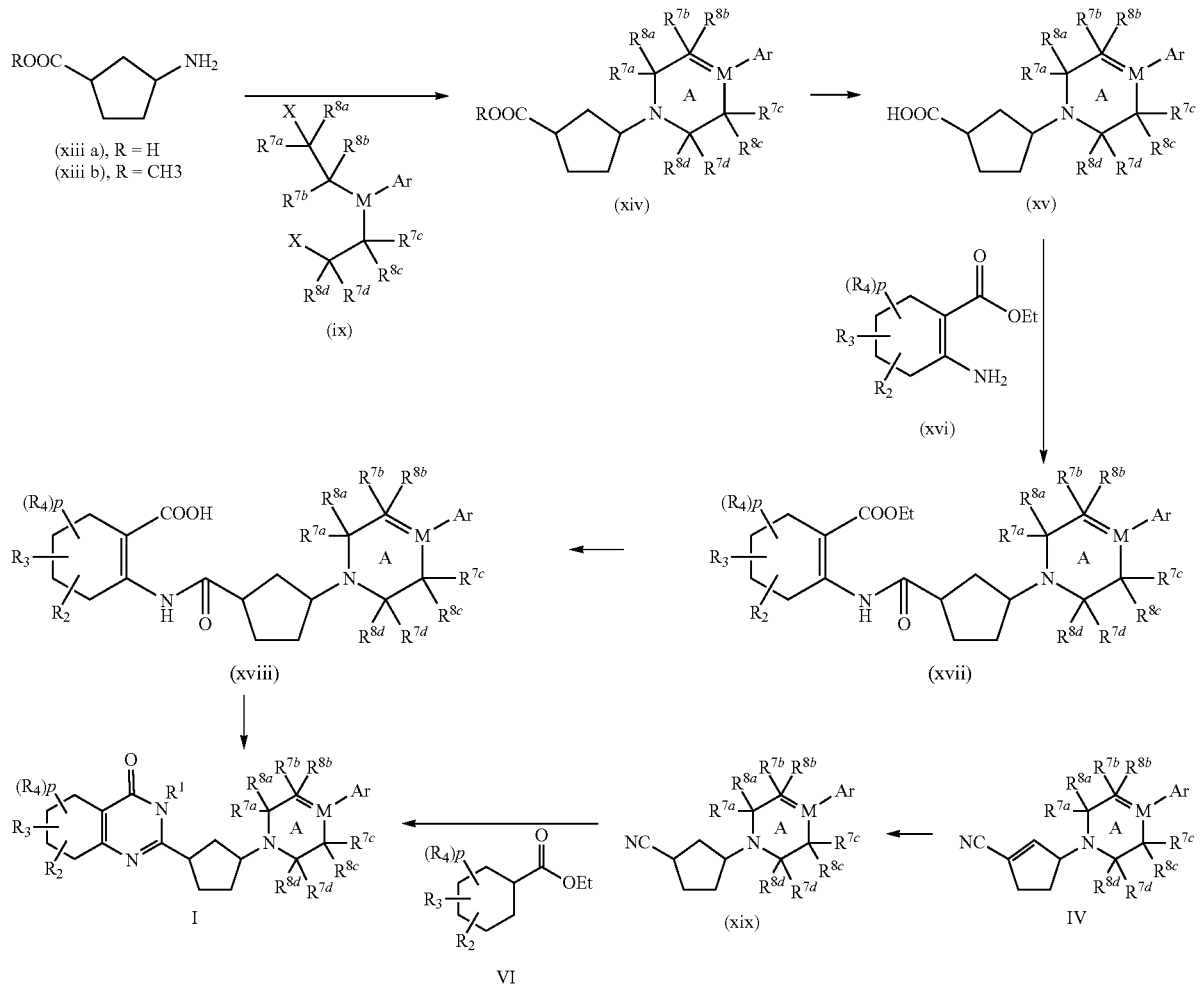

Scheme 5

The compound of formula (xiii b) can be prepared from compound of formula (xiii a) according to the conditions known in the art for converting carboxylic acids to esters.

The compound of formula (xiii b) can be treated with compound of formula (ix) to obtain compound of formula (xiv) as described in Scheme 3 for the synthesis of compound IV from compound of formula (vii) and compound of formula (ix).

ence of bases such as triethylamine, diisopropylethylamine, pyridine or the like at a temperature between 0-100° C. using reagent(s) such as thionyl chloride, phosphorus trichloride, oxalyl chloride, alkyl chloroformate, EDCI, DCC and auxiliary reagents such as HOBt, HOAt or the like or by using the methodology described in US20070197551.

The compound of formula (xvii) where all symbols are the same as described under compound of formula I can be hydrolyzed to compound of formula (xviii) as described for the synthesis of compound of formula (xv) from compound of formula (xiv).

The compound of formula (xviii) can be reacted with acetic anhydride, and successively reacting the reaction product with ammonia to obtain compound of formula I where symbols are same as described under the compound of formula I.

The compound of formula I can be prepared from compound of formula (xix) following the methodology described for the synthesis of I from compound of formula IV in Scheme 1.

Scheme 6 shows an alternative method of preparation of compound of formula (xv) from compound of formula (xx).

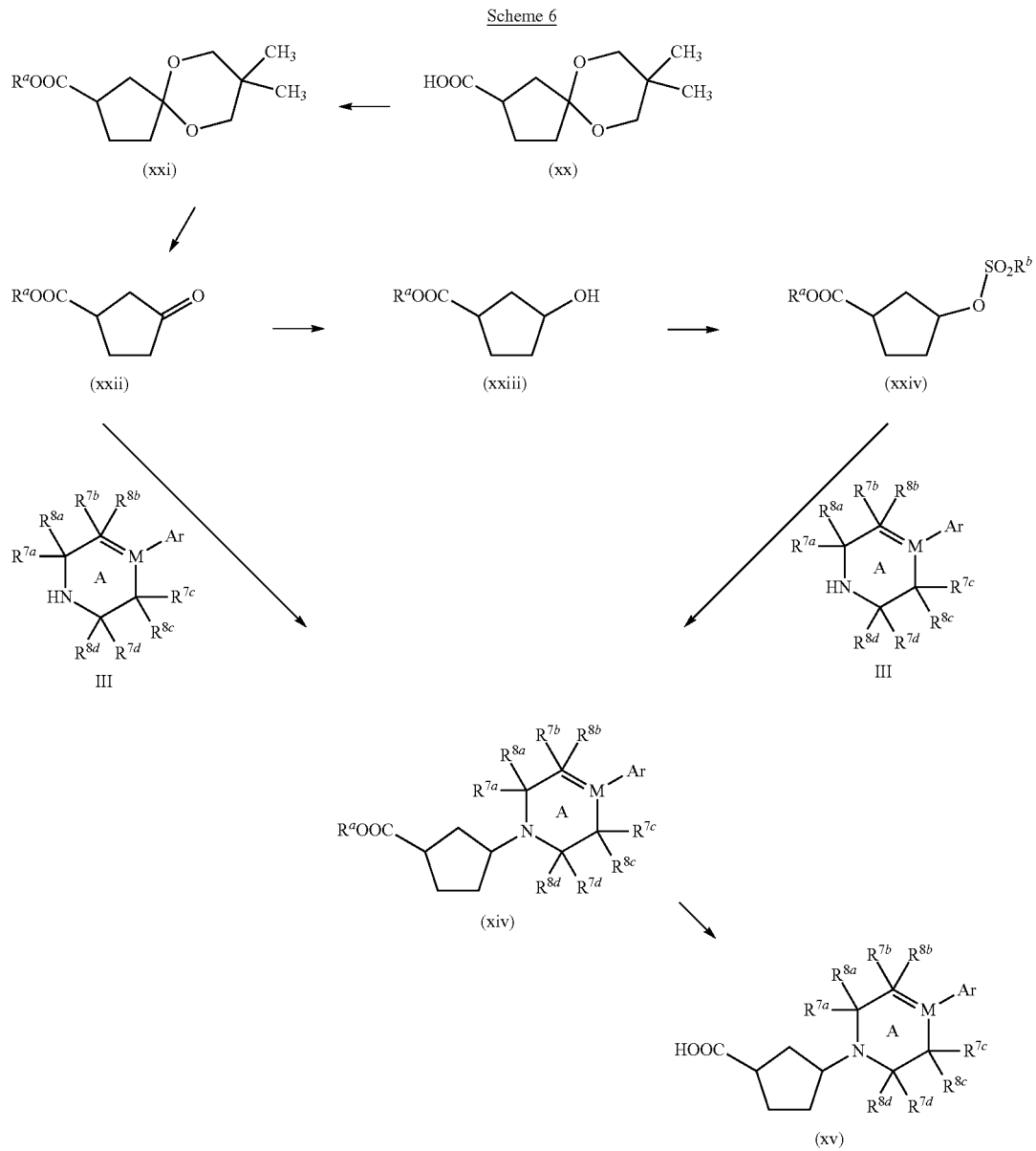

The compound of formula I can be alternatively prepared from compound of formula IV by converting it to compound of formula (xviii) under reduction condition known for reduction of activated alkene. The reaction may be carried out in presence of sodium borohydride, lithium borohydride or like in presence of solvents, for example, methyl alcohol, ethyl alcohol, propyl alcohol, isopropyl alcohol or the like at a temperature between 0-50° C.

The compound of formula (xxi) can be prepared from compound of formula (xx) using the conditions known to a skilled person for the conversion of carboxylic acids to esters.

The compound of formula (xxi) can be deprotected under acidic conditions to obtain compound of formula (xxii), which can be treated with a reducing agent to obtain compound of formula (xxiii). The compound of formula (xxiii) can be treated with aryl sulphonyl chloride to obtain compound of formula (xxiv), which can be then treated with compound of formula III to afford compound of formula (xiv) where all symbols are the same as described under formula I. Alternatively the compound of formula (xiv) can be prepared by reacting compound of formula (xxii) with compound of formula III under reductive amination conditions known in literature.

The compound of formula (xv) can be prepared either by hydrolysis or hydrogenolysis of compound of formula (xiv) according to conditions generally used by a skilled person for converting esters to carboxylic acids.

Scheme 7 shows an alternative method of preparation of compound of formula (xvii):

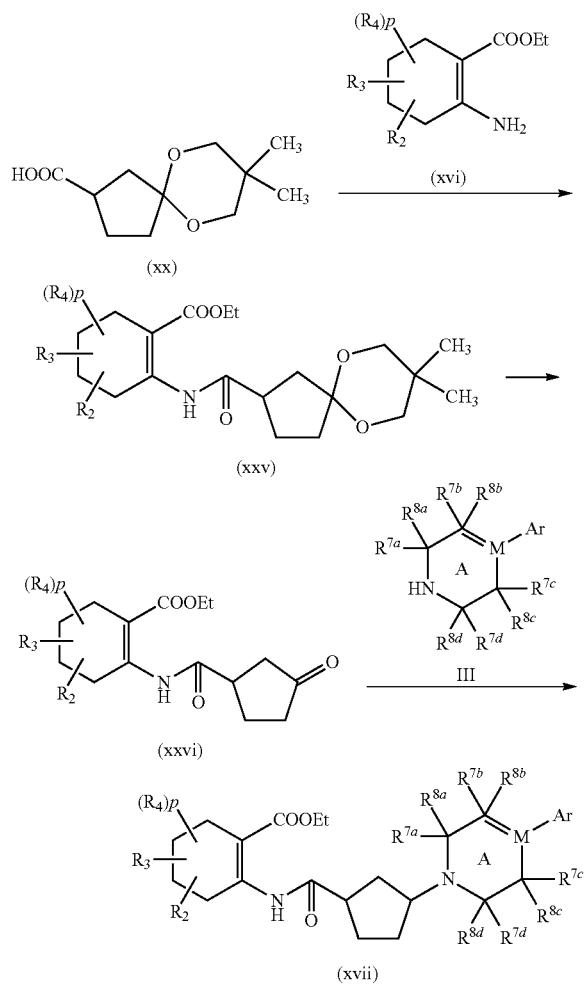

The compound of formula (xx) can be reacted with compound of formula (xvi) as described for the synthesis of compound of formula (xvii) in Scheme 5 to obtain compound of formula (xxv). Compound of formula (xxv) was subjected to deprotection reaction under acidic condition to obtain compound of formula (xxvi), which was then treated with compound of formula III under reductive amination to afford compound of formula (xvii).

The intermediates and the compounds of the present invention can be obtained in a pure form in a manner known per se, for example, by distilling off the solvent in vacuum and/or re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g. flash chromatography) on a suitable support material such as alumina or silica gel using an eluent such as dichloromethane, ethyl acetate, hexane, methanol, acetone and their combinations. Preparative LC-MS method can also be used for the purification of molecules described herein.

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using a mobile phase with suitable polarity.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al., "Pharmaceutical Salts, a review article in Journal of Pharmaceutical sciences volume 66, page 1-19 (1977)" and in "*Handbook of Pharmaceutical Salts—Properties, Selection, and Use*," by P. H. Einrich Stahland Camille G. wermuth, Wiley-VCH (2002). Lists of suitable salts can also be found in *Remington's Pharmaceutical Sciences*, 18th ed., Mack Publishing Company, Easton, Pa., 1990, p. 1445, and *Journal of Pharmaceutical Science*, 66, 2-19 (1977). For example, the salt can be of an alkali metal (e.g., sodium or potassium), alkaline earth metal (e.g., calcium), or ammonium.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of racemic compound using an optically active amine, acid or complex forming agent, and separating the diastereomeric salt/complex by fractional crystallization or by column chromatography.

The compounds of formula I of the present invention can exist in tautomeric forms, such as keto-enol tautomers. Such tautomeric forms are contemplated as an aspect of the present invention and such tautomers may be in equilibrium or predominant in one of the forms.

Thus the present invention further provides a pharmaceutical composition, containing the compounds of the general formula (I) as defined above, its tautomeric forms, its stereoisomers, its pharmaceutically acceptable salts in combination with the usual pharmaceutically acceptable carriers, diluents, excipients, and the like.

The pharmaceutically acceptable carrier or excipient is preferably one that is chemically inert to the compound of the invention and one that has no detrimental side effects or toxicity under the conditions of use. Such pharmaceutically acceptable carriers or excipients include saline (e.g., 0.9% saline), Cremophor EL® (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, intrathecal, intraperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as about 20% to about 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the afore described pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 μg to about 50 mg of at least one compound of the invention per kg body weight of the individual. For a 70 kg patient, dosages of from about 10 μg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

PARP inhibitors reported herein can be used for the treatment of diseases and/or disorders that include but are not limited to cancer, stroke, traumatic brain injury, Parkinson's disease, meningitis, myocardial infarction, ischaemic cardiomyopathy, vascular disease, septic shock, ischemic injury, reperfusion injury, neurotoxicity, inflammatory disease, and haemorrhagic shock. PARP inhibitors mentioned herein can be used as single agents and/or in combination with other chemotherapeutic agents so that they can potentiate the effects of the standard chemotherapeutic agents.

Cancers that can be treated with PARP inhibitors include but are not, limited to breast cancer, glioblastoma, pancreatic cancer, ovarian cancer, prostate cancer, melanoma, colon cancer, leukaemia and lymphoma.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

The terms "effective amount" or "therapeutically effective amount," as used herein, refer to a sufficient amount of an agent or a compound being administered which will relieve to some extent one or more of the symptoms of the disease or condition being treated. In some embodiments, the result is a reduction and! or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. In some embodiments, an appropriate "effective" amount in any individual case is determined using techniques, such as a dose escalation study.

The terms "potentiation" or "potentiating," as used herein, means to increase or prolong either in potency or duration a desired effect. Thus, in regard to potentiating the effect of therapeutic agents/regimen, the term "potentiating" refers to the ability to increase or prolong, either in potency or duration, the effect of other therapeutic agents on a system.

In accordance with the invention, the term subject includes an "animal" which in turn includes a mammal such as, without limitation, the order Rodentia, such as mice, and the order Lagomorpha, such as rabbits. In one aspect, the mammals are from the order Carnivora, including Felines (cats) and Canines (dogs). In another aspect, the mammals are from the order Artiodactyla, including Bovines (cows) and Swine (pigs) or of the order Perssodactyla, including Equines (horses). In a further aspect, the mammals are of the order Primates, Ceboids, or Simoids (monkeys) or of the order Anthropoids (humans and apes). In yet another aspect, the mammal is human.

The term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

Another aspect of the present invention is a pharmaceutical composition of compound of formula I in combination with at least one other known anticancer agent, or a pharmaceutically acceptable salt of said agent.

The said known anticancer agent used in combination may be selected from the group comprising of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide or lenalidomide.

Other aspect of the present invention is provision of a method of treatment or prevention of a disorder responsive to the inhibition of PARP activity in a mammal suffering therefrom, comprising administering to the mammal in need of such treatment a therapeutically effective amount of a compound of formula I.

The said disorder as stated above is cancer, which includes liver cancer, melanoma, Hodgkin's disease, non-Hodgkin's lymphomas, acute or chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, chorio carcinoma, mycosis fungo ide, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma.

Another aspect of the present invention is provision of a method of potentiating the efficacy of chemotherapeutic regimen for a patient undergoing chemotherapeutic treatment comprising co-administering to the patient an effective amount of a compound of the present invention, wherein, the compound of the invention may be co-administered simultaneously, sequentially, or cyclically with the anticancer agent.

The chemotherapeutic agent as mentioned above is selected form busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, panitumumab, ofatumumab, bevacizumab, trastuzumab, adalimumab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide or lenalidomide.

Yet another aspect of the present invention is provision of a method for sensitizing a patient who has developed or likely to develop resistance for chemotherapic agents comprising administering an effective amount of a compound of the present invention.

The following abbreviations are used in the text: DMSO-$d_6$: Hexadeuterodimethyl sulfoxide; DMF: N,N-dimethyl formamide, THF: Tetrahydrofuran, J: Coupling constant in units of Hz, EDCI: 1-ethyl-3-(3-dimethylaminopropyl)carbodiimide, DCC: N,N'-dicyclohexylcarbodiimide, HOBt: Hydroxybenzotriazole, HOAt: 1-Hydroxy-7-azabenzotriazole.

Following examples illustrate demonstrate method of preparation of compounds embodied in formula I; however, the examples should not be constructed as limiting in any way the scope of the invention.

EXAMPLE 1

Synthesis of 2'-(3-(4-(4-chlorophenyl)piperazin-1-yl)propyl)-7',8'-dihydro-3'H-spiro[cyclopropane-1,6'-quinazolin]-4'(5'H)-one (Compound 6)

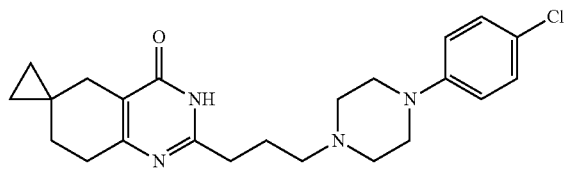 [SMILES: O=c1[nH]c(CCCN2CCN(c3ccc(Cl)cc3)CC2)nc2c1CC1(CC2)CC1]

Step 1: Ethyl 6-oxospiro[2.5]octane-5-carboxylate

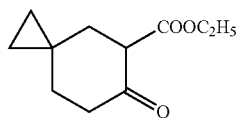

To a stirred solution of spiro[2.5]octan-6-one (prepared according to the procedure reported in US2008176926) (0.900 g, 7.25 mmol) in dimethylformamide (10 ml) at 5° C. was added sodium hydride (0.580 g, 60%, 14.50 mmol) under a nitrogen atmosphere over a period of 10 min and the resulting mixture was stirred for an additional 20 min at the same temperature. To this reaction mixture, diethylcarbonate (1.72 g, 14.50 mmol) was added at 5° C. and stirred for 1 h and then allowed to stir at room temperature for 2 h. The progress of the reaction was monitored by TLC. The reaction mixture was cooled to 0° C. and quenched with saturated ammonium chloride (10 ml) and diluted with water (30 ml). The resulting mixture was extracted with diethyl ether (2×20 ml), and the combined organic layer was washed with water (2×20 ml), dried over anhydrous sodium sulphate, filtered, and the solvent was removed under reduced pressure to obtain a crude product which was purified by flash chromatography over silica gel (100-200 mesh) using 1% ethyl acetate in hexane as eluent to yield the title compound (0.510 g, 35.9%).

$^1$H NMR (400 MHz, CDCl$_3$): δ 12.28 (brs, 1H, D$_2$O exchangeable), 4.22 (q, J=7.0 Hz, 2H), 2.38 (t, J=6.4 Hz, 2H), 2.09 (s, 2H), 1.46 (t, J=6.2 Hz, 2H), 1.29 (t, J=7.2 Hz, 3H), 0.31-0.29 (m, 4H)

The compounds given below were prepared by a process similar to Step 1 above with appropriate variation of reactant, reaction conditions and quantities of reagents:

Ethyl 4-oxospiro[2.5]octane-5-carboxylate $^1$H NMR (400 MHz, CDCl$_3$) δ 12.52 (bs, 1H, D$_2$O exchangeable), 4.26-4.16 (m, 2H), 2.29-2.19 (m, 2H), 1.63-1.61 (m, 2H), 1.48-1.34 (m, 1H), 1.34-1.28 (m, 3H), 1.13-1.11 (m, 1H), 0.65-0.59 (m, 4H)

Ethyl 5-oxospiro[2.5]octane-6-carboxylate $^1$H NMR (400 MHz, CDCl$_3$) δ 12.30 (bs, 1H, D$_2$O exchangeable), 4.26-4.17 (m, 2H), 2.32 (t, J=6.4 Hz, 2H), 2.16 (s, 2H), 1.40 (t, J=6.4 Hz, 2H), 1.34 (t, J=7.2 Hz, 3H), 0.37 (s, 4H).

Ethyl 4-oxobicyclo[4.1.0]heptane-3-carboxylate and ethyl 3-oxobicyclo[4.1.0]heptane-2-carboxylate $^1$H NMR (400 MHz, CDCl$_3$) δ 12.30 (bs, 1H, D$_2$O exchangeable), 12.11 (bs, 1H, D$_2$O exchangeable), 4.32-4.19 (m, 2H), 2.52-2.45 (m, 4H), 2.30-2.20 m, 1H), 2.10-1.91 (m, 3H), 1.70-1.61 (m, 1H), 1.37-1.26 (m, 3H), 1.29-1.26 (m, 1H), 1.15-1.05 (m, 2H), 0.80-0.75 (m, 1H), 0.60-0.50 (m, 1H), 0.37-0.34 (m, 1H), 0.30-0.25 (m, 1H)

Step 2: 4-(4-(4-chlorophenyl)piperazin-1-yl)butanenitrile

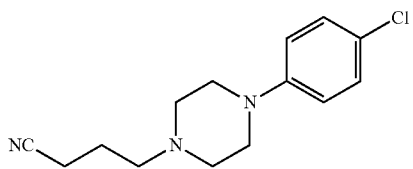 [SMILES: N#CCCCN1CCN(c2ccc(Cl)cc2)CC1]

To a solution of 4-bromobutanenitrile (1.50 g, 10.17 mmol) in dimethyl formamide (20 ml) were added 1-(4-chlorophenyl)piperazine (2.0 g, 10.17 mmol) and potassium carbonate (2.81 g, 20.34 mmol) at room temperature and the reaction mixture was stirred for 3 h at same temperature. The progress of the reaction was monitored by TLC. The reaction mixture was diluted with water (50 ml) and the aqueous layer was extracted with ethyl acetate (3×50 ml). The combined organic layer was dried over anhydrous sodium sulphate. The solvent in the organic layer was removed under reduced pressure to obtain a crude product, which was purified by column chromatography over silica gel (100-200 mesh) using 10% ethyl acetate in hexane to yield the title compound (2.32 g, 86% yield).

$^1$H NMR (400 MHz, CDCl$_3$): δ 7.22 (d, J=8.8 Hz, 2H), 6.85 (d, J=9.2 Hz, 2H), 3.17 (t, J=4.8 Hz, 4H), 2.62 (t, J=5.2 Hz, 4H), 2.43-2.55 (m, 4H), 1.87 (quin, J=6.8 Hz, 2H)

MS: m/z 264.1 (M+1)

Step 3: 4-(4-(4-chlorophenyl)piperazin-1-yl)butanimidamide.

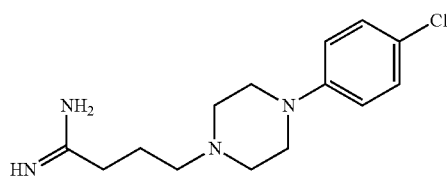 [SMILES: N=C(N)CCCN1CCN(c2ccc(Cl)cc2)CC1]

Trimethylaluminium (2M solution in toluene, 12.32 ml, 24.64 mmol) was added dropwise to a suspension of ammonium chloride (1.32 g, 24.64 mmol) in dry toluene (20 ml) over a period of 20 min at 0° C. under nitrogen atmosphere. The resulting mixture was allowed to stir for 15 min at room temperature. To this was added dropwise a solution of 4-(4-(4-chlorophenyl) piperazin-1-yl)butanenitrile (1.3 g, 4.93 mmol) in dry toluene (10 ml) over a period of 10 min and the reaction mixture was heated at about 90° C. - about 100° C. for 15 h under stirring. The reaction mixture was cooled to 25° C., slowly poured into a slurry of silica gel (100-200 mesh, 30 g) in chloroform (100 ml) and was stirred for 10 min. The silica was filtered through celite and washed with methanol (3 ×50 ml). Combined filtrate was evaporated to obtain a crude solid which was dissolved in 10% hydrochloric acid (100 ml) and washed with diethyl ether (2 x 25 ml). To the resulting aqueous layer was added saturated aqueous solution of sodium hydroxide (30 ml) to bring the pH between 13 and 14. The aqueous layer was extracted with chloroform (3 ×100 ml). The combined organic layer was dried over anhydrous sodium sulphate. The solvent in the organic was evaporated under reduced pressure to obtain the title compound (1.1 g, 79% yield).

$^1$H NMR (400 MHz, CDCl$_3$): δ 7.22 (d, J=8.8 Hz, 2H), 6.85 (d, J=9.2 Hz, 2H), 5.95 (brs, 3H, D$_2$O exchangeable), 3.17 (t, J=4.8 Hz, 4H), 2.62 (t, J=5.2 Hz, 4H), 2.49 (t, J=6.8 Hz, 2H), 2.37 (t, J=6.8 Hz, 2H), 1.85 (quin, J=6.8 Hz, 2H)

MS: m/z 281.0 and 283.0 (M+1 and M+3)

Step 4: 2'-(3-(4-(4-chlorophenyl)piperazin-1-yl)propyl)-7',8'-dihydro-3'H-spiro[cyclopropane-1,6'-quinazolin]-4'(5'H)-one (Compound 6)

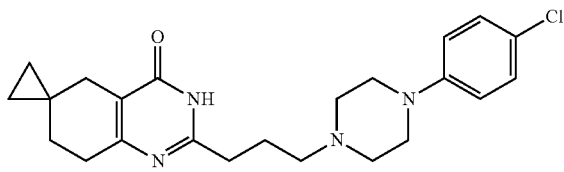 [SMILES: O=c1[nH]c(CCCN2CCN(c3ccc(Cl)cc3)CC2)nc2c1CC1(CC2)CC1]

Sodium (0.094 g, 4.08 mmol) was added to ethanol (15 ml) under stirring condition at room temperature. The resulting mixture was stirred for 30 min. To this freshly prepared clear solution of sodium ethoxide, were added ethyl 6-oxospiro [2.5]octane-5-carboxylate (0.4 g, 2.03 mmol) and 4-(4-(4-chlorophenyl) piperazin-1-yl)butanimidamide (0.343 g, 1.223 mmol) and the reaction mixture was heated at 85° C. for 18 h. The progress of the reaction was monitored by TLC. The reaction mixture was cooled to room temperature and concentrated under reduced pressure to obtain crude residue which was dissolved with water (15 ml). Aqueous layer was extracted with ethylacetate (2×30 ml). The combined organic layer was dried over sodium sulphate, filtered and solvent was removed under reduced pressure to obtain a crude product which was purified by flash chromatography over silica gel (100-200 mesh) using 3-4% methanol in dichloromethane as eluent to obtain title compound (0.030 g, 4% yield).

$^1$H NMR (400 MHz, CDCl$_3$): δ 13.16 (brs, 1H, D$_2$O exchangeable), 7.21 (dd, J=8.8 Hz, 2H), 6.87 (dd, J=8.4 Hz & 2.0 Hz, 2H), 3.39 (t, J=4.8 Hz, 4H), 2.82 (t, J=6 Hz, 2H), 2.74 (t, J=4.8 Hz, 4H), 2.68 (t, J=6.0 Hz, 2H), 2.58 (t, J=5.6 Hz, 2H), 2.34 (s, 2H), 1.96 (t, J=6. Hz, 2H), 1.63-1.56 (m, 2H), 0.35-0.44 (m, 4H).

MS: m/z 412.8 & 414.8 (M+1 & M+3)

The following compounds were prepared using the procedure described above in example 1 with appropriate changes in the reactants and reaction conditions.

2'-(3-(4-(4-fluorophenyl)piperazin-1-yl)propyl)-6',7'-dihydro-3'H-spiro[cyclopropane-1,8'-quinazolin]-4' (5'H)-one (Compound 1)

$^1$H NMR (400 MHz, CDCl$_3$): δ 12.59 (brs, 1H, D$_2$O exchangeable), 6.99-6.89 (m, 4H), 3.35 (brs, 4H), 2.84 (brs, 4H), 2.72 (t J=6.0 Hz, 4H), 2.61 (t, J=6.0 Hz, 2H) 2.03 (brs, 2H), 1.87-1.77 (m, 2H), 1.70-1.63 (brs, 2H), 1.37-1.29 (m, 2H), 0.69-0.72 (m, 2H).

MS: m/z 396.9 (M+1).

2'-(3-(4-(4-chlorophenyl)piperazin-1-yl)propyl)-6',7'-dihydro-3'H-spiro[cyclopropane-1,8'-quinazolin]-4' (5'H)-one (Compound 2)

$^1$H NMR (400 MHz, CDCl$_3$): δ 12.63 (brs, 1H, D$_2$O exchangeable), 7.21 (d, J=7.8 Hz, 2H), 6.86 (d, J=7.0 Hz, 2H), 3.34 (brs, 4H), 2.57-2.71 (m, 10H), 1.95 (brs, 2H), 1.84-1.74 (m, 2H), 1.69-1.67 (m, 2H), 1.36-1.24 (m, 2H), 0.70-0.69 (m, 2H).

MS: m/z 413 (M+1) & 415 (M+1).

2'-(3-(4-phenyl-5,6-dihydropyridin-1(2H)-yl)propyl)-6',7'-dihydro-3'H-spiro[cyclopropane-1,8'-quinazolin]-4'(5'H)-one. (Compound 3)

$^1$H NMR (400 MHz, CDCl$_3$): δ 11.96 (brs, 1H, D$_2$O exchangeable), 7.44-7.42 (m, 2H), 7.35-7.31 (m, 2H), 7.26-7.24 (m, 1H), 6.07 (brs, 1H), 3.23-3.22 (m, 2H), 2.79 (t, J=5.2 Hz, 2H), 2.71 (brs, 2H), 2.66 (t, J=6.4 Hz, 2H), 2.63-2.55 (m, 4H), 1.98-1.93 (m, 2H), 1.78-9.1 (m, 2H), 1.69-1.66 (m, 2H), 1.35-1.32 (m, 2H), 0.71-0.68 (m, 2H).

MS: m/z 376 (M+1).

2'-(3-(3-(4-fluorophenyl)-3,8-diazabicyclo[3.2.1] octan-8-yl)propyl)-4a',5',6',7'-tetrahydro-3'H-spiro [cyclopropane-1,8'-quinazolin]-4'(8a'H)-one. (Compound 4)

$^1$H NMR (400 MHz, CDCl$_3$): δ 12.65 (brs, 1H, D$_2$O exchangeable), 6.91-6.90 (m, 2H), 6.78-6.74 (m, 2H), 4.12 (brs, 2H), 3.38-3.27 (m, 2H), 3.26-3.16 (m, 2H), 2.73-2.58 (m, 2H), 2.57-2.52 (m, 4H), 2.06-2.00 (m, 2H), 1.91-1.65 (m, 10H), 1.34-1.32 (m, 2H), 0.75-0.70 (m, 2H).

MS: m/z 424 (M+1).

2'-(3-(4-(4-fluorophenyl)piperazin-1-yl)propyl)-7',8'-dihydro-3'H-spiro[cyclopropane-1,6'-quinazolin]-4' (5'H)-one. (Compound 5)

$^1$H NMR (400 MHz, CDCl$_3$): δ 13.26 (brs, 1H, D$_2$O exchangeable), 7.00-6.90 (m, 4H), 3.32 (t, J=5.0 Hz, 4H), 2.83-2.57 (m, 10H), 2.35 (s, 2H), 1.99-193 (m, 2H), 1.58 (t, J=5.8 Hz, 2H), 0.44-0.38 (m, 4H).

MS: m/z 397 (M+1).

2'-(3-(3-(4-fluorophenyl)-3,8-diazabicyclo[3.2.1] octan-8-yl)propyl)-7',8'-dihydro-3'H-spiro[cyclopropane-1,6'-quinazolin]-4'(5'H)-one. (Compound 7)

$^1$H NMR (400 MHz, CDCl$_3$): δ 13.26 (brs, 1H, D$_2$O exchangeable), 6.96-6.92 (m, 2H), 6.80-6.76 (m, 2H), 3.30 (brs, 4H), 2.87-2.60 (m, 6H), 2.33 (s, 2H), 2.07-1.57 (m, 8H), 0.89-0.87 (m, 2H), 0.41-0.39 (m, 4H).

MS: m/z 423.2 (M+1).

2'-(3-(8-(4-fluorophenyl)-3,8-diazabicyclo[3.2.1] octan-3-yl)propyl)-7',8'-dihydro-3'H-spiro[cyclopropane-1,6'-quinazolin]-4'(5'H)-one. (Compound 8)

$^1$H NMR (400 MHz, CDCl$_3$): δ 13.26 (brs, 1H, D$_2$O exchangeable), 6.94-6.98 (m, 2H), 6.71-6.76 (2H, m), 4.16 (brs, 2H), 2.69 (brs, 6H), 2.56 (brs, 2H), 2.37 (s, 4H), 2.18 (brs, 2H), 2.06 (brs, 2H), 1.93 (brs, 2H), 1.60 (t, J=6.4 Hz, 2H), 0.47-0.41 (m, 4H).

MS: m/z 422.9 (M+1).

2'-(3-(4-(4-fluorophenyl)-5,6-dihydropyridin-1(2H)-yl)propyl)-7',8'-dihydro-3'H-spiro[cyclopropane-1,6'-quinazolin]-4'(5'H)-one. (Compound 9)

$^1$H NMR (400 MHz, DMSO-d$_6$): δ 12.18 (brs, 1H, D$_2$O exchangeable), 7.42-7.46 (m, 2H), 7.12-7.16 (m, 2H), 6.09

(brs, 1H), 3.04 (brs, 2H), 2.60-2.48 (m, 8H), 2.14 (s, 2H), 1.88-1.81 (m, 2H), 1.47 (t, J=6.4 Hz, 2H), 1.24 (brs, 2H), 0.36-0.29 (m, 4H).

MS: m/z 394 (M+1).

2'-(3-(4-(3,4-dichlorophenyl)piperazin-1-yl)propyl)-7',8'-dihydro-3'H-spiro[cyclopropane-1,6'-quinazolin]-4'(5'H)-one. (Compound 10)

$^1$H NMR (400 MHz, DMSO-d$_6$): δ 12.22 (brs, 1H, D$_2$O exchangeable), 7.37 (d, J=8.8 Hz, 1H), 7.08 (d, J=2.8 Hz, 1H), 6.90 (dd, J=2.8 Hz & 8.8 Hz, 1H), 3.09 (brs, 4H), 2.55-2.43 (m, 8H), 2.35 (t, J=6.4 Hz, 2H), 2.14 (brs, 2H), 1.85-1.80 (m, 2H), 1.48 (t, J=6.4 Hz, 2H), 0.36-0.23 (m, 4H).

MS: m/z 446.9 (M+1) & 448.9 (M+3).

2'-(3-(5-(4-fluorophenyl)-2,5-diazabicyclo[2.2.1]heptan-2-yl)propyl)-7',8'-dihydro-3'H-spiro[cyclopropane-1,6'-quinazolin]-4'(5'H)-one. (Compound 11)

$^1$H NMR (400 MHz, DMSO-d$_6$): δ 12.22 (brs, 1H, D$_2$O exchangeable), 6.94 (t. J=9.2 Hz, 2H), 6.48-6.51 (m, 2H), 4.17 (brs, 1H), 3.50 (brs, 1H), 3.25 (d, J=7.2 Hz, 1H), 3.04 (d, J=9.2 Hz, 1H), 2.80 (d, J=8.0 Hz, 1H), 2.50-2.34 (m, 7H), 2.14 (brs, 2H), 1.85-1.63 (m, 4H), 1.43 (t, J=6.0 Hz, 2H), 0.35-0.29 (m, 4H).

MS: m/z 408.9 (M+1).

2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one. (Compound 12)

$^1$H NMR (400 MHz, CDCl$_3$): δ 6.97-6.92 (m, 2H), 6.80-6.76 (m, 2H), 3.45 (brs, 2H), 3.30 (s, 4H), 2.87-2.60 (m, 6H), 2.33 (s, 2H), 2.07-1.87 (m, 6H), 0.89-0.87 (m, 2H) 0.41-0.39 (m, 4H).

MS: m/z 423 (M+1).

2'-(3-(4-phenylpiperazin-1-yl)propyl)-7',8'-dihydro-3'H-spiro[cyclopropane-1,6'-quinazolin]-4'(5'H)-one. (Compound 13)

$^1$H NMR (400 MHz, DMSO-d$_6$): δ 12.22 (brs, 1H, D$_2$O exchangeable), 7.21-7.14 (m, 2H), 6.89 (d, J=8.0 Hz, 2H), 6.77-6.73 (m, 1H), 3.05 (t, J=4.8 Hz, 4H), 2.55-2.45 (m, 8H), 2.36 (t, J=6.4 Hz, 2H), 2.14 (brs, 2H), 1.85-1.81 (m, 2H), 1.48 (t, J=6.4 Hz, 2H), 0.35-0.28 (m, 4H).

MS: m/z 379 (M+1).

2'-(3-(4-(2-chlorophenyl)piperazin-1-yl)propyl)-7',8'-dihydro-3'H-spiro[cyclopropane-1,6'-quinazolin]-4'(5'H)-one. (Compound 14)

$^1$H NMR (400 MHz, DMSO-d$_6$): δ 12.24 (brs, 1H, D$_2$O exchangeable), 7.39 (dd, J=1.6 Hz & 8.0 Hz, 1H), 7.31-7.26 (m, 1H), 7.10 (dd, J=1.6 Hz & 8.4 Hz, 1H), 7.00-7.06 (m, 1H), 2.90 (brs, 4H), 2.55-2.49 (m, 8H), 2.38 (t, J=6.4 Hz, 2H), 2.17 (brs, 2H), 1.84-1.80 (m, 2H), 1.48 (t, J=6.4 Hz, 2H), 0.36-0.29 (m, 4H).

MS: m/z 413 (M+1).

2'-(3-(4-(4-fluorophenyl)piperazin-1-yl)propyl)-5',6'-dihydro-3'H-spiro[cyclopropane-1,7'-quinazolin]-4'(8'H)-one. (Compound 15)

$^1$H NMR (400 MHz, CDCl$_3$): δ 12.24 (brs, 1H, D$_2$O exchangeable), 6.99-6.90 (m, 4H), 3.36 (m, 4H), 2.83-2.78 (m, 6H), 2.66 (brs, 2H), 2.56 (t, J=6.0 Hz, 2H), 2.46 (s, 2H), 2.01 (brs, 2H), 1.52 (t, J=6.0 Hz, 2H), 0.49-0.41 (m, 4H).

MS: m/z 397 (M+1).

2'-(3-(4-(4-fluorophenyl)-5,6-dihydropyridin-1(2H)-yl)propyl)-5',6'-dihydro-3'H-spiro[cyclopropane-1,7'-quinazolin]-4'(8'H)-one. (Compound 16)

$^1$H NMR (400 MHz, CDCl$_3$): δ 7.36-7.41 (m, 2H), 7.00-7.06 (m, 2H), 6.00 (brs, 1H), 3.48 (brs, 2H), 3.03 (brs, 2H), 2.92-2.76 (m, 6H), 2.56 (t. J=6.0 Hz, 2H), 2.46 (brs, 2H), 2.13 (brs, 2H), 1.51 (t, J=6.4 Hz, 2H) 0.43 (brs, 4H).

MS: m/z 393.9 (M+1).

2'-(3-(4-phenyl-5,6-dihydropyridin-1(2H)-yl)propyl)-5',6'-dihydro-3'H-spiro[cyclopropane-1,7'-quinazolin]-4'(8'H)-one. (Compound 17)

$^1$H NMR (400 MHz, CDCl$_3$): δ 7.42-7.44 (m, 2H), 7.32-7.36 (m, 2H), 7.29-7.25 (m, 1H), 6.07 (s, 1H), 3.44 (brs, 2H), 3.01 (brs, 2H), 2.82-2.75 (m, 6H), 2.57 (t, J=6.4 Hz, 2H), 2.46 (brs, 2H), 2.12-2.09 (m, 2H), 1.50 (t, J=6.4 Hz, 2H), 0.40 (brs, 4H).

MS: m/z 376 (M+1).

2'-(3-(4-(3-chlorophenyl)piperazin-1-yl)propyl)-7',8'-dihydro-3'H-spiro[cyclopropane-1,6'-quinazolin]-4'(5'H)-one. (Compound 18)

$^1$H NMR (400 MHz, DMSO-d$_6$): δ 12.22 (brs, 1H, D$_2$O exchangeable), 7.21-7.12 (m, 1H), 6.90-6.85 (m, 2H), 6.77-6.75 (m, 1H), 3.07-3.09 (m, 4H), 2.55-2.43 (m, 8H), 2.35 (t, J=6.8 Hz, 2H), 2.15 (s, 2H), 1.82 (t, J=6.8 Hz, 2H), 1.48 (t, J=6.0 Hz, 2H) 0.36-0.28 (m, 4H).

MS: m/z 413 (M+1).

2'-(3-(4-phenylpiperidin-1-yl)propyl)-7',8'-dihydro-3'H-spiro[cyclopropane-1,6'-quinazolin]-4'(5'H)-one. (Compound 19)

$^1$H NMR (400 MHz, DMSO-d$_6$): δ 12.45 (brs, 1H, D$_2$O exchangeable), 7.29-7.15 (m, 5H), 2.95-2.92 (m, 2H), 2.54-2.39 (m, 5H), 2.36-2.33 (m, 2H), 2.19 (brs, 2H), 1.96-1.80 (m, 4H), 1.67-1.56 (m, 4H), 1.47 (t, J=6.0 Hz, 2H), 0.35-0.29 (m, 4H).

MS: m/z 378.1 (M+1).

2'-(3-(4-(pyridin-2-yl)piperazin-1-yl)propyl)-7',8'-dihydro-3'H-spiro[cyclopropane-1,6'-quinazolin]-4'(5'H)-one. (Compound 20)

$^1$H NMR (400 MHz, DMSO-d$_6$): δ 12.24 (brs, 1H, D$_2$O exchangeable), 8.08 (dd, J=1.6 Hz & 5.2 Hz, 1H), 7.53-7.48 (m, 1H), 6.78 (d, J=8.8 Hz, 1H), 6.63-6.60 (m, 1H), 3.40-3.37 (m, 4H), 2.56-2.39 (m, 8H), 2.37-2.33 (t, J=6.4 Hz, 2H), 2.15 (brs, 2H), 1.86-1.79 (m, 2H), 1.50-1.47 (t, J=5.6 Hz, 2H), 0.36-0.28 (m, 4H).

MS: m/z 380 (M+1).

2'-(3-(4-(4-fluorophenyl)piperazin-1-yl)butyl)-7',8'-dihydro-3'H-spiro[cyclopropane-1,6'-quinazolin]-4'(5'H)-one. (Compound 21)

$^1$H NMR (400 MHz, CDCl$_3$): δ 12.66 (brs, 1H, D$_2$O exchangeable), 6.98-6.89 (m, 4H), 3.36-3.22 (m, 4H), 2.86-2.67 (m, 9H), 2.34 (brs, 2H), 1.99-1.79 (m, 2H), 1.57 (t, J=6.0 Hz, 2H), 1.08 (d, J=6.4 Hz, 3H), 0.40 (brs, 4H).

MS: m/z 411 (M+1).

2'-(3-(4-(3-(trifluoromethyl)phenyl)piperazin-1-yl)propyl)-7',8'-dihydro-3'H-spiro[cyclopropane-1,6'-quinazolin]-4'(5'H)-one. (Compound 22)

¹H NMR (400 MHz, CDCl₃): δ 7.38-7.34 (m, 1H), 7.14-7.08 (m, 3H), 3.51 (brs, 4H), 2.88-2.85 (m, 6H), 2.71-2.66 (m, 4H), 2.34 (brs, 2H), 2.06 (brs, 2H), 1.58 (t, J=6.4 Hz, 2H), 0.44-0.40 (m, 4H).
MS: m/z 447 (M+1).

2'-(3-(4-(m-tolyl)piperazin-1-yl)propyl)-7',8'-dihydro-3'H-spiro[cyclopropane-1,6'-quinazolin]-4'(5'H)-one. (Compound 23)

¹H NMR (400 MHz, DMSO-d₆): δ 12.21 (brs, 1H, D₂O exchangeable), 7.07 (dd, J=7.6 Hz & 7.6 Hz, 1H), 6.71-6.68 (m, 2H), 6.58 (d, J=7.6 Hz, 1H), 3.03 (brs, 4H), 2.56-2.44 (m, 8H), 2.34 (t, J=6.4 Hz, 2H), 2.23 (s, 3H), 2.15 (brs, 2H), 1.83 (t, J=7.2 Hz, 2H), 1.48 (t, J=6.4 Hz, 2H), 0.36-0.29 (m, 4H).
MS: m/z 393 (M+1).

2-(3-(4-(4-fluorophenyl)piperazin-1-yl)propyl)-5a,6,6a,7-tetrahydro-3H-cyclopropa[g]quinazolin-4(5H)-one. (Compound 24)

¹H NMR (400 MHz, CDCl₃): δ 13.27 (brs, 1H, D₂O exchangeable), 6.98-6.89 (m, 4H), 3.36-3.22 (m, 4H), 2.86-2.67 (m, 9H), 2.34 (brs, 2H), 1.99-1.79 (m, 2H), 1.52-1.30 (m, 5H)
MS: m/z 383 (M+1).

2-(3-(4-phenylpiperazin-1-yl)propyl)-5a,6,6a,7-tetrahydro-3H-cyclopropa[g]quinazolin-4(5H)-one. (Compound 25)

¹H NMR (400 MHz, CDCl₃): δ 7.29.7.26 (m, 2H), 6.98-6.87 (m, 3H), 3.45-3.44 (m, 4H), 3.08-2.52 (m, 10H), 2.45-2.00 (m 4H), 2.06 (brs, 2H), 1.05-0.55 (m, 2H).
MS: m/z 365 (M+1).

2'-(3-(4-(4-fluorophenyl)-2,6-dimethylpiperazin-1-yl)propyl)-7',8'-dihydro-3'H-spiro[cyclopropane-1,6'-quinazolin]-4'(5'H)-one. (Compound 26)

¹H NMR (400 MHz, DMSO-d₆): δ 12.22 (brs, 1H, D₂O exchangeable), 8.12 (d, J=6.0 Hz, 2H), 6.78 (d, J=6.0 Hz, 2H), 3.22 (brs, 4H), 2.50-2.54 (m, 6H), 2.42 (brs, 2H), 2.35 (t, J=6.4 Hz, 2H), 2.14 (brs, 4H), 1.79-1.86 (m, 2H), 1.48 (t, J=6.4 Hz, 2H), 1.23 (brs, 2H), 0.28-0.36 (m, 4H).
MS: m/z 425 (M+1).

2'-(3-(4-(4-fluorophenyl)-2-methylpiperazin-1-yl)propyl)-7',8'-dihydro-3'H-spiro[cyclopropane-1,6'-quinazolin]-4'(5'H)-one. (Compound 27)

¹H NMR (400 MHz, CDCl₃): δ 6.90-6.99 (m, 4H), 3.41 (brs, 4H), 2.80-3.22 (m, 6H), 2.69 (t, J=6.4 Hz, 2H), 2.37 (s, 2H), 2.06 (brs, 2H), 1.58 (t, J=6.0 Hz, 2H), 1.34-1.24 (m, 4H), 0.44-0.38 (m, 4H).
MS: m/z 411.1 (M+1).

2'-(3-(4-(2-fluorophenyl)piperazin-1-yl)propyl)-7',8'-dihydro-3'H-spiro[cyclopropane-1,6'-quinazolin]-4'(5'H)-one. (Compound 28)

¹H NMR (400 MHz, CDCl₃): δ 7.00-6.94 (m, 4H), 3.34 (brs, 4H), 2.95-2.84 (m, 6H), 2.73-2.64 (m, 4H), 2.36 (brs, 2H), 2.00 (brs, 2H), 1.57 (t, J=7.8 Hz, 2H), 0.48-0.38 (m, 4H).
MS: m/z 397 (M+1).

2'-(3-(4-(pyridin-4-yl)piperazin-1-yl)propyl)-7',8'-dihydro-3'H-spiro[cyclopropane-1,6'-quinazolin]-4'(5'H)-one. (Compound 29)

¹H NMR (400 MHz, DMSO-d₆): δ 12.22 (brs, 1H, D₂O exchangeable), 8.12 (d, J=6.0 Hz, 2H), 6.78 (d, J=6.0 Hz, 2H), 3.22 (brs, 4H), 2.54-2.50 (m, 6H), 2.42 (brs, 2H), 2.35 (t, J=6.4 Hz, 2H), 2.14 (brs, 2H), 1.86-1.79 (m, 2H), 1.48 (t, J=6.4 Hz, 2H), 0.36-0.28 (m, 4H).
MS: m/z 380.5 (M+1).

2'-(3-(4-(4-fluorophenyl)piperazin-1-yl)-3-methylbutyl)-7',8'-dihydro-3'H-spiro[cyclopropane-1,6'-quinazolin]-4'(5'H)-one. (Compound 30)

¹H NMR (400 MHz, CDCl₃): δ 13.19 (brs, 1H, D₂O exchangeable), 6.97-6.93 (m, 2H), 6.88-6.85 (m, 2H), 3.13 (brs, 4H), 2.76-2.70 (m, 8H), 2.30 (brs, 2H), 1.94 (brs, 2H), 1.56 (t, J=6.0 Hz, 2H), 1.15 (brs, 6H), 0.36-0.35 (m, 4H).
MS: m/z 425.5 (M+1)

(E)-2'-(3-(4-(4-fluorophenyl)piperazin-1-yl)-3-methylbut-1-en-1-yl)-7',8'-dihydro-3'H-spiro[cyclopropane-1,6'-quinazolin]-4'(5'H)-one. (Compound 31)

¹H NMR (400 MHz, CDCl₃): δ 12.64 (brs, 1H, D₂O exchangeable), 7.13 (d, J=16.8 Hz, 1H), 6.93-7.01 (m, 2H), 6.90-6.85 (m, 2H), 6.33 (d, J=16.8 Hz, 1H), 3.14 (brs, 4H), 2.79-2.72 (m, 6H), 2.40 (s, 2H), 1.59 (t, J=6.4 Hz, 2H), 1.42 (brs, 6H), 0.42-0.36 (m, 4H).
MS: m/z 423(M+1).

2'-(3-(4-(p-tolyl)piperazin-1-yl)propyl)-7',8'-dihydro-3'H-spiro[cyclopropane-1,6'-quinazolin]-4'(5'H)-one. (Compound 32)

¹H NMR (400 MHz, CDCl₃): δ 12.64 (brs, 1H, D₂O exchangeable), 7.06-7.12 (m, 2H), 6.82-6.92 (m, 2H), 3.35 (brs, 4H), 2.63-2.81 (m, 10H), 2.27-2.35 (m, 5H), 2.03 (brs, 2H), 1.48-1.59 (m, 2H), 0.40-0.42 (m, 4H).
MS: m/z 393.1 (M+1).

2'-(3-(4-(4-fluorophenyl)-2-oxopiperazin-1-yl)propyl)-7',8'-dihydro-3'H-spiro[cyclopropane-1,6'-quinazolin]-4'(5'H)-one. (Compound 33)

¹H NMR (400 MHz, DMSO-d₆): δ 12.15 (brs, 1H, D₂O exchangeable), 7.09-7.05 (m, 2H), 6.93-6.92 (m, 2H), 3.68 (s, 2H), 3.44-3.37 (m, 6H), 2.56-2.45 (m, 4H), 2.16 (s, 2H), 1.92-1.87 (m, 2H), 1.47 (t, J=6.4 Hz, 2H), 0.38-0.34 (m, 4H).
MS: m/z 411.6 (M+1).

2'-(3-(4-(2,4-dichlorophenyl)piperazin-1-yl)propyl)-7',8'-dihydro-3'H-spiro[cyclopropane-1,6'-quinazolin]-4'(5'H)-one. (Compound 34)

¹H NMR (400 MHz, CDCl₃): δ 13.61 (brs, 1H, D₂O exchangeable), 7.35 (d, J=2.4 Hz, 1H), 7.20 (dd, J=2.4 Hz & 8.4 Hz, 1H), 7.12 (d, J=8.4 Hz, 1H), 3.29-3.26 (m, 4H), 2.85-2.79 (m, 6H), 2.69 (t, J=6.4 Hz, 2H), 2.62 (t, J=5.6 Hz, 2H), 2.37 (brs, 2H), 1.98-1.93 (m, 2H), 1.59 (t, J=6.4 Hz, 2H), 0.95-0.93 (m, 4H).
MS: m/z 447(M+1) & 449 (M+3).

2-(3-(4-(4-fluorophenyl)piperazin-1-yl)propyl)-5,6,7,8-tetrahydro-5,8-methanoquinazolin-4(3H)-one. (Compound 35)

$^1$H NMR (400 MHz, DMSO-d6): δ 12.23 (brs, 1H, D$_2$O exchangeable), 7.03 (t, J=9.0 Hz, 2H), 6.91 (dd, J=9.2, 4.4 Hz, 2H), 3.26 (s, 1H), 3.09 (s, 1H), 3.00 (s, 4H), 2.56-2.33 (m, 8H), 1.90-1.79 (m, 4H), 1.56 (d, J=8.4 Hz, 1H), 1.32 (d, J=8.4 Hz, 1H), 1.12-1.02 (m, 2H).
MS: m/z 383 (M+1).

2-(3-(4-(4-chlorophenyl)piperazin-1-yl)propyl)-5,6,7,8-tetrahydro-5,8-methanoquinazolin-4(3H)-one. (Compound 36)

$^1$H NMR (400 MHz, CDCl$_3$): δ 12.23 (brs, 1H, D$_2$O exchangeable), 7.20 (dd, J=6.8, 2.0 Hz, 2H), 6.91 (dd, J=6.8, 2.0 Hz, 2H), 3.36 (s, 1H) 3.09 (s, 1H), 3.00 (s, 4H), 2.56-2.33 (m, 8H), 1.90-1.79 (m, 4H), 1.56 (d, J=8.4 Hz, 1H), 1.32 (d, J=8.4 Hz, 1H), 1.12-0.99 (m, 2H).
MS: m/z 399 (M+1).

EXAMPLE 2

Synthesis of 1-(4-fluorophenyl)-3,3-dimethylpiperazine

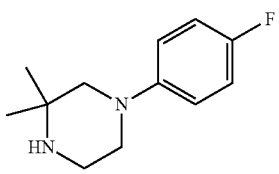

Step 1: 4-benzyl-3,3-dimethylpiperazin-2-one

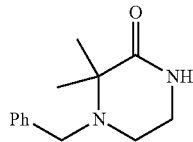

To a stirred solution of 3,3-dimethylpiperazin-2-one (prepared according to procedure reported in WO200516900A1, 6.0 g, 46.8 mmol) in N,N-dimethylformamide (10 ml) was added benzyl bromide (6.68 ml, 56.2 mmol) at 0° C., followed by addition of triethylamine (19.57 ml, 140 mmol). Reaction was stirred for 3 h at 0-25° C. The progress of reaction was monitored by TLC. After completion of reaction, the reaction mixture was diluted with ethyl acetate (100 ml) and water (100 ml). Aqueous layer was extracted with ethyl acetate (50 ml×6). The combined organic phase was washed with brine (50 mL) and dried over sodium sulphate and concentrated under reduced pressure till dryness. Crude compound was adsorbed on 100-200 mesh silica gel and purified by using flash column chromatography method using 5% methanol in dichloromethane as eluent. Title compound was eluted at 5% methanol in dichloromethane (6.2 g, 60.7%).

$^1$H NMR (400 MHz, DMSO-d$_6$) δ 7.62 (bs, 1H, D$_2$O exchangeable), 7.39-7.21 (m, 5H), 3.56 (s, 2H), 3.00-2.97 (m, 2H), 2.50-2.49 (m, 2H), 1.30 (s, 6H).

Step 2: 1-benzyl-2,2-dimethylpiperazine

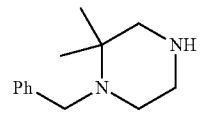

To a stirred solution of lithiulalluminium hydride (1.078 g, 28.4 mmol) in tetrahydrofuran (200 ml) at 0-20° C. was added 4-benzyl-3,3-dimethylpiperazin-2-one (6.2 g, 28.4 mmol in 100 ml tetrahydrofuran) over 1 h. The reaction mixture was warmed to 25° C. over 15 minutes followed by reflux for 6 h. The progress of reaction was monitored by TLC. After completion of reaction, the reaction mixture was cooled to 0-10° C. and 10% sodium hydroxide (50 ml) was added slowly over 1 h. and then allowed to stir for 20 hr at 25° C. The reaction mass was passed through celite and washed with tetrahydrofuran (500 ml). The combined filtrate was concentrated under reduced pressure. Water (100 ml) was added and the aq. phase was extracted with ethyl acetate (3×100 ml). The combined organic layer was washed with brine (50 ml) and dried over sodium sulphate, and concentrated under reduced pressure till dryness. The resulting crude product (5.2 g) was carried over to the next step without purification.

$^1$H NMR (400 MHz, CDCl$_3$) δ 7.37-7.21 (m, 5H), 3.53 (bs, 1H, D$_2$O exchangeable), 3.52 (s, 2H), 2.82-2.80 (m, 2H), 2.69 (s, 2H), 2.37-2.31 (m, 2H), 1.17 (s, 6H).

Step 3: 1-benzyl-4-(4-fluorophenyl)-2,2-dimethylpiperazine

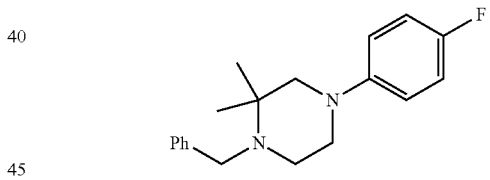

To a stirred solution of 1-benzyl-2,2-dimethylpiperazine (1.2 g, 5.87 mmol) in 1,4-dioxane (50 ml) at 25° C. was added 1-bromo-4-fluorobenzene (1.233 g, 7.05 mmol), 2,2'-Bis (diphenylphosphino)-1,1'-binaphthyl (BINAP) (0.366 g, 0.587 mmol), sodium tert-butoxide (1.129 g, 11.75 mmol), and tris(dibenzyllideneacetone)dipalladium (0) [Pd$_2$(dba)$_3$] (0.269 g, 0.294 mmol). The reaction mixture was purged with nitrogen for 10 min in sealed tube and then heated at 100° C. for 5 h. The progress of reaction was monitored by TLC. The reaction mixture was cooled to 25° C., filtered through celite, washed with ethyl acetate (2×50 ml). The combined filtrate was concentrated under reduced pressure to obtain a crude product. The crude product was purified over silica gel (100-200 mesh) by flash chromatography using 10% ethyl acetate in hexane as eluent to obtain the title compound (1.1 g, 62.8%)

$^1$H NMR (400 MHz, CDCl$_3$) δ 7.40 (d, J=7.2 Hz, 2H), 7.34 (t, J=7.2 Hz, 2H), 7.24 (t, J=7.2 Hz, 1H), 6.99-6.93 (m, 2H), 6.88-6.83 (m, 2H), 3.58 (s, 2H), 3.00 (t, J=5.2 Hz, 2H), 2.92 (s, 2H), 2.59 (t, J=5.2 Hz, 2H), 1.25 (s, 6H).
MS: m/z 299 (M+1).

Step 4: 1-(4-fluorophenyl)-3,3-dimethylpiperazine

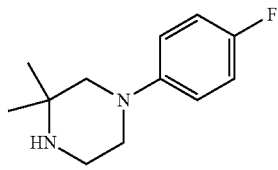

To a stirred solution of 1-benzyl-4-(4-fluorophenyl)-2,2-dimethylpiperazine (4.5 g, 15.08 mmol) in methanol and ethyl acetate (5:1, 60 ml) at 25° C. was added 10% palladium on charcoal (1.605 g). The reaction mixture was stirred at 50° C. for 5 h. The progress of reaction was monitored by TLC. The reaction mixture was cooled to room temperature, filtered through a celite bed, washed with ethyl acetate (2×50 ml). The combined filtrate was concentrated under reduced pressure to obtain the title compound which was used in the next step without further purification.

$^1$H NMR (400 MHz, CDCl$_3$) δ 7.06-7.02 (m, 2H), 6.94-6.91 (m, 2H), 2.98-2.96 (m, 4H), 2.85 (s, 2H), 1.16 (s, 6H).

EXAMPLE 3

Synthesis of 1-(4-fluorophenyl)piperazin-2-one

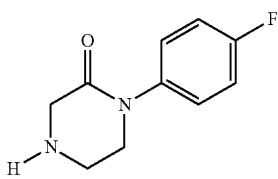 [SMILES: O=C1CNCCN1c1ccc(F)cc1]

Step 1: tert-butyl 4-(4-fluorophenyl)-3-oxopiperazine-1-carboxylate

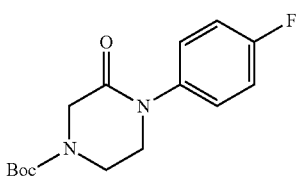 [SMILES: CC(C)(C)OC(=O)N1CCN(c2ccc(F)cc2)C(=O)C1]

To a solution of tert-butyl 3-oxopiperazine-1-carboxylate (prepared according to procedure reported in JP2005504737, 2.0 g, 9.99 mmol), 1-bromo-4-fluorobenzene (1.748 g, 9.99 mmol), N,N-dimethylethylenediamine (0.070 g, 0.799 mmol) and potassium hydrophosphate (KHPO4) (3.13 g, 17.98 mmol) in toluene (10 ml) was added copper (I)iodide (0.101 g, 0.529 mmol) at 25° C. The reaction mixture was heated to 80° C. for 16 h. Progress of the reaction was monitored by TLC. The reaction mixture was cooled to 25° C., diluted with ethyl acetate (25 ml) and filtered through a plug of celite and concentrated to give crude product. The crude product was purified over silica gel (100-200 mesh) by column chromatography using 30% ethyl acetate in hexane as eluent to obtain the title compound (0.8 g, 27.2%).

$^1$H NMR (400 MHz, CDCl$_3$) δ 7.28-7.24 (m, 2H), 7.14-7.08 (m, 2H), 4.26 (s, 2H), 3.88-3.71 (m, 4H), 1.51 (s, 9H).
MS: m/z 295 (M+1).

Step 2: 1-(4-fluorophenyl)piperazin-2-one

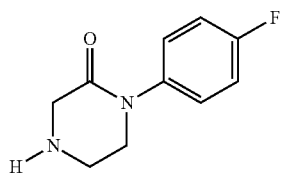 [SMILES: O=C1CNCCN1c1ccc(F)cc1]

To the solution of tert-butyl 4-(4-fluorophenyl)-3-oxopiperazine-1-carboxylate (2 g, 6.80 mmol) in dichloromethane (5 ml) was added slowly hydrogenchloride in 1,4-dioxane (16.99 ml, 68.0 mmol) at 0° C. and reaction was stirred for 3 h at 25° C. After completion of the reaction, the solvent was evaporated under reduced pressure to obtained salt was triturated with diethyl ether (2×10 ml) decanted it and dried to give 1-(4-fluorophenyl)piperazin-2-one hydrochloride (1.2 g, 5.20 mmol, 77%)

$^1$H NMR (400 MHz, DMSO-d$_6$) δ 9.90 (bs, 1H, D$_2$O exchangeable), 7.38-7.34 (m, 4H), 3.85-3.72 (m, 4H), 3.55-3.50 (m, 2H).
MS: m/z 195 (M+1).

EXAMPLE 4

Synthesis of 4-(4-(4-fluorophenyl)piperazin-1-yl)pentanenitrile

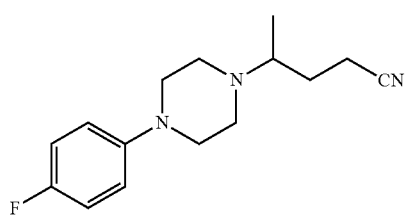

Step 1: 3-(4-(4-fluorophenyl)piperazin-1-yl)butyl methanesulfonate

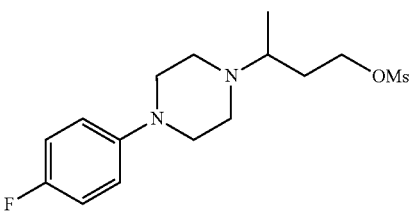 [SMILES: CC(CCOS(C)(=O)=O)N1CCN(c2ccc(F)cc2)CC1]

To a stirred solution of 3-(4-(4-fluorophenyl) piperazin-1-yl) butan-1-ol (prepared according to procedure reported in U.S. Pat. No. 5,021,420, 3.5 g, 13.87 mmol) in dichloromethane (30 ml) was added triethylamine (4.2 g, 41.61 mmol) under nitrogen atmosphere. The reaction mixture was cooled to 0-5° C. Methane sulfonyl chloride (1.58 g, 13.87 mmol) was added at 0-5° C. dropwise in 20 mins. The reaction mixture was stirred at same temp for 1 h. Progress of reaction was monitored by TLC. The reaction mixture was diluted with dichloromethane (20 ml) and washed with water (3×20 ml). The organic layer was dried over sodium sulphate and concentrated under reduced pressure to obtain title compound (4.2 g) which was used for the next reaction without further purification.

Step 2: 4-(4-(4-fluorophenyl) piperazin-1-yl)pentanenitrile

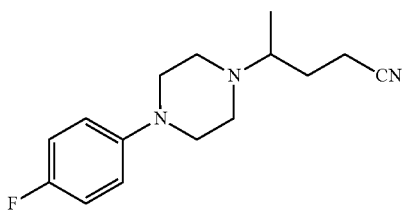 [SMILES: CC(CCC#N)N1CCN(c2ccc(F)cc2)CC1]

To a stirred solution of 3-(4-(4-fluorophenyl) piperazin-1-yl)butyl methanesulfonate (4.5 g, 13.62 mmol) in N,N-dimethylformamide (30 ml) was added potassium cyanide (2.66 g, 40.9 mmol) at 25° C. under nitrogen atmosphere. The reaction mixture was stirred at 50° C. for 15 h. Progress of reaction was monitored by TLC. The reaction mixture was diluted with ethyl acetate (150 ml) and washed with water (4×50 ml). The organic layer was dried over sodium sulphate and concentrated under reduced pressure to get oily compound. The resulting crude compound was purified over silica gel (100-200 mesh) by flash chromatography using 30% ethyl acetate in hexane as an eluent to obtain title compound (2.6 g).

$^1$H NMR (400 MHz, CDCl$_3$): δ 6.98 (t, J=8.4 Hz, 2H), 6.90-6.85 (m, 2H) 3.16-3.10 (m, 4H) 2.80-2.76 (m, 4H) 2.67-2.59 (m, 2H), 2.54-2.44 (m, 1H) 1.81-177 (m, 1H) 1.74-1.67 (s, 1H) 1.05 (s, 3H)

MS: m/z 261.9 (M+1)

EXAMPLE 5

Synthesis of 4-(4-(4-fluorophenyl)piperazin-1-yl)-4-methylpentanenitrile

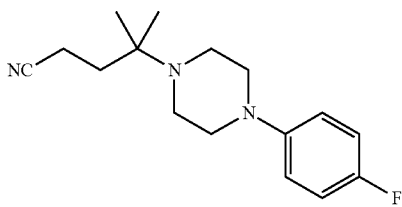 [SMILES: CC(C)(CCC#N)N1CCN(c2ccc(F)cc2)CC1]

Step 1: 2-(4-(4-fluorophenyl)piperazin-1-yl)-2-methylpropan-1-ol

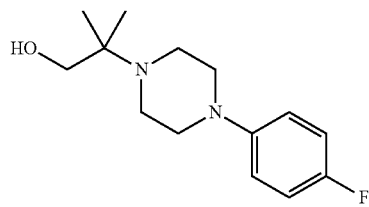 [SMILES: CC(C)(CO)N1CCN(c2ccc(F)cc2)CC1]

To a stirred solution of lithium aluminium hydride (0.774 g, 20.4 mmol) in tetrahudrofuran (20 mL) was added ethyl 2-(4-(4-fluorophenyl)piperazin-1-yl)-2-methylpropanoate (prepared according to procedure reported in *Bioorganic & Medical Chemistry*, 2006, 14, 2725; 2.0 g, 6.79 mmol) in tetrahudrofuran (10 mL) was added slowly at 25° C. The resulting mixture was then stirred for 16 h. After completion of reaction, ethyl acetate (5 ml) was added followed by 1N Sodium hydroxide (20 ml) and allowed to stirred for 1 h. It was then passed through a celite bed and washed with ethyl acetate (100 ml. To the filtrate water (50 ml) was added and extracted with ethyl acetate (3×50 mL), combined organic layers was dried over sodium sulphate and concentrated to afford crude product. Crude product was purified by using silica gel (100-200 mesh) column chromatography using 5% methanol in dichloromethane as eluent to obtain the titled compound (1.5 g, 87.0%).

$^1$H NMR (400 MHz, CDCl$_3$): δ 7.00-6.95 (m, 2H), 6.91-6.87 (m, 2H), 3.41 (s, 2H), 3.16-3.13 (m, 4H), 2.78-2.75 (m, 4H), 2.01 (brs, 1H, D$_2$O exchangeable) 1.11 (s, 6H).

MS: m/z 253 (M+1).

Step 2: 2-(4-(4-fluorophenyl)piperazin-1-yl)-2-methylpropanal

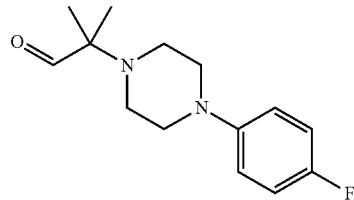 [SMILES: CC(C)(C=O)N1CCN(c2ccc(F)cc2)CC1]

To a stirred solution of oxalyl chloride (0.7 mL, 8 mmol) in dichloromethane (30 mL) at −60° C. was added dropwise dimethylsulphoxide (1.1 mL, 15.5 mmol). The mixture was stirred for 2 min, and a solution of 2-(4-(4-fluorophenyl) piperazin-1-yl)-2-methylpropan-1-ol (1.5 g, 4.9 mmol) in dichloromethane (10 mL) was then added. The reaction mixture was stirred for 15 min, triethylamine (5 mL, 25.5 mmol) was added. The reaction mixture was stirred for 5 min and then allowed to warm to room temperature. Water (100 mL) was then added and the aqueous layer was extracted with additional dichloromethane (100 mL). The organic layers were combined, washed sequentially with brine (200 mL), dried over sodium sulphate and evaporated till dryness. The crude product was purified by column chromatography over silica gel (100-200 mesh) using 10% ethylacetate in hexane to obtain the title compound (1.2 g, 83.0%).

$^1$H NMR (400 MHz, CDCl$_3$): δ 9.50 (s, 1H), 7.00-6.96 (m, 2H), 6.90-6.87 (m, 2H), 3.24-3.15 (m, 4H), 2.70-2.68 (m, 4H), 1.14 (s, 6H).

Step 3: (E)-4-(4-(4-fluorophenyl)piperazin-1-yl)-4-methylpent-2-enenitrile

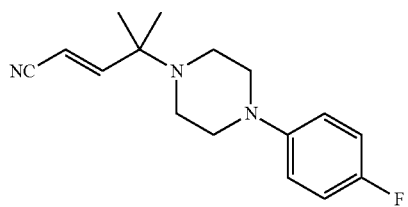 [SMILES: CC(C)(/C=C/C#N)N1CCN(c2ccc(F)cc2)CC1]

To the stirred solution of 2-(4-(4-fluorophenyl)piperazin-1-yl)-2-methylpropanal (1.0 g, 4 mmol) in 10 ml of dichloromethane was added 2-(triphenylphosphoranylidene)acetonitrile (1.445 g, 4.8 mmol) at 25° C. The reaction was stirred for 2 days at room temperature. After completion of reaction, the solvent was evaporated to give a crude product. The crude product was purified by column chromatography using 10% ethyl acetate in hexane as an eluent to obtain the title compound (0.7 g, 64.1%).

$^1$H NMR (400 MHz, CDCl$_3$): δ 7.13-6.94 (m, 2H), 6.91-6.85 (m, 2H), 6.78 (d, J=16.8 Hz, 1H), 5.50 (d, J=16.8 Hz, 1H), 3.18-3.12 (m, 4H), 2.76-2.70 (m, 4H), 1.17 (s, 6H).

MS: m/z 274 (M+1).

Step 4: 4-(4-(4-fluorophenyl)piperazin-1-yl)-4-methylpentanenitrile

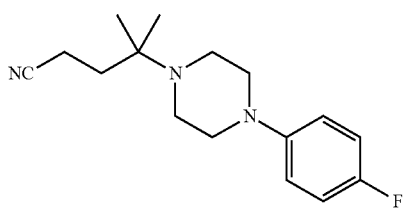 [SMILES: CC(C)(CCC#N)N1CCN(c2ccc(F)cc2)CC1]

To the stirred solution of (E)-4-(4-(4-fluorophenyl)piperazin-1-yl)-4-methylpent-2-enenitrile (1.5 g), was added sodumborohydride (0.453 mg) in dimethoxyethane (30 ml) and stirred at room temperature for 1 hour before being heated to 75° C. for 2 h. The solution was cooled to room temperature and allowed to stirrer at 25° C. for 24 h then quenched with saturated ammonium chloride (50 mL). The aqueous phase was extracted with dichloromethane (3×50 ml). The organic phase was dried over sodium sulphate and concentrated under vacuum. The residue was purified by flash column chromatography using 20% ethyl acetate in hexane as an eluent to obtain the title compound (1.3 g, 58.6%).

$^1$H NMR (400 MHz, CDCl$_3$) δ 7.13-6.94 (m, 2H), 6.91-6.85 (m, 2H), 3.18-3.12 (m, 4H), 2.76-2.70 (m, 4H), 2.44 (t, J=7.8 Hz, 1H), 1.85 (t, J=7.8 Hz, 1H), 1.08 (s, 6H).

MS: m/z 276 (M+1).

EXAMPLE 6

Synthesis of 4-(4-(4-fluorophenyl)-2-methylpiperazin-1-yl)butanenitrile

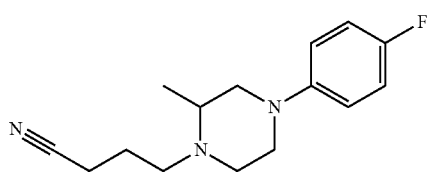 [SMILES: CC1CN(c2ccc(F)cc2)CCN1CCCC#N]

Step 1: tert-butyl 4-(3-cyanopropyl)-3-methylpiperazine-1-carboxylate

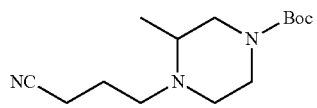 [SMILES: CC1CN(C(=O)OC(C)(C)C)CCN1CCCC#N]

To the stirred solution of tert-butyl 3-methylpiperazine-1-carboxylate (prepared according to procedure reported in US200876758A1, 2008, 5 g, 24.97 mmol) in N,N-dimethylformamide (50 ml) were added potassium carbonate (17.25 g, 125 mmol) and 4-bromobutanenitrile (2.98 ml, 30.0 mmol) at 25° C. The resulting solution was stirred at 25° C. for 16 h. The progress of the reaction was monitored by TLC. After completion of the reaction water (100 ml) was added and extracted with dichloromethane (3×60 ml). The combined extract was washed with brine (25 ml) and dried over sodium sulphate, filtered and concentrated to give crude compound. The crude compound was purified by column chromatography over silica gel (100-200) using 15% ethyl acetate in hexane to obtain the title compound (5 g, 75%).

$^1$H NMR (400 MHz, CDCl$_3$) δ 3.66-3.62 (m, 2H), 3.16-3.13 (m, 1H), 2.85-2.66 (m, 3H), 2.41-2.14 (m, 5H), 1.81-1.74 (m, 2H), 1.72 (s, 9H), 1.00 (d, J=6.4 Hz, 3H).

Step 2: 4-(2-methylpiperazin-1-yl)butanenitrile hydrochloride

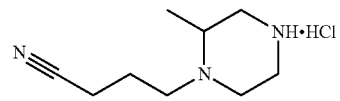

To a stirred solution of tert-butyl 4-(3-cyanopropyl)-3-methylpiperazine-1-carboxylate (1.3 g, 4.86 mmol) in diethyl ether (10 ml) was added hydrochloric acid (2 molar in ether, 10 ml, 20.00 mmol) at 0° C. The reaction mixture was stirred at room temperature for 5 h. Progress of the reaction was monitored by TLC. After completion of the reaction, the solvent was evaporated under reduced pressure and triturated with diethyl ether to yield the title compound 4-(2-methylpiperazin-1-yl)butanenitrile hydrochloride (1 g, 4.91 mmol, 24.54% yield)

$^1$H NMR (400 MHz, DMSO-d6) δ 12.24 (bs, 1H, Exchangeable with D$_2$O), 10.19 (bs, 1H, Exchangeable with D$_2$O), 9.97 (bs, 1H, Exchangeable with D$_2$O), 4.30-4.15 (m, 3H), 3.72-3.10 (m, 6H), 2.66-2.51 (m, 2H), 2.11-2.05 (m, 2H), 1.39 (d, J=6.4 Hz, 3H).

Step 3: 4-(4-(4-fluorophenyl)-2-methylpiperazin-1-yl)butanenitrile

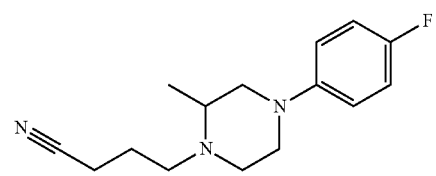 [SMILES: CC1CN(c2ccc(F)cc2)CCN1CCCC#N]

To a stirred solution of 4-(2-methylpiperazin-1-yl)butanenitrile hydrochloride (1 g, 4.91 mmol) in 1,4 dioxane (25 ml) at 25° C. was added 2,2'-Bis(diphenylphosphino)-1,1'-binaphthyl (0.306 g, 0.491 mmol), NaOtBu (1.415 g, 14.73 mmol), 1-bromo-4-fluorobenzene (0.648 ml, 5.89 mmol) and tris(dibenzyllideneacetone)dipalladium (0) [Pd$_2$(dba)$_3$] (0.225 g, 0.245 mmol). The resulting reaction mixture was purged with nitrogen for 10 min in sealed tube and stirred at 100° C. in seal tube for 15 h. Progress of the reaction was monitored by TLC. After completion of reaction, the reaction mixture was cooled to room temperature, filtered through a celite bed, and washed with ethyl acetate (2×20 ml). The filtrate was concentrated under reduced pressure to get crude compound. The crude compound was purified by column chromatography over silica gel (100-200 mesh) using 25% ethyl acetate in hexane as eluent to obtain title compound (0.65 g, 50.7).

$^1$H NMR (400 MHz, CDCl$_3$) δ 7.10-6.90 (m, 2H), 6.89-6.86 (m, 2H), 3.34-3.26 (m, 2H), 2.96-2.87 (m, 3H), 2.63-2.52 (m, 2H), 2.48-2.37 (m, 7H), 1.89-1.79 (m, 2H).

MS: m/z 262 (M+1).

EXAMPLE 7

Synthesis of 8-benzyl-3,8-diazabicyclo[3.2.1]octane

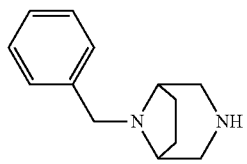 [SMILES: c1ccc(CN2C3CCC2CNC3)cc1]

To a stirred suspension of lithium aluminium hydride in tetrahudrofuran (30 ml) at 0° C. was added a solution of (1S,5R)-8-benzyl-3,8-diazabicyclo[3.2.1]octan-2-one (prepared according to the procedure reported in US200565178 A1, 1.0 g, 4.62 mmol) in 15 ml tetrahudrofuran (15 ml) under nitrogen atmosphere. The reaction mixture was allowed to stir at 25° C. for 2 h and at 65-70° C. for 1 h. The reaction mixture was cooled to 0° C. and slowly quenched with 15% aqueous Sodium hydroxide (5 ml). The reaction mixture was diluted with ethyl acetate (50 ml) and filtered through a celite bed. The filtrate was dried over sodium sulphate and concentrated under reduced pressure to obtain the title compound (0.85 g, 91%).

$^1$H NMR (400 MHz, CDCl$_3$): δ 7.54-7.23 (m, 5H) 3.48 (s, 2H) 3.06-3.00 (m, 4H) 2.60-2.57 (m, 2H), 2.05-1.98 (m, 3H overlap with exchangeable proton) 1.75-1.70 (m, 2H)

EXAMPLE 8

Synthesis of (1R,5S)-8-benzyl-3-(4-fluorophenyl)-3,8-diazabicyclo[3.2.1]octane

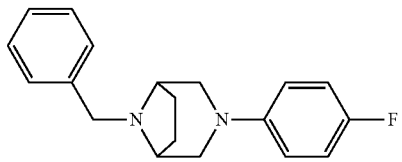 [SMILES: Fc1ccc(N2CC3CCC(C2)N3Cc2ccccc2)cc1]

To a stirred solution of 8-benzyl-3,8-diazabicyclo[3.2.1]octane (2.5 g, 12.36 mmol) in 1,4-dioxane (15 ml) in sealed tube at 25° C. was added 2,2'-Bis(diphenylphosphino)-1,1'-binaphthyl (0.770 g, 1.23 mmol), sodium tert-butoxide (2.37 g, 24.72 mmol), 1-bromo-4-fluorobenzene (1.63 ml, 14.83 mmol) and tris(dibenzyllideneacetone)dipalladium (0) [Pd2(dba)$_3$] (0.566 g, 0.618 mmol). The resulting reaction mixture was purged with nitrogen for 10 min and stirred at 100° C. for 15 h. The reaction mixture was then cooled to 25° C., filtered through a celite bed, and the celite bed was washed with ethyl acetate (2×20 ml). The combined filtrate was concentrated under reduced pressure to get crude compound. The resulting crude compound was purified by using flash column chromatography over silica gel (100-200 mesh) using 10% ethylacetate in hexane to obtain title compound (2.4 g 66%).

$^1$H NMR (400 MHz, CDCl$_3$): δ 7.43-7.28 (m, 5H) 6.97-6.92 (m, 2H), 6.75-6.72 (m, 2H), 3.61 (s, 2H), 3.32-3.26 (m, 4H), 3.01-2.99 (m, 2H), 2.07-2.05 (m, 2H), 1.83-1.81 (m, 2H)

MS: m/z 297 (M+1)

EXAMPLE 9

Synthesis of (1R,5S)-3-(4-fluorophenyl)-3,8-diazabicyclo[3.2.1]octane

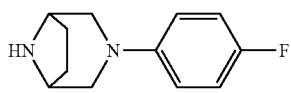 [SMILES: Fc1ccc(N2CC3CCC(C2)N3)cc1]

To the stirred solution of 8-benzyl-3-(4-fluorophenyl)-3,8-diazabicyclo[3.2.1]octane (3.5 g, 11.81 mmol) in methanol (30 ml) was added 10% palladium on charcoal (100 mg, 0.940 mmol) at 25° C. The reaction mixture was stirred under hydrogen atmosphere for 3-4 h at 40° C. The reaction mixture was then cooled to 25° C. and filtered through a celite bed. The celite bed was washed with methanol (2×25 ml). The combined filtrate was concentrated under reduced pressure to obtain title compound (2.3 g, 94%).

$^1$H NMR (400 MHz, CDCl$_3$): δ 6.98-6.93 (m, 2H) 6.77-6.72 (m, 2H), 3.89 (s, 1H, D$_2$O exchangeable) 3.38-3.34 (m, 4H) 2.92-2.89 (m, 2H) 1.93-184 (m, 4H)

EXAMPLE 10

Synthesis of (R)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one hydrochloride salt (Compound 42 hydrochloride salt)

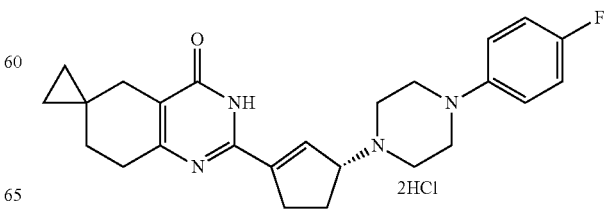

Step 1: 3-bromocyclopent-1-enecarbonitrile

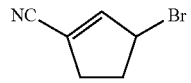

To a stirred solution of cyclopent-1-enecarbonitrile (50 g, 537 mmol) in tetrachloromethane (400 ml) at 25° C. was added was added N-bromosuccinimide (96 g, 537 mmol) under nitrogen atmosphere. The resulting mixture was refluxed for 2 h. The progress of reaction was monitored by TLC. The reaction mixture cooled to 25° C. and filtered through celite. The filtrate was concentrated under reduced pressure to obtain a crude product, which was purified by column chromatography over silica gel (100-200 mesh) using 1% ethyl acetate in hexane as an eluent to obtain the title compound (60 g, 65%).

$^1$HNMR (CDCl$_3$, 400 MHz): δ 6.77-6.73 (m, H), 5.12-5.09 (m, 1H) 2.95-2.86 (m, 1H) 2.67-2.42 (m, 3H)

Step 2: (R)-3-(4-(4-fluorophenyl)piperazin-1-yl)cyclopent-1-enecarbonitrile

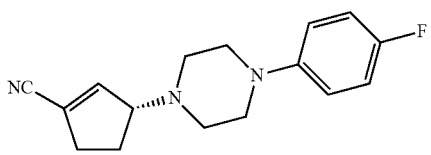 [SMILES: N#CC1=C[C@H](N2CCN(c3ccc(F)cc3)CC2)CC1]

To a stirred solution of 3-bromocyclopent-1-enecarbonitrile (3 g, 17.44 mmol) in N,N-dimethylformamide (25 ml) was added 1-(4-fluorophenyl)piperazine (3.14 g, 17.44 mmol) followed by the addition of triethylamine (7.29 ml, 52.3 mmol) in a dropwise manner at 0° C. The reaction mixture was stirred at 25° C. for 3 h. The progress of reaction was monitored by TLC. The reaction mixture was then concentrated under reduced pressure. The residue was then diluted with ethyl acetate (100 ml) and washed with water (4×30 ml). The organic layer was dried over sodium sulphate, and concentrated under reduced pressure to obtain a crude product. The crude product was purified by flash column over silica gel (100-200 mesh) using 20% ethyl acetate in hexane as eluent to obtain the title compound (2.7 g, 57.1%).

$^1$H NMR (400 MHz, CDCl$_3$): δ 7.00-6.94 (m, 2H), 6.91-6.85 (m, 2H) 6.72-6.70 (m, 1H) 4.00-3.98 (m, 1H) 3.14-2.97 (m, 4H) 2.74-2.60 (m, 6H) 2.16-1.99 (m, 2H)

MS: m/z 272 (M+1)

A chiral resolution of 3-(4-(4-fluorophenyl)piperazin-1-yl)cyclopent-1-enecarbonitrile was carried out using chiral column to obtain (R) 3-(4-(4-fluorophenyl)piperazin-1-yl)cyclopent-1-enecarbonitrile (1.4 g) and (S) 3-(4-(4-fluorophenyl)piperazin-1-yl)cyclopent-1-enecarbonitrile (1.3 g).

Step 3: (R)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one The title compound was obtained from (R)-3-(4-(4-fluorophenyl)piperazin-1-yl)cyclopent-1-enecarbonitrile were prepared using procedure describe in step 3 and step 4 of example 1.

$^1$H NMR (400 MHz, DMSO-d$_6$): δ 11.50 (brs, 1H, D$_2$O exchangeable), 7.00-7.10 (m, 2H), 7.02-7.08 (m, 2H), 6.95 (brs, 1H), 4.70 (brs, 1H), 3.75-3.80 (m, 2H), 3.52 (brs, 2H), 3.08-3.17 (m, 4H), 2.76-2.89 (m, 2H), 2.61-2.67 (m, 2H), 2.40-2.35 (m, 2H), 2.56 (brs, 2H), 1.53 (t, J=6.4 Hz, 2H), 0.41 (brs, 4H), MS: m/z 421.5 (M+1)

Step 4: Hydrochloride salt of (R)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 42 hydrochloride salt)

To a stirred solution of 2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (550 mg, 1.308 mmol) in dichloromethane (15 ml), and methanol (15 ml) was added hydrochloric acid (2.62 ml, 5.23 mmol, 2M solution in ether) was added at 5-10° C. Reaction mix was stirred at 25° C. for 40-45 mins. Reaction mixture was concentrated under reduced pressure to obtain sticky solid, which was washed with ether (2×10 ml) to afford title compound (0.590 gm).

$^1$H NMR (400 MHz, DMSO-d$_6$): δ 12.30 (brs, 1H, D$_2$O exchangeable), 7.13-7.09 (m, 2H), 7.05-7.02 (m, 2H), 6.95 (s, 1H), 4.67 (s, 1H), 3.78-3.75 (m, 2H), 3.52 (brs, 2H), 3.17-3.08 (m, 4H), 2.89-2.76 (m, 2H), 2.67-2.61 (m, 2H), 2.35-2.32 (m, 2H), 2.63 (brs, 2H), 1.53 (t, J=6.4 Hz, 2H), 0.39 (brs, 4H), MS: m/z 421.5 (M+1)

EXAMPLE 11

Synthesis of (R)-3-(4-(4-fluorophenyl)piperazin-1-yl)cyclopent-1-enecarbonitrile

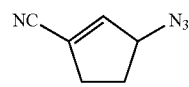

To a solution of 3-bromocyclopent-1-enecarbonitrile (20 g, 116 mmol) in dimethylformamide (100 ml) at 25° C. was added in portion sodium azide (11.34 g, 174 mmol) portion wise over a period of 5 min at 0° C. and the reaction mixture was stirred at 0° C. for 45 minutes. The progress of reaction was monitored by TLC. The reaction mixture was poured in to cold water (200 ml) and product was extracted in ethylacetate (3×300 ml). The combined organic layer was dried over anhydrous sodium sulphate and concentrated under reduced pressure to obtain a crude product. The crude product was further purified by column chromatography over silica gel (100-200 mesh) using 40% ethyl acetate in hexane as an eluent to obtain the title compound (15 g, 96%). The resulting compound was forwarded to next step without characterization.

Step 3: tert-butyl (3-cyanocyclopent-2-en-1-yl)carbamate

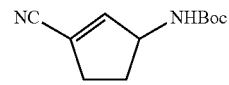

To the stirred solution of 3-azidocyclopent-1-enecarbonitrile (32 g, 239 mmol) in a mixture of tetrahydrofuran:ethanol (150 ml:60 ml) was added triphenylphosphene (125 g, 477 mmol) at 0° C. The resulting reaction mixture was stirred for 12 h at room temperature. The reaction mixture was cooled to 0° C. and were added sodium hydroxide solution (20 ml, 1N) and di-tert-butyl carbonate (65.8 ml, 286 mmol). The reaction mixture was stirred at 25° C. for 2 h. The progress of reaction was monitored by TLC. The reaction mixture was then concentrated under reduced pressure. The residue was obtained diluted with ethyl acetate (150 ml). The organic layer was washed with water (2×100 ml) and dried over anhydrous sodium sulphate and concentrated under reduced pressure to obtain a crude product. The crude product was further purified by column chromatography over silica gel (100-200 mesh) using 20% ethyl acetate in hexane as an eluent to obtain the tittle compound (30 g, 64%). A chiral resolution of tert-butyl (3-cyanocyclopent-2-en-1-yl)carbamate (30 g) was carried out using chiral column to obtain (R) tert-butyl (3-cyanocyclopent-2-en-1-yl)carbamate (13 g) and (S) tert-butyl (3-cyanocyclopent-2-en-1-yl)carbamate (12.5 g).

$^1$HNMR (CDCl$_3$, 400 MHz): δ δ 6.58-6.56 (m, 1H) 4.91-4.88 (m, 1H), 4.62 (s, 1H, D$_2$O exchangeable) 2.70-2.47 (m, 3H) 1.73-1.64 (m, 1H) 1.46 (s, 9H)

Step 4: (R)-3-aminocyclopent-1-enecarbonitrile

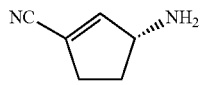

To a solution of (R)-tert-butyl (3-cyanocyclopent-2-en-1-yl)carbamate (4.0 g, 19.21 mmol) in dichloromethane (30 ml) was added hydrochloric acid (5.84 ml, 192 mmol, 15 ml 4M solution in dioxane) at 25° C. and the reaction mixture was stirring at same temperature for 2 h. The progress of reaction was monitored by TLC. The reaction mixture was concentrated under reduced pressure to obtain the tittle compound (2.7 g, 97%).

$^1$HNMR (CDCl$_3$, 400 MHz): δ δ 8.48 (s, 2H, D$_2$O exchangeable), 6.80-6.79 (m, 1H), 4.35-4.31 (m, 1H), 2.77-2.73 (m, 2H), 2.37-2.30 (m, 1H), 1.93-1.86 (m, 1H)

Step 5: (R) 3-(4-(4-fluorophenyl)piperazin-1-yl)cyclopent-1-enecarbonitrile

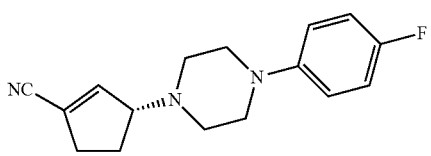 [SMILES: N#CC1=C[C@H](N2CCN(c3ccc(F)cc3)CC2)CC1]

To a solution of (R)-3-aminocyclopent-1-enecarbonitrile hydrochloride (0.6 g, 4.15 mmol) in anhydrous acetonitrile (40 ml), were added (4-fluorophenyl)azanediyl)bis(ethane-2,1-diyl)dimethanesulfonate, 2.21 g, 6.22 mmol, prepared according to procedure given in US2011237553), potassium carbonate (2.294 g, 16.60 mmol) and lithium bromide (0.757 g, 8.71 mmol). The reaction mixture was heated under stirring at about 80-83° C. for 18 h under a nitrogen atmosphere. The progress of reaction was monitored by TLC. The reaction mixture was cooled to 25° C. and quenched with water (50 ml). The aqueous layer was extracted with ethyl acetate (2×100 ml). The combined organic layer was dried over anhydrous sodium sulphate then cooled to room temperature and concentrated under reduced pressure to obtain a crude product which was purified over silica gel (100-200 mesh) using 30% ethyl acetate in hexane as an eluent to obtain the title compound (0.350 g, 39%).

$^1$HNMR (CDCl$_3$, 400 MHz): δ δ 7.00-6.94 (m, 2H), 6.91-6.85 (m, 2H) 6.72-6.70 (m, 1H,) 4.00-3.98 (m, 1H) 3.14-2.97 (m, 4H) 2.74-2.60 (m, 6H) 2.16-1.99 (m, 2H)

EXAMPLE 12

The following compounds were synthesized according to the procedures described above in example 10 and/or 11 with appropriate changes in the reactants and reaction conditions.

Hydrochloride salt of (R)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one. (Compound 37 hydrochloride salt)

$^1$H NMR (400 MHz, DMSO-d$_6$): δ 11.48 (brs, 1H, D$_2$O exchangeable), 7.28 (d, J=9.2 Hz, 2H), 7.03 (d, J=9.2 Hz, 2H), 6.96 (brs, 1H), 4.67 (brs, 1H), 4.12 (s, 2H), 3.84 (brs, 2H), 3.57-3.52 (m, 2H), 3.17-3.15 (m, 4H), 2.87-2.76 (m, 2H), 2.64 (brs, 2H), 2.33-2.26 (m, 4H), 1.53 (t, J=6.0 Hz, 2H), 0.38 (brs, 4H)
MS: m/z 437 (M+1)

Hydrochloride salt of (S)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one (Compound 38 hydrochloride salt)

$^1$H NMR (400 MHz, DMSO-d$_6$): δ 11.56 (brs, 1H, D$_2$O exchangeable), 7.29 (d, J=8.8 Hz, 2H), 7.03 (d, J=9.2 Hz, 2H), 6.98 (brs, 1H), 4.69 (brs, 1H), 3.84 (s, 2H), 3.59 (brs, 2H), 3.57-3.52 (m, 2H), 3.21-3.12 (m, 4H), 2.87-2.75 (m, 2H), 2.54 (brs, 2H), 2.26 (brs, 2H), 1.53 (t, J=6.0 Hz, 2H), 0.39 (brs, 4H)
MS: m/z 437 (M+1)

Hydrochloride salt of 2'-(3-(4-(pyridin-4-yl)piperazin-1-yl)cyclopent-1-en-1-yl)-7',8'-dihydro-3'H-spiro[cyclopropane-1,6'-quinazolin]-4'(5'H)-one (Compound 39 hydrochloride salt)

$^1$H NMR (400 MHz, DMSO-d$_6$): δ 14.13 (brs, 1H, D$_2$O exchangeable), 8.36 (brs, 2H), 7.29-7.31 (brs, 2H), 6.92 (brs, 1H), 4.67 (brs, 1H), 4.47-4.51 (m, 2H), 4.29 (brs, 2H, D$_2$O exchangeable), 3.96-2.25 (m, 13H), 1.53 (, t, J=6.0 Hz, 2H), 0.38 (brs, 4H).
MS: m/z 403.7 (M+1)

Hydrochloride salt of (S)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 40 hydrochloride salt)

$^1$H NMR (400 MHz, DMSO-d$_6$): δ 12.30 (brs, 1H, D$_2$O exchangeable), 11.28 (brs, 1H, D$_2$O exchangeable), 7.29 (d, J=8.8 Hz, 2H), 7.02 (d, J=9.2 Hz, 2H), 6.89 (brs, 1H), 4.64 (m, 1H), 3.85 (brs, 2H), 3.51-3.49 (m, 2H), 3.16-3.12 (m, 4H), 2.78-2.67 (m, 2H), 2.32-2.26 (m, 2H), 1.74-1.65 (m, 6H), 1.23-1.20 (m, 2H), 0.71 (brs, 2H)
MS: m/z 437.4 (M+1)

Hydrochloride salt of (R)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 41 hydrochloride salt)

$^1$H NMR (400 MHz, DMSO-d$_6$): δ 11.56 (brs, 1H, D$_2$O exchangeable), 7.29 (d, J=8.8 Hz, 2H), 7.03 (d, J=9.2 Hz, 2H), 6.98 (brs, 1H), 4.69 (brs, 1H), 3.84 (s, 2H), 3.59 (s, 2H), 3.57-3.52 (m, 2H), 3.21-3.12 (m, 4H), 2.87-2.75 (m, 2H), 2.54 (brs, 2H), 2.26 (brs, 2H), 1.53 (t, J=6.0 Hz, 2H), 0.39 (brs, 4H)

MS: m/z 437 (M+1)

Hydrochloride salt of (S)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 43 hydrochloride salt)

$^1$H NMR (400 MHz, DMSO-d$_6$): δ 11.55 (brs, 1H, D$_2$O exchangeable), 7.44 (brs, 2H, D$_2$O exchangeable), 7.13-7.09 (m, 2H), 7.05-7.02 (m, 2H), 6.99 (brs, 1H), 4.68 (s, 1H), 3.76 (d, J=7.4 Hz, 2H), 3.52 (brd, 2H), 3.16 (d, J=6.8 Hz, 4H), 2.86-2.80 (m, 2H), 2.67-2.64 (m, 2H), 2.36-2.30 (m, 2H), 2.67 (brs, 2H), 1.53 (t, J=6.0 Hz, 2H), 0.40-0.39 (m, 4H)

MS: m/z 421 (M+1)

Hydrochloride salt of N-cyclopropyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 44 hydrochloride salt)

$^1$H NMR (400 MHz, DMSO-d$_6$): δ 11.48 (brs, 1H, D$_2$O exchangeable), 8.25 (brs, 1H, exchangeable), 7.75 (d, J=8.0 Hz, 2H), 7.02 (d, J=8.4 Hz, 2H), 6.95 (s, 1H), 4.67 (brs, 1H), 4.02 (s, 2H), 3.99 (brs, 2H, exchangeable), 3.53 (s, 2H), 3.27-3.14 (m, 4H), 2.88-2.80 (m, 3H), 2.63 (brs, 2H), 2.33 (s, 2H), 2.25 (s, 2H), 2.53 (brs, 2H), 0.66-0.65 (m, 2H), 0.59-0.54 (m, 2H), 0.37-0.36 (m, 4H)

MS: m/z 485.7 (M+1)

Hydrochloride salt of (R)2'-(3-(4-(4-fluorophenyl)-3-oxopiperazin-1-yl)cyclopent-1-en-1-yl)-7',8'-dihydro-3'H-spiro[cyclopropane-1,6'-quinazolin]-4'(5'H)-one (Compound 45 hydrochloride salt)

$^1$H NMR (400 MHz, DMSO-d$_6$): δ 12.60 (brs, 1H, D$_2$O exchangeable), 7.37-7.28 (m, 4H), 6.93 (s, 1H), 4.75 (brs, 1H), 4.01 (s, 2H), 3.79 (brs, 2H), 3.38-3.36 (m, 1H), 2.74-2.71 (m, 2H), 2.65 (brs, 2H), 2.36-2.35 (m, 2H), 2.26 (s, 4H), 1.53 (brs, 2H), 0.39 (brs, 4H)

MS: m/z 435 (M+1)

Hydrochloride salt of (R)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 46 hydrochloride salt)

$^1$H NMR (400 MHz, DMSO-d$_6$): δ 11.36 (brs, 1H, D$_2$O exchangeable), 7.52 (d, J=8.0 Hz, 2H), 7.45 (d, J=8.0 Hz, 2H), 6.98 (d, J=20.0 Hz, 1H), 6.27 (s, 1H), 4.92 (brs, 1H, D$_2$O exchangeable), 4.73 (brs, 1H), 3.98-3.22 (m, 4H), 2.89-2.63 (m, 10H), 1.53 (t, J=5.6 Hz, 2H), 0.39 (brs, 4H)

MS: m/z 433.9 (M+1)

Hydrochloride salt of (S)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 47 hydrochloride salt)

$^1$H NMR (400 MHz, DMSO-d$_6$): δ 11.36 (brs, 1H, D$_2$O exchangeable), 7.52 (d, J=8.0 Hz, 2H), 7.45 (d, J=8.0 Hz, 2H), 6.98 (d, J=20.0 Hz, 1H), 6.27 (s, 1H), 4.92 (brs, 1H, D$_2$O exchangeable), 4.73 (brs, 1H), 3.98-3.22 (m, 4H), 2.89-2.63 (m, 10H), 1.53 (t, J=5.6 Hz, 2H), 0.39 (brs, 4H)

MS: m/z 434 (M+1)

Hydrochloride salt of (R)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 48 hydrochloride salt)

$^1$H NMR (400 MHz, DMSO-d$_6$): δ 12.30 (brs, 1H, D$_2$O exchangeable), 11.09 (s, 1H, D$_2$O exchangeable), 7.13-7.08 (m, 2H), 7.05-7.01 (m, 2H), 6.89 (brs, 1H, D$_2$O exchangeable), 5.15 (brs, 1H), 4.65 (brs, 1H), 3.78-3.76 (m, 2H), 3.54-3.49 (m, 2H), 3.16-3.08 (m, 4H), 2.76-2.26 (m, 6H), 1.74-1.65 (m, 4H), 1.20 (s, 2H), 0.72 (s, 2H)

MS: m/z 421.4 (M+1)

Hydrochloride salt of (S)-2'-(3-(4-(4-fluorophenyl)piperazin-1-yl)cyclopent-1-en-1-yl)-6',7'-dihydro-3'H-spiro[cyclopropane-1,8'-quinazolin]-4'(5'H)-one (Compound 49 hydrochloride salt)

$^1$H NMR (400 MHz, DMSO-d$_6$): δ 12.31 (brs, 1H, D$_2$O exchangeable), 11.20 (s, 1H, D$_2$O exchangeable), 7.13-7.09 (m, 2H), 7.05-7.01 (m, 2H), 6.90 (s, 1H), 4.63 (s, 1H), 3.72-3.07 (m, 8H), 2.76-2.67 (m, 2H), 2.33-2.08 (m, 2H), 1.74-1.65 (m, 4H), 1.35-1.23 (m, 4H), 0.71 (brs, 2H)

MS: m/z 421 (M+1)

Hydrochloride salt of 2'-(3-(4-(4-bromophenyl)piperazin-1-yl)cyclopent-1-en-1-yl)-7',8'-dihydro-3'H-spiro[cyclopropane-1,6'-quinazolin]-4'(5'H)-one (Compound 50 hydrochloride salt)

$^1$H NMR (400 MHz, DMSO-d$_6$): δ 11.42 (brs, 1H, D$_2$O exchangeable), 7.41 (d, J=8.8 Hz, 2H), 6.98 (d, J=8.8 Hz, 2H), 6.95 (s, 1H), 4.67 (brs, 1H), 3.85-3.87 (m, 2H), 3.50-3.52 (m, 2H), 3.37-3.32 (m, 4H), 2.89-2.75 (m, 2H), 2.65-2.62 (m, 2H), 2.45-2.31 (m, 4H), 1.53 (t, J=6.0 Hz, 2H), 0.39 (s, 4H)

MS: m/z 481, (M+1) 483 (M+3)

Hydrochloride salt of (S)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 51 hydrochloride salt)

$^1$H NMR (400 MHz, DMSO-d$_6$): δ 10.80 (brs, 1H, D$_2$O exchangeable), 7.56-7.53 (m, 2H), 7.25-7.21 (m, 2H), 6.93 (d, J=20.4 Hz, 1H), 6.20 (s, 1H), 4.72 (s, 1H), 3.62-2.08 (m, 14H), 1.53 (t, J=6.0 Hz, 2H), 0.38 (s, 4H)

MS: m/z 417.6 (M+1)

Hydrochloride salt of (R)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H)-one (Compound 52 hydrochloride salt)

$^1$H NMR (400 MHz, DMSO-d$_6$): δ 10.80 (brs, 1H, D$_2$O exchangeable), 7.56-7.53 (m, 2H), 7.25-7.21 (m, 2H), 6.93

(d, J=20.4 Hz, 1H), 6.20 (s, 1H), 4.72 (s, 1H), 2.08-3.62 (m, 14H), 1.53 (t, J=6.0 Hz, 2H), 0.38 (s, 4H)

MS: m/z 417.6 (M+1)

Hydrochloride salt of (S)—N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 53 hydrochloride salt)

$^1$H NMR (400 MHz, DMSO-d$_6$): δ 11.59 (brs, 1H, D$_2$O exchangeable), 8.26 (s, 1H, D$_2$O exchangeable), 7.76 (d, J=8.4 Hz, 2H), 7.04 (d, J=8.4 Hz, 2H), 6.98 (s, 1H), 4.99 (brs, 2H, D$_2$O exchangeable), 4.68 (s, 1H), 4.01-3.99 (m, 2H), 3.52-2.61 (m, 17H), 1.53 (t, J=6.0 Hz, 2H), 0.38 (s, 4H)

MS: m/z 460 (M+1)

Hydrochloride salt of (R)—N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 54 hydrochloride salt)

$^1$H NMR (400 MHz, DMSO-d$_6$): δ 11.59 (brs, 1H, D$_2$O exchangeable), 8.26 (s, 1H, D$_2$O exchangeable), 7.76 (d, J=8.4 Hz, 2H), 7.04 (d, J=8.4 Hz, 2H), 6.98 (s, 1H), 4.99 (brs, 2H, D$_2$O exchangeable), 4.68 (s, 1H), 4.01-3.99 (m, 2H), 2.61-3.52 (m, 17H), 1.53 (t, J=6.0 Hz, 2H), 0.38 (s, 4H)

MS: m/z 460 (M+1)

Hydrochloride salt of (S)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 55 hydrochloride salt)

$^1$H NMR (400 MHz, DMSO-d$_6$): δ 10.93 (brs, 1H, D$_2$O exchangeable), 7.41 (d, J=8.0 Hz, 2H), 7.27 (d, J=8.0 Hz, 2H), 6.92 (s, 1H), 4.62 (s, 1H), 3.76 (brs, 1H, D$_2$O exchangeable), 3.50-3.48 (m, 2H), 3.09-3.03 (m, 2H), 2.85-2.63 (m, 9H), 2.07-2.01 (m, 4H), 1.55 (s, 2H), 0.39 (brs, 4H)

MS: m/z 436 (M+1)

Hydrochloride salt of (R)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 56 hydrochloride salt)

$^1$H NMR (400 MHz, DMSO-d$_6$): δ 10.93 (brs, 1H, D$_2$O exchangeable), 7.41 (d, J=8.0 Hz, 2H), 7.27 (d, J=8.0 Hz, 2H), 6.92 (s, 1H), 4.62 (s, 1H), 3.76 (brs, 1H, D$_2$O exchangeable), 3.50-3.48 (m, 2H), 3.09-3.03 (m, 2H), 2.85-2.63 (m, 9H), 2.07-2.01 (m, 4H), 1.55 (s, 2H), 0.39 (brs, 4H)

MS: m/z 436 (M+1)

Hydrochloride salt of (R)-2'-(3-(4-(5-chloropyridin-2-yl)piperazin-1-yl)cyclopent-1-en-1-yl)-7',8'-dihydro-3'H-spiro[cyclopropane-1,6'-quinazolin]-4'(5'H)-one (Compound 57 hydrochloride salt)

$^1$H NMR (400 MHz, DMSO-d$_6$): δ 11.54 (brs, 1H, D$_2$O exchangeable), 8.17 (d, J=2.8 Hz, 1H), 7.71 (dd, J=2.8 Hz & 8.8 Hz, 1H), 7.02 (d, J=8.8 Hz, 1H), 6.93 (d, J=1.6 Hz, 1H), 5.27 (brs, 2H), 4.65 (brs, 1H), 4.40 (s, 2H), 3.51 (s, 2H), 3.29-3.60 (m, 2H), 3.09-3.03 (m, 2H), 2.86-2.63 (m, 2H), 2.64-2.62 (m, 2H), 2.33-2.28 (m, 2H), 2.25 (s, 2H), 1.54-1.51 (m, 2H), 0.39-0.38 (m, 4H)

MS: m/z 437.8 (M+1)

Hydrochloride salt of (R)-2'-(3-(4-(5-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 58 hydrochloride salt)

$^1$H NMR (400 MHz, DMSO-d$_6$): δ 11.70 (brs, 1H, D$_2$O exchangeable), 8.17 (d, J=2.8 Hz, 1H), 7.66-7.61 (m, 1H), 7.06-7.03 (m, 1H), 6.98 (s, 1H), 4.66 (s, 1H), 4.34 (d, J=9.2 Hz, 2H), 3.54-2.64 (m, 10H), 2.33-2.29 (m, 2H), 2.26 (s, 2H), 1.55-1.53 (m, 2H), 0.39-0.38 (m, 4H)

MS: m/z 422 (M+1)

Hydrochloride salt of (R)-2'-(3-(4-(3,4-dichlorophenyl)piperazin-1-yl)cyclopent-1-en-1-yl)-7',8'-dihydro-3'H-spiro[cyclopropane-1,6'-quinazolin]-4'(5'H)-one (Compound 59 hydrochloride salt)

$^1$H NMR (400 MHz, DMSO-d$_6$): δ 11.53 (brs, 1H, D$_2$O exchangeable), 7.46 (d, J=8.8 Hz, 1H), 7.26 (d, J=3.2 Hz, 1H), 7.02 (dd, J=2.8 Hz & 8.8 Hz, 1H), 6.95 (s, 1H), 4.67 (s, 1H), 3.95 (d, J=12.4 Hz, 2H), 3.51 (brs, 2H), 3.26-3.09 (m, 4H), 2.86-2.76 (m, 2H), 2.67-2.62 (m, 2H), 2.34-2.29 (m, 2H), 2.61 (s, 2H), 1.53 (t, J=6.4 Hz, 2H), 0.39-0.38 (m, 4H)

MS: m/z 471 (M+1)

Hydrochloride salt of (R)-2'-(3-(4-(3-chlorophenyl)piperazin-1-yl)cyclopent-1-en-1-yl)-7',8'-dihydro-3'H-spiro[cyclopropane-1,6'-quinazolin]-4'(5'H)-one (Compound 60 hydrochloride salt)

$^1$H NMR (400 MHz, DMSO-d$_6$): δ 11.20 (brs, 1H, D$_2$O exchangeable), 7.27 (t, J=8.0 Hz, 1H), 7.07 (brs, 1H), 6.97 (dd, J=2.0 Hz & 8.0 Hz, 1H), 6.93 (s, 1H), 6.88 (dd, J=1.6 Hz & 8.0 Hz, 1H), 4.67 (s, 1H), 3.94-3.92 (m, 2H), 3.77 (brs, 2H, D$_2$O exchangeable), 3.52 (s, 2H), 3.20-3.15 (m, 4H), 2.84-2.78 (m, 2H), 2.62-2.60 (m, 2H), 2.35-2.26 (m, 4H), 1.53 (t, J=5.6 Hz, 2H), 0.39-0.38 (m, 4H)

MS: m/z 436.6 (M+1)

Hydrochloride salt of (R)-2'-(3-(4-(2,4-difluorophenyl)piperazin-1-yl)cyclopent-1-en-1-yl)-7',8'-dihydro-3'H-spiro[cyclopropane-1,6'-quinazolin]-4'(5'H)-one (Compound 61 hydrochloride salt)

$^1$H NMR (400 MHz, DMSO-d$_6$): δ 11.68 (brs, 1H, D$_2$O exchangeable), 7.24-7.20 (m, 1H), 7.19-7.12 (m, 1H), 7.06-7.00 (m, 2H), 4.68 (s, 1H), 3.53-3.42 (m, 4H), 3.28-3.16 (m, 4H), 2.86-2.81 (m, 2H), 2.66-2.64 (m, 2H), 2.36-2.30 (m, 2H), 2.26 (s, 2H), 1.52 (t, J=6.4 Hz, 2H), 0.39 (s, 4H)

MS: m/z 439 (M+1)

Hydrochloride salt of (R)-2'-(3-(4-(3,4-difluorophenyl)piperazin-1-yl)cyclopent-1-en-1-yl)-7',8'-dihydro-3'H-spiro[cyclopropane-1,6'-quinazolin]-4'(5'H)-one (Compound 62 hydrochloride salt)

$^1$H NMR (400 MHz, DMSO-d$_6$): δ 11.61 (brs, 1H, D$_2$O exchangeable), 7.35-7.25 (m, 1H), 7.15-7.10 (m, 1H), 6.98 (s, 1H), 6.82-6.80 (m, 1H), 4.67 (s, 1H), 3.85 (d, J=10.8 Hz, 2H), 3.52 (s, 2H), 3.22-3.11 (m, 4H), 2.89-2.80 (m, 2H), 2.66-2.63 (m, 2H), 2.65-2.35 (m, 4H), 1.53 (t, J=6.4 Hz, 2H), 0.40-0.39 (m, 4H)

MS: m/z 439 (M+1)

Hydrochloride salt of (R)-2'-(3-(4-(4-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 63 hydrochloride salt)

$^1$H NMR (400 MHz, DMSO-d$_6$): δ 11.78 (brs, 1H, D$_2$O exchangeable), 7.41 (dd, J=2.4 Hz & 12.4 Hz, 1H), 7.22 (dd, J=1.6 Hz & 8.4 Hz, 1H), 7.13 (t, J=8.8 Hz, 1H), 7.00 (s, 1H), 4.68 (s, 1H), 3.54-3.48 (m, 4H), 3.27-3.17 (m, 4H), 2.88-2.81 (m, 2H), 2.67-2.66 (m, 2H), 2.36-2.32 (m, 2H), 2.26 (s, 2H), 1.53 (t, J=6.0 Hz, 2H), 0.39 (s, 4H)
MS: m/z 455.1 (M+1)

Hydrochloride salt of (R)-2'-(3-(4-(3-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 64 hydrochloride salt)

$^1$H NMR (400 MHz, DMSO-d$_6$): δ 11.60 (brs, 1H, D$_2$O exchangeable), 7.30 (t, J=9.2 Hz, 1H), 7.22-7.20 (m, 1H), 7.03-6.99 (m, 2H), 4.67 (s, 1H), 3.85 (d, J=11.6 Hz, 2H), 3.52 (brs, 2H), 3.19-3.08 (m, 4H), 2.88-2.77 (m, 2H), 2.67-2.64 (m, 2H), 2.36-2.30 (m, 2H), 2.26 (s, 2H), 2.53 (t, J=6.4 Hz, 2H), 0.40-0.39 (m, 4H)
MS: m/z 454.7 (M+1)

Hydrochloride salt of (R)-2'-(3-(4-(2,4-dichlorophenyl)piperazin-1-yl)cyclopent-1-en-1-yl)-7',8'-dihydro-3'H-spiro[cyclopropane-1,6'-quinazolin]-4'(5'H)-one (Compound 65 hydrochloride salt)

$^1$H NMR (400 MHz, DMSO-d$_6$): δ 11.39 (brs, 1H, D$_2$O exchangeable), 7.61 (d, J=2.4 Hz, 1H), 7.41 (dd, J=2.4 Hz & 8.8 Hz, 1H), 7.24 (d, J=8.8 Hz, 1H), 6.97 (s, 1H), 5.80 (brs, 2H, D$_2$O exchangeable), 4.69 (s, 1H), 3.43-3.55 (m, 4H), 3.22-3.13 (m, 4H), 2.82-2.78 (m, 2H), 2.67-2.63 (m, 2H), 2.49-2.29 (m, 2H), 2.26 (s, 2H), 1.51 (t, J=6.4 Hz, 2H), 0.40-0.39 (m, 4H)
MS: m/z 470.7 (M+1)

Hydrochloride salt of (S)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 66 hydrochloride salt)

$^1$H NMR (400 MHz, DMSO-d$_6$): δ 10.91 (brs, 1H, D$_2$O exchangeable), 7.12-6.92 (m, 5H), 5.09 (s, 1H), 4.55 (brs, 2H, D$_2$O exchangeable), 3.65-3.16 (m, 4H), 2.72-2.64 (m, 4H), 2.26 (s, 2H), 1.61-1.33 (m, 12H), 0.39 (s, 4H)
MS: m/z 448.5 (M)

Hydrochloride salt (R)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 67 hydrochloride salt)

$^1$H NMR (400 MHz, DMSO-d$_6$): δ 10.91 (brs, 1H, D$_2$O exchangeable), 7.12-6.92 (m, 5H), 5.09 (s, 1H), 4.55 (brs, 2H, D$_2$O exchangeable), 3.65-3.16 (m, 4H), 2.64-2.72 (m, 4H), 2.26 (s, 2H), 1.61-1.33 (m, 12H), 0.39 (s, 4H)
MS: m/z 448.5 (M)

Hydrochloride salt of (R)-3-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 68 hydrochloride salt)

$^1$H NMR (400 MHz, DMSO-d$_6$): δ 11.49 (brs, 1H, D$_2$O exchangeable), 8.46 (s, 1H, D$_2$O exchangeable), 7.67-7.62 (m, 2H), 7.18-7.14 (m, 1H), 6.95 (s, 1H), 4.68 (s, 1H), 3.76-3.16 (m, 8H), 2.85-2.25 (m, 11H), 1.53 (s, 2H), 0.38 (s, 4H)
MS: m/z 478 (M+1)

Hydrochloride salt of (R)—N,N-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 69 hydrochloride salt)

$^1$H NMR (400 MHz, DMSO-d$_6$): δ 11.85 (brs, 1H, D$_2$O exchangeable), 9.64 (brs, 2H, D$_2$O exchangeable), 7.34 (d, J=8.8 Hz, 2H), 7.06 (s, 1H), 7.03 (d, J=8.8 Hz, 2H), 4.70 (s, 1H), 3.95 (d, J=12.4 Hz, 2H), 3.55-3.53 (m, 2H), 3.36-3.14 (m, 4H), 2.94 (s, 6H), 2.90-2.68 (m, 4H), 2.37-2.27 (m, 4H), 1.54 (t, J=6.0 Hz, 2H), 0.40-0.39 (m, 4H)
MS: m/z 474 (M+1)

Hydrochloride salt of (R)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 70 hydrochloride salt)

$^1$H NMR (400 MHz, DMSO-d$_6$): δ 10.50 (brs, 1H, D$_2$O exchangeable), 7.13-7.09 (m, 2H), 7.03-7.00 (m, 2H), 6.96 (s, 1H), 5.32 (brs, 2H, D$_2$O exchangeable), 4.23 (s, 1H), 3.65-3.72 (m, 3H), 3.50 (brs, 1H), 3.40-3.23 (m, 4H), 2.80-2.61 (m, 4H), 2.26 (s, 2H), 1.53 (t, J=6.0 Hz, 2H), 1.43 (s, 3H), 1.20 (s, 3H), 0.39-0.38 (m, 4H)
MS: m/z 449.1 (M+1)

Hydrochloride salt of (S)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 71 hydrochloride salt)

$^1$H NMR (400 MHz, DMSO-d$_6$): δ 11.50 (brs, 1H, D$_2$O exchangeable), 7.15-7.04 (m, 2H), 7.05-7.03 (m, 2H), 6.96 (s, 1H), 4.23 (s, 1H), 3.72-3.65 (m, 3H), 3.50 (brs, 1H), 3.40-3.23 (m, 4H), 2.80-2.61 (m, 4H), 2.26 (s, 2H), 1.53 (t, J=6.0 Hz, 2H), 1.43 (s, 3H), 1.20 (s, 3H), 0.40-0.39 (m, 4H)
MS: m/z 449.1 (M+1)

Hydrochloride salt of (R)—N-methyl-4-(1-(3-(4'-oxo-4',5',7',8'-tetrahydro-3'H-spiro[cyclopropane-1,6'-quinazolin]-2'-yl)cyclopent-2-en-1-yl)-1,2,3,6-tetrahydropyridin-4-yl)benzamide (Compound 72 hydrochloride salt)

$^1$H NMR (400 MHz, DMSO-d$_6$): δ 11.02 (brs, 1H, D$_2$O exchangeable), 8.50 (brs, 1H, D$_2$O exchangeable), 7.86 (d, J=8.4 Hz, 2H), 7.59 (d, J=8.4 Hz, 2H), 6.95 (d, J=20.8 Hz, 1H), 6.35 (s, 1H), 4.73 (brs, 1H), 4.63 (brs, 1H, D$_2$O exchangeable), 3.90-3.60 (m, 3H), 3.20 (s, 1H), 2.91-2.26 (m, 13H), 1.53 (t, J=6.0 Hz, 2H), 0.40-0.39 (m, 4H)
MS: m/z 457.1 (M+1)

Hydrochloride salt of (R)-2'-(3-(4-(p-tolyl)piperazin-1-yl)cyclopent-1-en-1-yl)-7',8'-dihydro-3'H-spiro[cyclopropane-1,6'-quinazolin]-4'(5'H)-one (Compound 73 hydrochloride salt)

$^1$H NMR (400 MHz, DMSO-d$_6$): δ 11.25 (brs, 1H, D$_2$O exchangeable), 7.07 (d, J=8.4 Hz, 2H), 6.94 (s, 1H), 6.91 (d, J=8.4 Hz, 2H), 6.60 (brs, 2H, D$_2$O exchangeable), 4.67 (s, 1H), 3.77 (d, J=11.6 Hz, 2H), 3.51 (s, 2H), 3.16-2.50 (m, 8H), 2.33-2.26 (m, 4H), 2.21 (s, 3H), 1.51 (t, J=6.0 Hz, 2H), 0.40-0.39 (m, 4H)
MS: m/z 416.5 (M)

Hydrochloride salt of (R)-2'-(3-(4-(4-methoxyphenyl)piperazin-1-yl)cyclopent-1-en-1-yl)-7',8'-dihydro-3'H-spiro[cyclopropane-1,6'-quinazolin]-4'(5'H)-one (Compound 74 hydrochloride salt)

$^1$H NMR (400 MHz, DMSO-d6): δ11.43 (brs, 1H, D2O exchangeable), 7.00 (d, J=9.2 Hz, 2H) 6.99 (s, 1H), 6.88 (d, J=9.2 Hz, 2H), 4.68 (brs, 1H), 3.69 (s, 3H), 3.68-3.50 (m, 4H) 3.40-3.15 (m, 4H) 2.90-2.60 (m, 4H) 2.35-2.26 (m, 4H) 1.54 (t, J=5.2 Hz, 2H) 0.40 (s, 4H)

MS: m/z 433.3 (M+1)

Hydrochloride salt of (R)-2'-(3-(4-(4-fluorophenyl)piperidin-1-yl)cyclopent-1-en-1-yl)-7',8'-dihydro-3'H-spiro[cyclopropane-1,6'-quinazolin]-4'(5'H)-one (Compound 75 hydrochloride salt)

$^1$H NMR (400 MHz, DMSO-d$_6$) δ 11.24 (brs, 1H, D$_2$O exchangeable) 7.27 (dd, J=6.4 Hz, 2H), 7.15 (dd, J=6.4 Hz, 2H), 6.92 (s, 1H), 4.66-4.59 (m, 1H), 3.10-3.06 (m, 2H), 2.81-2.72 (m, 2H), 2.65-2.60 (m, 2H), 2.35-2.30 (m, 1H), 2.27-2.22 (m, 3H), 2.02-1.97 (m, 3H), 1.52 (t, J=6.0 Hz, 2H), 1.07 (t, J=6.4 Hz, 4H), 0.38 (d, J=6.2 Hz, 4H).

MS: m/z 420 (M+1)

Hydrochloride salt of (R)—N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 76 hydrochloride salt)

$^1$H NMR (400 MHz, DMSO-d$_6$) δ 11.72 (brs, 1H, D2O exchangeable) 8.62 (d, J=2.0 Hz, 1H), 8.49 (d, J=4.0 Hz, 1H), 8.12 (dd, J=2.0, & 9.2 Hz, 1H), 7.12 (d, J=9.2 Hz, 1H) 6.93 (s, 1H) 4.65-4.59 (m, 3H), 3.54-3.48 (m, 4H), 3.16-3.11 (m, 2H), 2.85-2.63 (m, 7H), 2.49-2.31 (m, 4H) 1.53 (t, J=5.6 Hz, 2H), 0.39 (d, J=3.6 Hz, 4H)

M/z 461 (M+1)

Hydrochloride salt of (R)-2'-(3-(4-(p-tolyl)piperidin-1-yl)cyclopent-1-en-1-yl)-7',8'-dihydro-3'H-spiro[cyclopropane-1,6'-quinazolin]-4'(5'H)-one (Compound 77 hydrochloride salt)

$^1$H NMR (400 MHz, DMSO-d$_6$): δ 11.03 (brs, 1H, D$_2$O exchangeable), 7.14-7.11 (m, 4H), 6.95-6.92 (m, 1H), 4.62-4.60 (m, 1H), 3.48-3.45 (m, 2H), 3.06-3.02 (m, 2H), 2.82-2.79 (m, 3H), 2.83-2.81 (m, 2H) 2.63-2.61 (m, 2H), 2.27-2.25 (m, 5H), 2.20-1.90 (m, 4H), 1.54 (t, J=8 Hz, 4 Hz 2H), 0.40-0.39 (m, 4H)

MS: m/z 416.2 (M+1)

Hydrochloride salt of (R)-2'-(3-(4-(3-fluorophenyl)piperazin-1-yl)cyclopent-1-en-1-yl)-7',8'-dihydro-3'H-spiro[cyclopropane-1,6'-quinazolin]-4'(5'H)-one (Compound 78 hydrochloride salt)

$^1$H NMR (400 MHz, DMSO-d$_6$) δ 11.57 (brs-exchanges with D$_2$O, 1H), 7.33-7.22 (m, 1H), 6.99-6.84 (m, 1H), 6.92-6.80 (m, 2H), 6.67-6.62 (m, 1H), 4.72-4.65 (m, 1H), 3.93 (d, J=11.9 Hz, 2H), 3.54 (d, J=6.0 Hz, 1H), 3.27-3.06 (m, 4H), 2.95-2.69 (m, 3H), 2.65 (d, J=6.4 Hz, 2H), 2.38-2.24 (m, 4H), 1.54 (t, J=6.3 Hz, 2H), 0.40 (d, J=4.2 Hz, 4H).

MS: m/z 421 (M+1)

Hydrochloride salt of (R)-2'-(3-(4-(2-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 79 hydrochloride salt)

$^1$H NMR (400 MHz, DMSO-d$_6$) δ 11.57 (bs-exchanges with D2O, 1H), 7.50-7.47 (m, 1H), 7.29-7.21 (m, 1H), 6.98-6.97 (m, 1H), 6.64 (td, J=8.4, 2.3 Hz, 1H), 4.72-4.65 (m, 1H), 3.93 (d, J=11.9 Hz, 2H), 3.54 (d, J=6.0 Hz, 2H), 3.27-3.06 (m, 4H), 2.95-2.69 (m, 2H), 2.65 (d, J=6.4 Hz, 2H), 2.38-2.24 (m, 4H), 1.54 (t, J=6.3 Hz, 2H), 0.40 (d, J=4.2 Hz, 4H).

MS: m/z 455 (M+1)

Hydrochloride salt of (R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 80 hydrochloride salt)

$^1$H NMR (400 MHz, DMSO-d6) δ 11.63 (s, 1H, D2O exchangeable), 7.25 (d, J=8.3 Hz, 1H), 7.00 (s, 2H), 6.86 (d, J=8.5 Hz, 1H), 4.75-4.60 (m, 1H), 3.92-3.75 (m, 2H), 3.62-3.44 (m, 2H), 3.30-3.00 (m, 4H), 2.97-2.74 (m, 2H), 2.72-2.56 (m, 2H), 2.41-2.18 (m, 7H), 1.65-1.42 (m, 2H), 0.52-0.20 (m, 4H).

MS: m/z 435 (M+1)

Hydrochloride salt of (R)-2'-(3-(4-(2-methylbenzo[d]thiazol-6-yl)piperazin-1-yl)cyclopent-1-en-1-yl)-7',8'-dihydro-3'H-spiro[cyclopropane-1,6'-quinazolin]-4'(5'H)-one (Compound 81 hydrochloride salt)

$^1$H NMR (400 MHz, DMSO-d6) δ 11.30 (s, 1H), 7.89 (d, J=8.8 Hz, 1H), 7.50 (d, J=2.4 Hz, 1H), 7.19 (dd, J=8.9, 2.4 Hz, 1H), 6.97 (d, J=2.2 Hz, 1H), 4.82-4.58 (m, 1H), 3.57 (d, J=9.5 Hz, 3H), 3.33-3.12 (m, 5H), 2.96-2.72 (m, 5H), 2.64 (t, J=6.2 Hz, 2H), 2.44-2.30 (m, 2H), 2.26 (s, 2H), 1.54 (t, J=6.2 Hz, 2H), 0.39 (s, J=4.2 Hz, 4H).

MS: m/z 474 (M+1)

Hydrochloride salt of (R)-2'-(3-(4-(3-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 82 hydrochloride salt)

$^1$H NMR (400 MHz, DMSO-d$_6$) δ 11.22 (bs-exchanges with D$_2$O, 1H), 7.22 (d, J=8.5 Hz, 1H), 7.06 (d, J=2.5 Hz, 1H), 6.96-6.89 (m, 2H), 4.76-4.61 (m, 1H), 3.86 (d, J=9.7 Hz, 4H), 3.25-3.07 (m, 4H), 2.95-2.79 (m, 2H), 2.74-2.55 (m, 2H), 2.41-2.25 (m, 4H), 2.23 (s, 3H), 1.55 (t, J=6.3 Hz, 2H), 0.41-0.42 (m, 4H).

MS: m/z 451 (M+1)

Hydrochloride salt of (R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 83 hydrochloride salt)

$^1$H NMR (400 MHz, DMSO-d6) δ 10.71 (s, 1H, D$_2$O exchangeable), 7.03 (t, J=9.1 Hz, 1H), 6.92 (d, J=9.4 Hz, 1H), 6.88-6.80 (m, 1H), 4.68 (d, J=7.2 Hz, 1H), 3.77 (d, J=12.7 Hz, 2H), 3.24-3.09 (m, 3H) 3.02 (t, J=12.4 Hz, 2H), 2.92-2.74 (m, 2H), 2.73-2.58 (m, 2H), 2.38-2.30 (m, 2H), 2.26 (s, 3H), 2.20 (s, 3H), 1.53 (t, J=5.8 Hz, 2H), 0.39 (d, J=4.6 Hz, 4H).

MS: m/z 435 (M+1)

Hydrochloride salt of (R)-2'-(3-(4-(3-fluoro-4-methylphenyl)piperazin-1-yl)cyclopent-1-en-1-yl)-7',8'-dihydro-3'H-spiro[cyclopropane-1,6'-quinazolin]-4'(5'H)-one (Compound 84 hydrochloride salt)

$^1$H NMR (400 MHz, DMSO-d$_6$): δ 11.36 (brs, 1H, D$_2$O exchangeable), 7.14 (t, J=8 Hz 1H), 6.95 (m, J=4 Hz 1H), 6.81-6.75 (dd, J=4 Hz 1H), 6.76-6.73 (dd, J=4 Hz 1H), 4.67-4.64 (m, 1H), 3.51-3.49 (m, 2H), 3.16-3.12 (m, 4H), 2.82-2.81 (m, 3H), 2.85-2.83 (m, 2H) 2.64-2.63 (m, 2H), 2.33-2.30 (m 4H), 2.13-2.11 (m, 2H), 1.54 (t, J=8 Hz, 4 Hz, 2H), 0.40-0.39 (m, 4H)

MS: m/z 435.1 (M+1)

Hydrochloride salt of (R)-2'-(3-(4-(m-tolyl)piperazin-1-yl)cyclopent-1-en-1-yl)-7',8'-dihydro-3'H-spiro[cyclopropane-1,6'-quinazolin]-4'(5'H)-one (Compound 85 hydrochloride salt)

$^1$H NMR (400 MHz, DMSO-d$_6$): δ 11.22 (brs, 1H, D$_2$O exchangeable), 7.14 (t, J=8 Hz, 1H), 6.96 (m, J=4 Hz, 1H), 6.84-6.79 (m, 2H), 6.69 (dd, J=4 Hz 1H), 4.68 (s, 1H), 3.51 (brs, 2H), 3.14 (s, 4H), 2.79 (brs, 3H), 2.85 (brs, 4H), 2.62 (m, 2H), 2.33 (s, 4H), 1.54 (t, J=8 Hz, 4 Hz, 2H),0.40-0.39 (m, 4H)

MS: m/z 416.40 (M+1)

Hydrochloride salt of (R)-2'-(3-(4-(4-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 86 hydrochloride salt)

$^1$H NMR (400 MHz, DMSO-d6) δ 11.52 (s, 1H), 7.41 (t, J=8.9 Hz, 1H), 7.10 (dd, J=12.9, 2.8 Hz, 1H), 6.96 (s, J=2.0 Hz, 1H), 6.87 (dd, J=9.0, 2.8 Hz, 1H), 4.71-4.63 (m, 1H), 3.51 (dd, J=11.0, 5.8 Hz, 2H), 3.31-3.02 (m, 5H), 2.82 (m, J=17.1, 8.5 Hz, 3H), 2.64 (t, J=6.3 Hz, 2H), 2.32 (q, J=7.1 Hz, 2H), 2.26 (s, 2H), 1.53 (t, J=6.3 Hz, 2H), 0.39 (s, J=4.3 Hz, 4H).

MS: 455 (M+1)

Hydrochloride salt of (R)—N-methyl-3-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 87 hydrochloride salt)

$^1$H NMR (400 MHz, DMSO-d$_6$) δ 11.47 (bs-exchanges with D$_2$O, 1H), 8.49 (q, J=4.4 Hz, exchanges with D$_2$O, 1H), 7.48-7.42 (m, 1H), 7.39-7.29 (m, 2H), 7.11-7.21 (m, 1H), 7.02-6.96 (m, 1H), 4.72-4.65 (m, 1H), 3.97-3.89 (m, 2H), 3.18 (d, J=12.3 Hz, 6H), 2.95-2.74 (m, 5H), 2.69-2.61 (m, 2H), 2.39-2.24 (m, 4H), 1.54 (t, J=6.2 Hz, 2H), 0.39 (d, J=3.8 Hz, 4H).

MS: m/z 460 (M+1)

Hydrochloride salt of (R)-2'-(3-(4-(2-fluoro-4-methylphenyl)piperazin-1-yl)cyclopent-1-en-1-yl)-7',8'-dihydro-3'H-spiro[cyclopropane-1,6'-quinazolin]-4'(5'H)-one (Compound 88 hydrochloride salt)

$^1$H NMR (400 MHz, DMSO-d$_6$): δ 10.99 (brs, 1H, D$_2$O exchangeable), 7.06-6.92 (m, J=8 Hz, 4H), 4.69 (s, 1H), 3.50 (brs, 4H), 3.18 (brs, 4H), 2.82 (s, 2H), 2.62 (s, 3H), 2.54 (s, 2H) 2.34 (brs, 4H), 1.51 (t, J=8 Hz, 4 Hz, 2H), 0.40-0.39 (m, 4H)

MS: m/z 435.04 (M+1)

Hydrochloride salt of (R)-2'-(3-(4-(o-tolyl)piperazin-1-yl)cyclopent-1-en-1-yl)-7',8'-dihydro-3'H-spiro[cyclopropane-1,6'-quinazolin]-4'(5'H)-one (Compound 90 hydrochloride salt)

$^1$H NMR (400 MHz, DMSO-d$_6$) δ 11.63 (s, 1H, D$_2$O exchangeable), 7.30-7.15 (m, 2H), 7.14-6.97 (m, 3H), 4.84-4.57 (m, 1H), 3.63-3.42 (m, 2H), 3.34-3.05 (m, 5H), 3.02-2.77 (m, 2H), 2.78-2.61 (m, 2H), 2.42-2.16 (m, 5H), 2.14 (s, 3H), 1.65-1.44 (m, 2H), 0.51-0.22 (m, 4H).

MS: m/z 416.41 (M+)

Hydrochloride salt of (R)-2'-(3-(4-(2-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 92 hydrochloride salt)

$^1$H NMR (400 MHz, DMSO-d$_6$): δ 11.35 (brs, 1H, D$_2$O exchangeable), 7.29 (d, J=8 Hz, 1H), 7.13 (s, 2H), 6.98 (s, 1H,), 4.70 (s, 1H), 3.55 (s, 2H), 3.40 (brs, 2H) 3.18 (brs, 4H), 2.88-2.80 (m, 2H), 2.63 (m, 2H), 2.33 (s, 2H), 2.26 (brs, 5H), 1.55 (t, J=4 Hz, 2H), 0.40 (m, 4H)

MS: m/z 452.0 (M+1)

Hydrochloride salt of (R)-2'-(3-(4-(2-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 93 hydrochloride salt)

$^1$H NMR (400 MHz, DMSO-d$_6$): δ 11.25 (brs, 1H, D$_2$O exchangeable), 7.69 (m, 1H), 7.39 (d, J=8 Hz, 1H), 7.16 (d, J=8 Hz, 1H), 6.96 (d, J=4 Hz, 1H), 4.71 (m, 1H), 3.52 (m, 4H), 3.21 (m, 2H), 2.86-2.81 (m, 2H) 2.64 (m, 2H), 2.35 (m, 2H), 2.26 (m, 2H), 1.54 (t, J=4 Hz, 2H), 1.30 (m, 2H), 0.40 (m, 4H)

MS: m/z 455.0 (M+1)

Hydrochloride salt of (R)-2'-(3-(4-(4-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 95 hydrochloride salt)

$^1$H NMR (400 MHz, DMSO-d$_6$) δ 11.19 (s, 1H, D$_2$O exchangeable), 7.12-7.05 (m, 2H), 7.04-6.95 (m, 2H), 4.74-4.65 (m, 1H), 3.50 (d, J=10.3 Hz, 2H), 3.29-3.01 (m, 6H), 2.96-2.73 (m, 2H), 2.71-2.59 (m, 2H), 2.39-2.16 (m, 7H), 1.54 (t, J=6.3, 4.9 Hz, 2H), 0.39 (d, J=4.2 Hz, 4H).

MS: m/z 435 (M+1)

Hydrochloride salt of (R)-2'-(3-(4-(4-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 96 hydrochloride salt)

$^1$H NMR (400 MHz, DMSO-d$_6$) δ 10.97 (s, 1H, D$_2$O exchangeable), 7.29 (d, J=2.5 Hz, 1H), 7.23 (dd, J=8.5, 2.6 Hz, 1H), 7.07 (d, J=8.5 Hz, 1H), 6.94 (d, J=2.2 Hz, 1H), 4.77-4.63 (m, 1H), 3.54-3.45 (m, 2H), 3.28-3.01 (m, 6H), 2.96-2.72 (m, 2H), 2.62 (t, J=6.4 Hz, 2H), 2.39-2.21 (m, 7H), 1.54 (t, J=6.2 Hz, 2H), 0.39 (d, J=4.4 Hz, 4H).

MS: m/z 451 (M+1)

Hydrochloride salt of (R)-2'-(3-(4-(3-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 99 hydrochloride salt)

$^1$H NMR (400 MHz, DMSO-d$_6$): δ 11.37 (brs, 1H, D$_2$O exchangeable), 7.23 (brs, 3H), 6.95 (brs, 1H), 4.70 (m, 1H), 2.54 (m, 4H), 3.26 (m, 4H), 2.81 (m, 2H) 2.63 (m, 2H) 2.34 (m, 4H), 1.55 (t, J=4 Hz, 2H), 0.40-0.39 (m, 4H)

MS: m/z 455.0 (M+1)

Hydrochloride salt of (R)-2'-(3-(4-(2,3-difluorophenyl)piperazin-1-yl)cyclopent-1-en-1-yl)-7',8'-dihydro-3'H-spiro[cyclopropane-1,6'-quinazolin]-4'(5'H)-one (Compound 100 hydrochloride salt)

$^1$H NMR (400 MHz, DMSO-d$_6$) δ 11.66 (s, 1H, D$_2$O exchangeable), 7.20-7.04 (m, 2H), 7.01-6.92 (m, 2H), 4.81-4.64 (m, 1H), 3.66-3.46 (m, 4H), 3.36-3.18 (m, 4H), 2.97-2.75 (m, 2H), 2.71-2.60 (m, 2H), 2.42-2.20 (m, 4H), 1.54 (t, J=6.3 Hz, 2H), 0.40 (d, J=4.2 Hz, 4H).

MS: m/z 439 (M+1)

Hydrochloride salt of (R)-2'-(3-(4-(3-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 108 hydrochloride salt)

$^1$H NMR (400 MHz, DMSO-d$_6$) δ 11.42 (s, 1H, D$_2$O exchangeable), 7.22 (q, J=7.8 Hz, 1H), 7.00 (d, J=2.1 Hz, 1H), 6.97-6.87 (m, 2H), 4.79-4.62 (m, 1H), 3.61-3.43 (m, 2H), 3.37-3.10 (m, 6H), 3.02-2.74 (m, 2H), 2.72-2.58 (m, 2H), 2.34 (q, J=6.8 Hz, 2H), 2.27 (s, 2H), 2.18 (d, J=2.4 Hz, 3H), 1.54 (t, J=6.3 Hz, 2H), 0.40 (d, J=4.2 Hz, 4H).

MS: m/z 435 (M+1)

Hydrochloride salt of (R)-2'-(3-(4-(2,6-difluorophenyl)piperazin-1-yl)cyclopent-1-en-1-yl)-7',8'-dihydro-3'H-spiro[cyclopropane-1,6'-quinazolin]-4'(5'H)-one (Compound 110 hydrochloride salt)

$^1$H NMR (400 MHz, DMSO-d$_6$) δ 10.93 (s, 1H), 7.26-7.04 (m, 3H), 6.93 (s, 1H), 4.78-4.59 (m, 1H), 3.45-3.30 (m, 4H), 3.24-3.05 (m, 3H), 2.94-2.72 (m, 3H), 2.62 (t, J=6.4 Hz, 2H), 2.44-2.23 (m, 4H), 1.53 (t, J=6.3 Hz, 2H), 0.39 (d, J=4.3 Hz, 4H).

MS: m/z 439 (M+1)

Hydrochloride salt of (R)-3-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl) benzonitrile (Compound 111 hydrochloride salt)

$^1$H NMR (400 MHz, DMSO-d$_6$) δ 10.51 (bs, 1H, D$_2$O exchangeable), 7.81 (d, J=13.1 Hz, 1H), 7.65 (d, J=8.5 Hz, 1H), 7.27 (t, J=8.6 Hz, 1H), 6.88 (s, 1H), 4.73 (m, 1H), 3.85-3.70 (m, 2H), 3.41-3.36 (m, 2H), 3.30-3.15 (m, 4H), 2.85-2.75 (m, 2H), 2.65-2.55 (m, 2H), 2.40-2.30 (m, 2H), 2.26 (s, 2H), 1.54 (t, J=6.1 Hz, 2H), 0.42-0.36 (m, 4H).

MS: m/z 446 (M+1)

Hydrochloride salt of (R)-2'-(3-(4-(4-fluoro-3-methoxyphenyl)piperazin-1-yl)cyclopent-1-en-1-yl)-7',8'-dihydro-3'H-spiro[cyclopropane-1,6'-quinazolin]-4'(5'H)-one (Compound 114 hydrochloride salt)

$^1$H NMR (400 MHz, DMSO-d$_6$): δ 11.27 (brs, 1H, D$_2$O exchangeable), 7.08 (dd, J=8 Hz, 1H), 6.97 (t, J=4 Hz, 1H), 6.79 (dd, J=8 Hz, 1H), 6.51-6.48 (m, 1H) 5.47 (brs, 2H, D$_2$O exchangeable), 4.70-4.67 (m, 1H), 3.80 (s, 3H), 3.54-3.51 (m, 2H), 3.16-3.12 (m, 4H), 3.14-3.12 (m, 2H) 2.86-2.81 (m, 2H) 2.65-2.62 (m, 2H) 2.36-2.30 (m, 2H) 2.26 (s, 2H) 1.54 (t, J=6.4 Hz, 2H) 0.40-0.39 (m, 4H)

MS: m/z 451 (M+1)

Hydrochloride salt of (R)-2'-(3-(4-(2-chlorophenyl) piperazin-1-yl)cyclopent-1-en-1-yl)-7',8'-dihydro-3'H-spiro[cyclopropane-1,6'-quinazolin]-4'(5'H)-one (Compound 122 hydrochloride salt)

$^1$H NMR (400 MHz, DMSO-d$_6$): δ 11.36 (brs, 1H, D$_2$O exchangeable), 7.47 (dd, J=8 Hz, 4 Hz 1H), 7.35 (m, 1H), 7.22 (dd, J=8 Hz, 4 Hz 1H), 7.12 (m, 1H), 6.98 (m, 1H), 4.71 (m, 1H), 3.56 (t, J=12 Hz, 2H), 3.46 (m, 2H,) 3.19 (m, 4H), 2.85 (m, 2H), 2.83 (m, 2H), 2.64 (m, 2H), 2.43-2.24 (m, 4H), 1.54 (t, J=8 Hz, 2H), 0.40-0.39 (m, 4H)

MS: m/z 437 (M+1)

Hydrochloride salt of (R)-2-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl) benzonitrile (Compound 127 hydrochloride salt)

$^1$H NMR (400 MHz, DMSO-d$_6$): δ 11.04 (s, 1H, D$_2$O exchangeable), 7.71 (t, J=8.5 Hz, 1H), 7.12 (dd, J=13.7, 2.3 Hz, 1H), 6.97 (dd, J=9.0, 2.4 Hz, 1H), 6.87 (s, 1H), 4.77-4.58 (m, 1H), 4.20 (d, J=14.2 Hz, 2H), 3.59-3.46 (m, 2H), 3.33 (t, J=13.4 Hz, 2H), 3.22-3.02 (m, 2H), 2.97-2.71 (m, 2H), 2.60 (t, 2H), 2.39-2.16 (m, 4H), 1.53 (t, J=6.3 Hz, 2H), 0.39 (d, J=4.4 Hz, 4H).

MS: m/z 446 (M+1)

Hydrochloride salt of (R)-2'-(3-(4-(3-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 143 hydrochloride salt)

$^1$H NMR (400 MHz, DMSO-d6) δ 11.05 (s, J=8.5 Hz, 1H), 7.26-7.19 (m, 2H), 7.07 (dd, J=6.6, 2.7 Hz, 1H), 6.95 (d, J=2.3 Hz, 1H), 4.71 (s, 1H), 3.52 (d, J=10.9 Hz, 2H), 3.30-3.07 (m, 6H), 2.93-2.77 (m, 2H), 2.63 (t, J=6.4 Hz, 3H), 2.29 (d, J=22.4 Hz, 6H), 1.54 (t, J=6.3 Hz, 2H), 0.39 (s, 4H).

MS: m/z 451 (M+1)

EXAMPLE 13

Synthesis of (R)-2-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl) benzamide (compound 89)

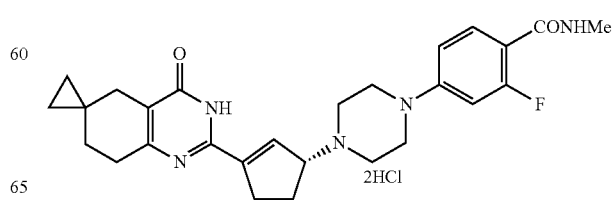

Step 1: (R)-tert-butyl 4-(3-cyanocyclopent-2-en-1-yl)piperazine-1-carboxylate

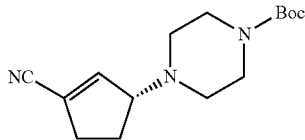 [SMILES: CC(C)(C)OC(=O)N1CCN([C@H]2C=C(C#N)CC2)CC1]

To a stirred solution of tert-butyl piperazine-1-carboxylate (59.5 g, 320 mmol) in dimethyl formamide (400 ml) was added triethylamine (134 ml, 959 mmol) at 25° C. and stirred the reaction mixture for 10 minutes. To this was added 3-bromocyclopent-1-enecarbonitrile (55 g, 320 mmol) and the reaction mixture was stirred for 3 h. The progress of reaction was monitored by TLC. The reaction mixture was then concentrated under reduced pressure. The residue obtained was diluted with water (250 ml) and extracted with ethyl acetate (3×250 ml). The combined organic layer was dried over anhydrous sodium sulphate. The solvent in the organic layer was evaporated under reduced pressure to obtain crude product. The crude product purified by flash column chromatography over silica gel (100-200 mesh) using 40% ethyl acetated in hexane as an eluent to obtain the title compound (35 g, 126 mmol, 39.5% yield).

$^1$H NMR (400 MHz, CDCl$_3$): δ 6.66-6.64 (m, 1H) 3.97-3.93 (m, 1H), 3.45-2.42 (m, 4H), 2.65-2.57 (m, 2H), 2.50-2.40 (m, 4H), 2.11-2.04 (m, 1H) 1.97-1.89 (m, 1H) 1.47 (s, 9H)

MS: m/z 278 (M+1)

A chiral resolution of tert-butyl 4-(3-cyanocyclopent-2-en-1-yl)piperazine-1-carboxylate (30 g) was carried out using chiral column to obtain (R) tert-butyl 4-(3-cyanocyclopent-2-en-1-yl)piperazine-1-carboxylate (12 g) and (S) tert-butyl (3-cyanocyclopent-2-en-1-yl)carbamate (11.5 g).

Step 2: (R)-3-(piperazin-1-yl)cyclopent-1-enecarbonitrile

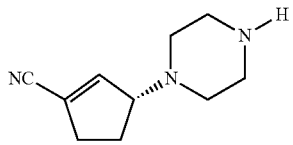 [SMILES: N#CC1=C[C@H](N2CCNCC2)CC1]

To a solution of (R)-tert-butyl 4-(3-cyanocyclopent-2-en-1-yl)piperazine-1-carboxylate (13 g, 46.9 mmol) in dry dichloromethane (30 ml) was added slowly hydrochloric acid 1,4 dioxane (100 ml, 4M solution) in a drop wise manner 0° C. The reaction mixture was stirred at 25° C. for 3 h. The progress of the reaction was monitored by TLC. The reaction mixture was then concentrated under reduced pressure. The residue was diluted with dichloromethane (100 ml) and treated with methanolic ammonia (50 ml, 7M solution) and stirred for 30 minutes. The reaction mixture was then evaporated under reduced pressure to obtain crude product which was purified by flash column chromatography over silica gel (100-200 mesh) using 10% methanol in dichloromethane as an eluent to obtain title compound ((7 g, 84%).

$^1$H NMR (400 MHz, CDCl$_3$): δ 9.20 (s, 1H, D$_2$O exchangeable), 6.94-6.89 (m, 1H), 3.96-3.92 (m, 1H), 3.02-3.00 (m, 4H), 2.72-2.53 (m, 6H), 2.00-1.99 (m, 1H), 1.82-1.74 (m, 1H)

MS: m/z 178 (M+1)

Step 3: (R)-4-(4-(3-cyanocyclopent-2-en-1-yl)piperazin-1-yl)-2-fluoro-N-methylbenzamide

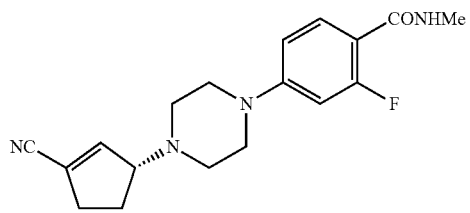

To a mixture of (R)-3-(piperazin-1-yl)cyclopent-1-enecarbonitrile (0.500 g, 2.82 mmol), 4,5-bis(diphenylphosphino)-9,9-dimethylxanthene (XANTPHOS) (0.326 g, 0.564 mmol), palladium (II) acetate (Pd(OAc)$_2$) (63.3 mg, 0.282 mmol) and cesium carbonate (1.838 g, 5.64 mmol) in toluene (15 ml) was added 4-bromo-2-fluoro-N-methylbenzamide (WO2006064251, 0.500 g, 2.82 mmol). The reaction mixture was heated to 110° C. for 16 h. The progress of the reaction was monitored by TLC. The reaction mixture was cooled to 25° C. and filtered through celite. The filtrated was concentrated under reduced pressure to obtain a crude product, which was purified by column chromatography over silica gel (100-200 mesh) using 1-5% methanol in dichloromethane as an eluent to obtain the title compound (0.270 g, 29.1%).

$^1$H NMR (400 MHz, CDCl$_3$): δ 7.50-7.45 (m, 2H), 6.92 (t, J=8.6 Hz, 1H), 6.70 (q, J=2 Hz, 1H), 6.06 (bs, 1H, D$_2$O exchangeable), 4.02-4.00 (m, 1H), 3.34-3.19 (m, 4H), 3.00 (s, 3H), 2.75-2.58 (m, 6H), 2.17-1.98 (m, 2H).

MS: m/z 329 (M+1).

Step 4: Hydrochloride salt of (R)-2-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (compound 89 hydrochloride salt)

The title compound was prepared from (R)-4-(4-(3-cyanocyclopent-2-en-1-yl)piperazin-1-yl)-3-fluoro-N-methylbenzamide using procedure described in step 3 and step 4 of example 1.

$^1$H NMR (400 MHz, DMSO-d$_6$) δ 11.28 (s, 1H, D$_2$O exchangeable), 7.98-7.81 (m, 1H, D$_2$O exchangeable), 7.61 (t, J=9.0 Hz, 1H), 6.96-6.84 (m, 3H), 4.67 (s, 1H), 4.06 (d, J=13.1 Hz, 2H), 3.62-3.44 (m, 2H), 3.34-3.04 (m, 4H), 2.93-2.70 (m, 5H), 2.69-2.55 (m, 2H), 2.39-2.21 (m, 4H), 1.53 (t, J=6.3 Hz, 2H), 0.39 (d, J=4.1 Hz, 4H).

MS: m/z 478 (M+1)

The following compounds were prepared according to the procedure described above in example 13 with appropriate changes in the reactants and reaction conditions.

Hydrochloride salt of (R)-2'-(3-(4-(thiophen-3-yl)piperazin-1-yl)cyclopent-1-en-1-yl)-7',8'-dihydro-3'H-spiro[cyclopropane-1,6'-quinazolin]-4'(5'H)-one (Compound 91 hydrochloride salt)

$^1$H NMR (400 MHz, DMSO-d$_6$) δ 10.95 (bs-exchanges with D2O, 1H), 7.48 (dd, J=5.2, 3.0 Hz, 1H), 7.02 (dd, J=5.3, 1.6 Hz, 1H), 6.92 (d, J=2.2 Hz, 1H), 6.53 (dd, J=3.1, 1.6 Hz, 2H), 4.75-4.65 (m, 1H), 3.69-3.79 (m, 2H), 3.48-3.58 (m, 2H), 3.11-3.26 (m, 2H), 2.99-3.10 (m, 2H), 2.73-2.92 (m, 3H), 2.59-2.69 (m, 3H), 2.31-2.37 (m, 2H), 1.54 (t, J=6.3 Hz, 2H), 0.39 (d, J=3.9 Hz, 4H).

MS: m/z 409 (M+1)

Hydrochloride salt of (R)-2-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 94 hydrochloride salt)

$^1$H NMR (400 MHz, DMSO-d$_6$) δ 11.49 (s, 1H, D$_2$O exchangeable), 8.26-8.03 (m, 1H, D$_2$O exchangeable), 7.34 (d, J=8.5 Hz, 1H), 7.08 (d, J=2.4 Hz, 1H), 6.99 (dd, J=8.6, 2.4 Hz, 1H), 6.94 (s, 1H), 4.77-4.59 (m, 1H), 4.00 (d, J=12.7 Hz, 2H), 3.58-3.44 (m, 2H), 3.31-3.02 (m, 4H), 2.94-2.75 (m, 2H), 2.72 (d, J=4.5 Hz, 3H), 2.67-2.58 (m, 2H), 2.38-2.20 (m, 4H), 1.53 (t, J=6.3 Hz, 2H), 0.39 (d, J=4.1 Hz, 4H).

MS: m/z 494 (M+1)

Hydrochloride salt of (R)—N, 3-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 97 hydrochloride salt)

$^1$H NMR (400 MHz, DMSO-d$_6$) δ 11.44 (s, 1H, D$_2$O exchangeable), 8.37-8.32 (m, 1H, D$_2$O exchangeable), 7.76-7.62 (m, 2H), 7.07 (d, J=8.2 Hz, 1H), 7.00 (s, 1H), 4.77-4.62 (m, 1H), 3.59-3.46 (m, 2H), 3.34-3.13 (m, 6H), 2.98-2.78 (m, 2H), 2.75 (d, J=3.9 Hz, 3H), 2.69-2.60 (m, 2H), 2.42-2.22 (m, 7H), 1.55 (t, 2H), 0.39 (d, J=4.2 Hz, 4H).

MS: m/z 474 (M+1)

Hydrochloride salt of (R)—N, 2-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 98 hydrochloride salt)

$^1$H NMR (400 MHz, DMSO-d$_6$) δ 11.14 (s, 1H, D$_2$O exchangeable), 8.05-7.94 (m, 1H, D$_2$O exchangeable), 7.29 (d, J=8.2 Hz, 1H), 6.93 (s, 1H), 6.90-6.79 (m, 2H), 4.77-4.58 (m, 1H), 4.03-3.86 (m, 2H), 3.30-3.02 (m, 6H), 2.94-2.75 (m, 2H), 2.71 (d, J=4.2 Hz, 3H), 2.66-2.58 (m, 2H), 2.42-2.19 (m, 7H), 1.54 (t, J=6.4 Hz, 2H), 0.39 (d, J=4.2 Hz, 4H).

MS: m/z 474 (M+1)

Hydrochloride salt of (R)-2'-(3-(4-(thiazol-2-yl)piperazin-1-yl)cyclopent-1-en-1-yl)-7',8'-dihydro-3'H-spiro[cyclopropane-1,6'-quinazolin]-4'(5'H)-one (Compound 101 hydrochloride salt)

$^1$H NMR (400 MHz, DMSO-d$_6$) δ 11.23 (s, 1H, D2O exchangeable), 7.26 (d, J=3.6 Hz, 1H), 7.01 (d, J=3.6 Hz, 1H), 6.88 (s, 1H), 4.75-4.63 (m, 1H), 4.08 (d, J=13.6 Hz, 2H), 3.56-3.43 (m, 4H), 3.29-3.10 (m, 3H), 2.95-2.73 (m, 2H), 2.62 (t, J=6.1 Hz, 2H), 2.38-2.20 (m, 3H), 1.53 (t, J=6.3 Hz, 2H), 0.39 (d, J=4.2 Hz, 4H).

MS: m/z 410 (M+1)

Hydrochloride salt of (R)-2'-(3-(4-(4-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 102 hydrochloride salt)

$^1$H NMR (400 MHz, DMSO-d$_6$): δ 12.01 (brs, 1H, D$_2$O exchangeable), 6.93 (q, J=1.8 Hz, 1H), 6.66 (d J=1.3 Hz, 1H), 4.70-4.67 (m, 1H), 4.20-4.16 (m, 2H), 3.72-3.67 (m, 2H), 3.55-3.48 (m, 2H), 3.24-3.20 (m, 2H), 2.90-2.82 (m, 3H), 2.66-2.62 (m, 2H,) 2.35-2.22 (m, 6H), 1.53 (t, J=6.3 Hz, 2H) 0.40-0.39 (m, 4H)

MS: m/z 424 (M+1)

Hydrochloride salt of (R)-5-chloro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 103 hydrochloride salt)

$^1$H NMR (400 MHz, DMSO-d$_6$): δ 11.61 (brs, 1H, D$_2$O exchangeable), 8.70 (d, J=4.0 Hz, 1H), 8.66 (q, J=4.7 Hz, 1H, D$_2$O exchangeable), 8.23 (d, J=4.0 Hz, 1H), 6.97 (q, J=1.8 Hz, 1H), 4.71-4.69 (m, 1H), 4.09-4.06 (m, 2H), 3.68-3.60 (m, 4H) 3.36-3.17 (m, 4H) 2.87-2.81 (m, 4H) 2.64-2.61 (m, 2H) 2.46-2.39 (m, 2H) 2.28 (s, 2H) 1.53 (t, J=6.4 Hz, 2H) 0.41-0.35 (m, 4H)

MS: m/z 495 (M+1)

Hydrochloride salt of (R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-5-carboxamide (Compound 104 hydrochloride salt)

$^1$H NMR (400 MHz, DMSO-d$_6$): δ 11.69 (brs, 1H, D$_2$O exchangeable), 8.37 (q, J=4.4 Hz, 1H, D$_2$O exchangeable), 7.84 (s, 1H), 6.90 (q, J=1.8 Hz, 1H), 4.71-4.69 (m, 1H), 4.11-4.06 (m, 2H), 3.61-3.50 (m, 4H), 3.32-3.13 (m, 2H), 2.87-2.71 (m, 5H), 2.65-2.62 (m, 2H), 2.34-2.26 (m, 4H), 1.53 (t, J=6.4 Hz, 2H) 0.40-0.36 (m, 4H)

MS: m/z 467 (M+1)

Hydrochloride salt of (R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-4-carboxamide (Compound 105 hydrochloride salt)

$^1$H NMR (400 MHz, DMSO-d$_6$): δ 10.68 (brs, 1H, D$_2$O exchangeable), 8.32 (q, J=4.4 Hz, 1H, D$_2$O exchangeable), 7.50 (s, 1H), 6.90 (q, J=1.8 Hz, 1H), 4.70-4.68 (m, 1H), 4.10-4.06 (m, 2H), 3.56-3.50 (m, 4H), 3.36-3.13 (m, 2H) 2.88-2.68 (m, 5H), 2.63-2.60 (m, 2H), 2.31-2.27 (m, 4H), 1.53 (t, J=6.4 Hz, 2H) 0.40-0.38 (m, 4H)

MS: m/z 467 (M+1)

Hydrochloride salt of (R)-2'-(3-(4-(2,5-difluorophenyl)piperazin-1-yl)cyclopent-1-en-1-yl)-7',8'-dihydro-3'H-spiro[cyclopropane-1,6'-quinazolin]-4'(5'H)-one (Compound 106 hydrochloride salt)

$^1$H NMR (400 MHz, DMSO-d$_6$) δ 11.35 (s, 1H, D$_2$O exchangeable), 7.24 (m, 1H), 7.01 (m, 1H), 6.94 (m, 1H), 6.86 (m, 1H,), 4.69 (m, 1H), 3.80-3.50 (m, 6H), 3.27-3.17 (m, 4H), 2.91-2.77 (m, 2H), 2.66-2.62 (m, 2H), 2.45-2.37 (m, 2H), 1.54 (t, J=8 Hz, 2H), 0.40-0.39 (m, 4H).

MS: m/z 439.2 (M+1)

Hydrochloride salt of (R)-2'-(3-(4-(3,5-dichloropyridin-2-yl)piperazin-1-yl)cyclopent-1-en-1-yl)-7',8'-dihydro-3'H-spiro[cyclopropane-1,6'-quinazolin]-4'(5'H)-one (Compound 107 hydrochloride salt)

$^1$H NMR (400 MHz, DMSO-d$_6$): δ 11.23 (brs, 1H, D$_2$O exchangeable), 8.35 (d, J=2.3 Hz, 1H), 8.16 (d, J=2.3 Hz, 1H), 6.93 (d, J=2.4 Hz, 1H), 4.70-4.68 (m, 1H), 3.90-3.87 (m, 2H), 3.37-3.30 (m, 4H) 3.17-3.13 (m, 2H) 2.90-2.81 (m, 2H) 2.63-2.60 (m, 2H) 2.32-2.26 (m, 4H) 1.53 (t, J=6.4 Hz, 2H) 0.40-0.36 (m, 4H)

MS: m/z 473 (M+1)

Hydrochloride salt of (R)-2'-(3-(4-(3,5-difluorophenyl)piperazin-1-yl)cyclopent-1-en-1-yl)-7',8'-dihydro-3'H-spiro[cyclopropane-1,6'-quinazolin]-4'(5'H)-one (Compound 109 hydrochloride salt)

$^1$H NMR (400 MHz, DMSO-d$_6$) δ 11.17 (s, 1H, D$_2$O exchangeable), 6.91 (s, 1H), 6.76 (d, J=10.4 Hz, 2H), 6.60 (t, J=9.2 Hz, 1H), 4.75-4.65 (m, 1H), 4.00 (d, J=12.8 Hz, 2H), 3.30-3.10 (m, 6H), 2.90-2.75 (m, 2H), 2.65-2.60 (m, 2H), 2.35-2.27 (m, 2H), 2.26 (s, 2H) 1.53 (t, J=6.2 Hz, 2H), 0.40-0.39 (m, 4H).

MS: m/z 439 (M+1)

Hydrochloride salt of (R)-5-fluoro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 112 hydrochloride salt)

$^1$H NMR (400 MHz, DMSO-d$_6$): δ 11.82 (brs, 1H, D$_2$O exchangeable), δ 8.61 (brs, 1H, D$_2$O exchangeable), 8.54 (t, J=1.6 Hz, 1H), 7.97 (dd, J=14 Hz, 1.6 Hz, 1H), 6.98 (q, J=4 Hz, 1H), 6.4 (brs, 2H, D$_2$O exchangeable), 4.66-4.68 (m, 1H), 4.30-4.28 (m, 2H), 3.65-3.60 (m, 4H,) 3.24-3.17 (m, 2H), 2.93-2.91 (m, 2H) 2.85 (s, 3H), 2.70-2.61 (m, 2H), 2.37-2.28 (m, 2H,) 2.26 (s, 2H), 1.54 (t, J=6.4 Hz, 2H) 0.40-0.39 (m, 4H)

MS: m/z 479 (M+1)

Hydrochloride salt of (R)-2'-(3-(4-(5-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 113)

$^1$H NMR (400 MHz, DMSO-d$_6$): δ 12.09 (brs, 1H, D$_2$O exchangeable), 7.10 (s, 1H), 6.98 (q, J=4 Hz, 1H), 6.6 (brs, 2H, D$_2$O exchangeable), 4.70-4.67 (m, 1H), 4.14-4.11 (m, 2H), 3.74-3.67 (m, 2H), 3.58-3.53 (m, 2H), 2.92-2.90 (m, 2 H), 2.92-2.75 (m, 2H), 2.66-2.63 (m, 2H), 2.37-2.36 (m, 7H), 1.53 (t, J=6.4 Hz, 2H), 0.40-0.39 (m, 4H)

MS: m/z 425 (M+1)

(R)-2'-(3-(4-(3-chloro-5-fluorophenyl)piperazin-1-yl)cyclopent-1-en-1-yl)-7',8'-dihydro-3'H-spiro[cyclopropane-1,6'-quinazolin]-4'(5'H)-one (Compound 115)

$^1$H NMR (400 MHz, DMSO-d$_6$): δ 11.62 (brs, 1H, D$_2$O exchangeable), 6.97-6.78 (m, 4H), 4.80 (brs, 2H, D$_2$O exchangeable), 4.70-4.67 (m, 1H), 4.00-3.99 (m, 2H), 3.41-3.36 (m, 2H), 3.17-3.11 (m, 2H), 2.93-2.90 (m, 2H), 2.80-2.75 (m, 2H), 2.63-2.66 (m, 2H), 2.35-2.36 (m, 4H), 1.53 (t, J=6.4 Hz, 2H), 0.40-0.39 (m, 4H)

MS: m/z 455 (M+1)

Hydrochloride salt of (R)-2'-(3-(4-(2-fluorophenyl)piperazin-1-yl)cyclopent-1-en-1-yl)-7',8'-dihydro-3'H-spiro[cyclopropane-1,6'-quinazolin]-4'(5'H)-one (Compound 116 hydrochloride salt)

$^1$H NMR (400 MHz, DMSO-d$_6$): δ 11.77 (brs, 1H, D$_2$O exchangeable), δ 7.60 (brs, 2H, D$_2$O exchangeable), 7.22-7.02 (m, 5H,) 4.70-4.68 (m, 1H), 3.40-3.33 (m, 4H), 3.24-3.21 (m, 4H), 2.90-2.86 (m, 2H), 2.82-2.66 (m, 2H), 2.37-2.32 (m, 2H), 2.27 (s, 2H), 1.54 (t, J=6.2 Hz, 2H), 0.42-0.37 (m, 4H)

MS: m/z 421 (M+1)

Hydrochloride salt of (R)-2'-(3-(4-phenylpiperazin-1-yl)cyclopent-1-en-1-yl)-7',8'-dihydro-3'H-spiro[cyclopropane-1,6'-quinazolin]-4'(5'H)-one (Compound 117 hydrochloride salt)

$^1$H NMR (400 MHz, DMSO-d$_6$): δ 11.03 (brs, 1H, D$_2$O exchangeable), 7.32-7.23 (m 2H), 7.05-6.98 (m, 4H), 4.70-4.68 (m, 1H), 3.40-3.33 (m, 4H), 3.24-3.21 (m, 4H), 2.90-2.86 (m, 2H), 2.82-2.66 (m, 2H), 2.37-2.32 (m, 2H), 2.27 (s, 2H) 1.54 (t, J=6.2 Hz, 2H,) 0.42-0.37 (m, 4H)

MS: m/z 403 (M+1)

Hydrochloride salt of (R)-2'-(3-(4-(5-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 123 hydrochloride salt)

$^1$H NMR (400 MHz, DMSO-d$_6$) δ 11.12 (s, 1H, D$_2$O exchangeable), 7.22 (t, J=8.3, 6.9 Hz, 1H), 6.99-6.94 (m, 1H), 6.92-6.81 (m, 2H), 4.73-4.71 (m, 1H), 3.51 (d, J=11.0 Hz, 2H), 3.33-3.06 (m, 6H), 2.96-2.72 (m, 2H), 2.64 (t, J=7.4, 6.4 Hz, 2H), 2.40-2.17 (m, 7H), 1.54 (t, J=6.3 Hz, 2H), 0.39 (d, J=4.1 Hz, 4H).

MS: m/z 410 (M+1)

Hydrochloride salt of (R)-2'-(3-(4-(5-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 124 hydrochloride salt)

$^1$H NMR (400 MHz, DMSO-d$_6$): δ 11.51 (s, 1H, D$_2$O exchangeable), 8.02-7.96 (m, 1H), 7.82 (s, 1H), 7.26 (s, 1H), 6.89 (d, J=2.4 Hz, 1H), 4.75-4.66 (m, 1H), 4.47 (d, J=14.0 Hz, 2H), 3.54-2.43 (m, 4H), 3.16 (m, 2H), 2.91-2.72 (m, 2H), 2.62 (t, J=6.3 Hz, 2H), 2.39-2.24 (m, 4H), 2.3 (s, 3H), 1.53 (t, J=6.3 Hz, 2H), 0.39 (d, J=4.1 Hz, 4H).

MS: m/z 417 (M+)

Hydrochloride salt of (R)-2'-(3-(4-(4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 125 hydrochloride salt)

$^1$H NMR (400 MHz, DMSO-d$_6$): δ 11.67 (brs, 1H, D$_2$O exchangeable), 8.01 (dd, J=4 Hz 1H), 7.26 (m, 1H), 6.89 (m, 2H), 4.68 (m, 1H), 4.55 (dd, J=12 Hz, 2H), 3.59 (m, 3H) 3.17 (m, 1H), 2.79 (m, 3H), 2.55 (m, 2H) 2.26-2.35 (m, 6H), 1.55 (t, J=8 Hz, 2H), 0.40-0.39 (m, 4H)

MS: m/z 437.1 (M+1)

Hydrochloride salt of (R)-2'-(3-(4-(3-fluoro-5-methylphenyl)piperazin-1-yl)cyclopent-1-en-1-yl)-7',8'-dihydro-3'H-spiro[cyclopropane-1,6'-quinazolin]-4'(5'H)-one (Compound 126 hydrochloride salt)

$^1$H NMR (400 MHz, DMSO-d$_6$) δ 11.41 (s, 1H, D$_2$O exchangeable), 6.95 (s, 1H), 6.72-6.63 (m, 2H), 6.49 (d, J=9.0 Hz, 1H), 4.72-4.62 (m, 1H), 3.91 (d, J=11.7 Hz, 2H), 3.57-3.44 (m, 2H), 3.25-3.05 (m, 4H), 2.93-2.73 (m, 2H), 2.69-2.60 (m, 2H), 2.38-2.22 (m, 7H), 1.54 (t, J=6.2 Hz, 2H), 0.39 (d, J=4.0 Hz, 4H).

MS: m/z 435 (M+1)

Hydrochloride salt of (R)-2'-(3-(4-(pyrimidin-2-yl)piperazin-1-yl)cyclopent-1-en-1-yl)-7',8'-dihydro-3'H-spiro[cyclopropane-1,6'-quinazolin]-4'(5'H)-one (Compound 128 hydrochloride salt)

$^1$H NMR (400 MHz, DMSO-d$_6$) δ 11.74 (brs, 1H, D$_2$O exchangeable), 8.46 (d, J=4.7 Hz, 2H), 7.00-6.88 (m, 1H), 6.77 (t, J=4.8 Hz, 1H), 4.87-4.58 (m, 3H), 3.59-3.34 (m, 4H), 3.19-2.69 (m, 3H), 2.69-2.56 (m, 2H), 2.40-2.11 (m, 4H), 1.53 (t, J=6.2 Hz, 2H), 1.29-0.96 (m, 1H), 0.40-0.35 (m, 4H).
MS: m/z 405.1 (M+1)

Hydrochloride salt of (R)-2'-(3-(4-(2-methylpyridin-3-yl)piperazin-1-yl)cyclopent-1-en-1-yl)-7',8'-dihydro-3'H-spiro[cyclopropane-1,6'-quinazolin]-4'(5'H)-one (Compound 129 hydrochloride salt)

$^1$H NMR (400 MHz, DMSO-d$_6$) δ 12.01 (s, 1H, D$_2$O exchangeable), 8.46 (dd, J=5.7 &1.2 Hz, 1H), 8.21 (dd, J=8.5 &1.2 Hz, 1H), 7.85 (dd, J=8.3 & 5.7 Hz, 1H), 7.01-6.99 (m, 1H), 4.75-4.66 (m, 1H), 3.59-3.50 (m, 2H), 3.49-3.33 (m, 4H), 3.32-3.25 (m, 2H), 2.99-2.75 (m, 4H), 2.69-2.61 (m, 2H), 2.48-2.28 (m, 3H), 2.27 (s, 2H), 1.54 (t, J=6.3 Hz, 2H), 0.40-0.37 (m, 4H).
MS: m/z 418.0 (M+1)

Hydrochloride salt of (R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)isonicotinamide (Compound 130 hydrochloride salt)

$^1$H NMR (400 MHz, DMSO-d$_6$): δ 11.93 (bs, exchanges with D$_2$O, 1H), 9.09 (bs, exchanges with D$_2$O, 1H), 8.21 (d, J=8.0 Hz, 1H), 7.67 (s, 1H), 7.21 (d, J=8.0 Hz, 1H), 6.98 (s, 1H), 4.68-4.62 (m, 2H), 3.62-3.33 (m, 4H), 3.42-3.21.42 (m, 2H), 2.88-2.56 (m, 6H), 2.54-2.48 (m, 2H), 2.32-2.25 (m, 4H), 1.54-1.48 (m, 2H), 0.50-0.40 (m, 4H).
MS: m/z 461 (M+1)

Hydrochloride salt of (R)—N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 131 hydrochloride salt)

$^1$H NMR (400 MHz, DMSO-d$_6$): δ 11.75 (bs, exchanges with D$_2$O, 1H), 8.52 (bs, exchanges with D$_2$O, 1H), 8.27 (dd, J=8.0, 4.0 Hz, 1H), 7.83 (dd, J=8.0, 4.0 Hz, 1H), 7.10-6.96 (m, 2H), 4.66 (s, 1H), 3.84-3.76 (m, 2H), 3.56-3.42 (m, 4H), 3.10-3.22 (m, 2H), 2.90-2.72 (m, 5H), 2.72-2.65 (m, 2H), 2.35-2.21 (m, 4H), 1.57-1.50 (m, 2H), 0.42-0.37 (m, 4H)
MS: m/z 461 (M+1)

Hydrochloride salt of (R)-2'-(3-(4-(3-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 132 hydrochloride salt)

$^1$H NMR (400 MHz, DMSO-d$_6$) δ 11.33 (s, 1H, D$_2$O exchangeable), 8.17 (dd, J=5.4 &1.8 Hz, 2H), 7.74 (d, J=7.4 Hz, 2H), 7.12 (dd, J=7.4 & 5.0 Hz), 6.96 (d, J=2.7 Hz, 1H), 4.72-4.68 (m, 1H), 3.70-3.50 (m, 4H), 3.40-3.20 (m, 4H), 3.00-2.50 (m, 4H), 2.35-2.25 (m, 7H), 1.54 (t, J=6.3 Hz, 2H), 0.39-0.37 (m, 4H).
MS: m/z 418.1 (M+1)

Hydrochloride salt of (R)-2'-(3-(4-(4-fluoro-2-methoxyphenyl)piperazin-1-yl)cyclopent-1-en-1-yl)-7',8'-dihydro-3'H-spiro[cyclopropane-1,6'-quinazolin]-4'(5'H)-one (Compound 133 hydrochloride salt)

$^1$H NMR (400 MHz, DMSO-d$_6$): δ 11.31 (brs, 1H, D$_2$O exchangeable), 6.97 (m, J=4 Hz, 3H), 6.72 (m, 1H), 4.68 (m, 1H), 3.80 (s, 3H), 3.46 (m, 3H), 3.19 (m, 3H), 2.83 (m, 2H), 2.64 (m, 2H), 2.33 (m, 4H), 2.13 (m, 2H), 1.54 (t, J=8 Hz, 4 Hz, 2H), 0.40-0.39 (m, 4H)
MS: m/z 451 (M+1)

Hydrochloride salt of (R)-3-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 134 hydrochloride salt)

$^1$H NMR (400 MHz, DMSO-d$_6$) δ 11.38 (brs, —Exchanges with D$_2$O, 1H), 8.49-8.57 (m, 1H), 7.93 (d, J=2.0 Hz, 1H), 7.83 (dd, J=8.4, 2.1 Hz, 1H), 7.28 (d, J=8.4 Hz, 1H), 6.97 (d, J=2.3 Hz, 1H), 4.76-4.67 (m, 1H), 3.62-3.52 (m, 4H), 3.31-3.17 (m, 4H), 2.96-2.73 (m, 5H), 2.69-2.60 (m, 2H), 2.39-2.24 (m, 4H), 1.54 (t, J=6.3 Hz, 2H), 0.39 (d, J=4.0 Hz, 4H).
MS: m/z 494 (M+1)

Hydrochloride salt of (R)-2'-(3-(4-(5-ethylpyrimidin-2-yl)piperazin-1-yl)cyclopent-1-en-1-yl)-7',8'-dihydro-3'H-spiro[cyclopropane-1,6'-quinazolin]-4'(5'H)-one (Compound 135 hydrochloride salt)

$^1$H NMR (400 MHz, DMSO-d$_6$) δ 11.40 (brs, 1H, D$_2$O exchangeable), 8.34 (d, J=6.7 Hz, 2H), 6.90 (s, 1H), 4.73 (d, J=13.9 Hz, 2H), 4.65 (d, J=7.8 Hz, 1H), 3.53-3.49 (m, 2H), 3.48-3.23 (m, 2H), 3.12-2.94 (m, 2H), 2.81-2.59 (m, 2H), 2.52-2.48 (m, 2H), 2.26 (s, 2H), 1.53 (t, J=6.3 Hz, 2H), 1.25-1.18 (m, 4H), 1.14 (t, J=7.5 Hz, 3H), 0.85 (t, J=6.8 Hz, 1H), 0.42-0.28 (m, 4H).
MS: m/z 433.1 (M+1)

Hydrochloride salt of (R)-2'-(3-(4-(3,4-dimethylphenyl)piperazin-1-yl)cyclopent-1-en-1-yl)-7',8'-dihydro-3'H-spiro[cyclopropane-1,6'-quinazolin]-4'(5'H)-one (Compound 136 hydrochloride salt)

$^1$H NMR (400 MHz, DMSO-d$_6$) δ 11.47 (s, 1H, D$_2$O exchangeable), 7.02 (d, J=8.3 Hz 1H), 6.99 (q, J=2.0, 1H), 6.83 (d, J=2.6 Hz, 1H), 6.74 (dd, J=8.3 & 2.6 Hz, 1H), 4.66-4.70 (m, 1H), 3.76-3.74 (m, 2H), 3.55-3.45 (m, 2H), 3.20-3.10 (m, 4H), 2.90-2.72 (m, 2H), 2.70-2.60 (m, 2H), 2.37-2.28 (m, 2H), 2.28-2.24 (m, 2H), 2.18 (s, 3H), 2.13 (s, 3H), 1.54 (t, J=6.3 Hz, 2H), 0.39-0.37 (m, 4H).
MS: m/z 431.18 (M+1)

Hydrochloride salt of (R)-2'-(3-(4-(5-fluoro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 137 hydrochloride salt)

$^1$H NMR (400 MHz, DMSO-d$_6$) δ 11.63 (s, 1H, D$_2$O exchangeable), 8.06 (d, J=1.3 Hz, 1H), 7.0 (d, J=5.1 Hz, 1H), 6.95 (d, J=2.7 Hz, 1H), 4.75-4.64 (m, 1H), 4.36-4.32 (m, 2H), 3.56-3.50 (m, 2H), 3.37-3.26 (m, 2H), 3.20-3.00 (m, 2H), 2.98-2.75 (m, 2H), 2.68-2.59 (m, 2H), 2.35-2.28 (m, 2H), 2.27-2.22 (m, 5H), 1.53 (t, J=6.3 Hz, 2H), 0.40-0.37 (m, 4H).
MS: m/z 436.1 (M+1)

Hydrochloride salt of (R)-2'-(3-(4-(5-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 138 hydrochloride salt)

$^1$H NMR (400 MHz, DMSO-d$_6$): δ 11.60 (brs, 1H, D$_2$O exchangeable), 7.27-7.22 (m, 1H), 7.17-7.06 (m, 2H), 6.97-6.98 (m, 1H), 4.69 (m, 1H), 3.59-3.49 (m, 3H), 3.36-3.17 (m, 3H), 2.90-2.76 (m, 2H), 2.83 (m, 2H), 2.64 (m, 2H), 2.53 (m, 2H), 2.36 (m, 2H), 1.54 (t, J=8 Hz, 4 Hz, 2H), 0.40-0.39 (m, 4H).

MS: m/z 455 (M+1)

(R)-2'-(3-(4-(2-chloro-6-fluorophenyl)piperazin-1-yl)cyclopent-1-en-1-yl)-7',8'-dihydro-3'H-spiro[cyclopropane-1,6'-quinazolin]-4'(5'H)-one (Compound 139)

$^1$H NMR (400 MHz, DMSO-d$_6$): δ 11.35 (brs, 1H, D$_2$O exchangeable), 7.35 (dd, J=7.4, 1.9 Hz, 1H), 7.31-7.16 (m, 2H), 7.02-6.96 (m, 1H), 4.72-4.67 (m, 1H), 3.69-3.57 (m, 2H), 3.57-3.47 (m, 2H), 3.43-3.26 (m, 2H), 3.21-3.02 (m, 2H), 2.95-2.72 (m, 2H), 2.67-2.59 (m, 2H), 2.43-2.24 (m, 4H), 1.54 (t, J=6.2 Hz, 2H), 0.44-0.34 (m, 4H).

MS: m/z 455 (M+1)

Hydrochloride salt of (R)-2'-(3-(4-(2,3-dimethylphenyl)piperazin-1-yl)cyclopent-1-en-1-yl)-7',8'-dihydro-3'H-spiro[cyclopropane-1,6'-quinazolin]-4'(5'H)-one (Compound 140 hydrochloride salt)

$^1$H NMR (400 MHz, DMSO-d$_6$) δ 11.18 (brs, 1H, D$_2$O exchangeable), 7.09 (t, J=7.7 Hz, 1H), 6.99-6.85 (m, 3H), 3.60-3.49 (m, 2H), 3.19-3.11 (m, 2H), 2.92-2.74 (m, 2H), 2.67-2.60 (m, 2H), 2.38-2.30 (m, 2H), 2.27 (s, 2H), 2.22 (s, 3H), 2.19 (s, 3H), 1.54 (t, J=6.2 Hz, 2H), 1.27-1.20 (m, 4H), 0.90-0.82 (m, 2H), 0.44-0.35 (m, 3H).

MS: m/z 431.1 (M+1)

Hydrochloride salt of (R)-2'-(3-(4-(5-chloro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 141 hydrochloride salt)

$^1$H NMR (400 MHz, DMSO-d) δ 11.29 (s, 1H, D$_2$O exchangeable), 8.12 (s, 1H), 7.03 (s, 1H), 6.90 (d, J=2.2 Hz, 1H), 4.70-4.60 (m, 1H), 4.45-4.38 (m, 2H), 3.58-3.48 (m, 2H), 3.35-3.25 (m, 2H), 3.10-3.00 (m, 2H), 2.90-2.70 (m, 2H), 2.65-2.55 (m, 2H), 2.35-2.27 (m, 5H), 2.26-2.22 (m, 2H), 1.53 (t, J=6.3 Hz, 2H), 0.39-0.37 (m, 4H).

MS: m/z 452.06 (M+1)

Hydrochloride salt of (R)-2'-(3-(4-(5-fluoropyridin-3-yl)piperazin-1-yl)cyclopent-1-en-1-yl)-7',8'-dihydro-3'H-spiro[cyclopropane-1,6'-quinazolin]-4'(5'H)-one (Compound 142 hydrochloride salt)

$^1$H NMR (400 MHz, DMSO-d$_6$) δ 12.02 (s, 1H, D$_2$O exchangeable), 8.47-8.38 (m, 1H), 8.29 (d, J=2.1 Hz, 1H), 7.91-7.77 (m, 1H), 7.0 (s, 1 H), 4.75-4.64 (m, 1H), 4.20-4.10 (m, 2H), 3.60-3.40 (m, 4H), 3.20-3.12 (m, 2H), 2.90-2.75 (m, 2H), 2.68-2.60 (m, 2H), 2.35-2.28 (m, 2H), 2.27-2.22 (m, 2H), 1.54 (t, J=6.3 Hz, 2H), 0.40-0.37 (m, 4H).

MS: m/z 422.10 (M+1)

Hydrochloride salt of (R)-2'-(3-(4-(2,5-dimethylphenyl)piperazin-1-yl)cyclopent-1-en-1-yl)-7',8'-dihydro-3'H-spiro[cyclopropane-1,6'-quinazolin]-4'(5'H)-one (Compound 144 hydrochloride salt)

$^1$H NMR (400 MHz, DMSO-d$_6$): δ 11.35 (brs, 1H, D$_2$O exchangeable), 7.35 (dd, J=7.4, 1.9 Hz, 1H), 7.31-7.16 (m, 2H), 7.02-6.96 (m, 1H), 4.72-4.67 (m, 1H), 3.69-3.57 (m, 2H), 3.57-3.47 (m, 2H), 3.43-3.26 (m, 2H), 3.21-3.02 (m, 2H), 2.95-2.72 (m, 2H), 2.67-2.59 (m, 2H), 2.43-2.24 (m, 4H), 1.54 (t, J=6.2 Hz, 2H), 0.44-0.34 (m, 4H).

MS: m/z 431.1 (M+1)

Hydrochloride salt of (R)-2'-(3-(4-(6-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 145 hydrochloride salt)

$^1$H NMR (400 MHz, DMSO-d6) δ 12.16 (s, 1H, D$_2$O exchangeable), 7.94 (t, J=7.9 Hz, 1H), 7.22 (d, J=8.9 Hz, 1H), 6.98 (s, 1H), 6.89 (d, J=7.2 Hz, 1H), 4.74-4.53 (m, 3H), 3.78-3.51 (m, 4H), 3.29-3.12 (m, 2H), 2.83 (dd, J=17.0, 8.2 Hz, 2H), 2.65 (t, J=6.1 Hz, 2H), 2.59 (s, 3H), 2.35 (m, 2H), 2.26 (s, 2H), 1.53 (t, J=6.3 Hz, 2H), 0.49-0.29 (m, 4H).

MS: m/z 417 (M+1)

Hydrochloride salt of (R)-2'-(3-(4-(5-chloro-3-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 146 hydrochloride salt)

$^1$H NMR (400 MHz, DMSO-d$_6$): δ 11.19 (brs, 1H, D$_2$O exchangeable), 8.36 (d, J=10 Hz, 1H), 8.11 (dd, J=8 Hz, 2.5 Hz, 1H), 6.94 (m, 1H), 4.69 (m, 1H), 3.87-3.67 (m, 2H), 3.56-3.45 (m, 2H), 3.28 (m, 2H), 3.17-3.03 (s, 2H), 2.96-2.69 (m, 2H), 2.62 (m, 2H), 2.41-2.21 (m, 4H), 1.53 (t, J=6.3 Hz, 2H), 0.44-0.34 (m, 4H).

MS: m/z 456 (M+1)

Hydrochloride salt of (R)-2'-(3-(4-(2-methylpyridin-4-yl)piperazin-1-yl)cyclopent-1-en-1-yl)-7',8'-dihydro-3'H-spiro[cyclopropane-1,6'-quinazolin]-4'(5'H)-one (Compound 147 hydrochloride salt)

$^1$H NMR (400 MHz, DMSO-d$_6$): δ 12.22 (brs, 1H, D$_2$O exchangeable), 8.26 (d, J=8 Hz, 1H), 7.22-7.16 (dd, J=16 Hz, 4 Hz, 1H), 6.88 (m, 1H), 4.69 (m, 1H), 4.05-3.99 (m, 1H), 3.6 (m, 4H), 3.56-3.45 (m, 2H), 3.15 (s, 3H), 2.88-2.74 (m, 3H), 2.64-2.61 (m, 3H), 2.50-2.33 (m, 4H), 1.53 (t, J=6.3 Hz, 2H), 0.44-0.34 (d, 4H).

MS: m/z 417 (M+1)

Hydrochloride salt of (R)-2'-(3-(4-(4-(thiophen-3-yl)phenyl)piperazin-1-yl)cyclopent-1-en-1-yl)-7',8'-dihydro-3'H-spiro[cyclopropane-1,6'-quinazolin]-4'(5'H)-one (Compound 148 hydrochloride salt)

$^1$H NMR (400 MHz, DMSO-d$_6$) δ 11.26 (bs, 1H, D$_2$O exchangeable), 7.73 (dd, J=3.0, 1.4 Hz, 1H), 7.66-7.58 (m, 3H), 7.51 (dd, J=5.0, 1.3 Hz, 1H), 7.09-7.02 (m, 2H), 6.99-6.93 (m, 1H), 4.74-4.65 (m, 1H), 3.92 (d, J=9.4 Hz, 2H), 3.61-3.49 (m, 2H), 3.25-3.11 (m, 4H), 2.93-2.73 (m, 2H), 2.67-2.60 (m, 2H), 2.40-2.29 (m, 2H), 2.26 (s, 2H), 1.54 (t, J=6.2 Hz, 2H), 0.40 (d, J=4.0 Hz, 4H).

MS: m/z 485 (M+1).

Hydrochloride salt of (R)-2'-(3-(4-(6-phenylpyridin-3-yl)piperazin-1-yl)cyclopent-1-en-1-yl)-7',8'-dihydro-3'H-spiro[cyclopropane-1,6'-quinazolin]-4'(5'H)-one (Compound 157 hydrochloride salt)

$^1$H NMR (400 MHz, DMSO-d6): δ 11.75 (s, 1H, D$_2$O exchangeable), 8.43 (d, J=2.9 Hz, 1H), 8.16 (d, J=9.0 Hz, 1H), 8.03 (dt, J=6.0 &1.5 Hz), 7.63-7.50 (m, 3H), 6.96 (dd, J=2.8 & 1.5 Hz, 1H), 4.70-4.60 (m, 1H), 4.23-4.16 (m, 2H), 3.65-3.50 (m, 2H), 3.48-3.35 (m, 2H), 3.25-3.10 (m, 2H), 2.90-2.70 (m, 2H), 2.65-2.55 (m, 2H), 2.40-2.30 (m, 2H), 2.26-2.20 (m, 2H), 1.54 (t, J=6.3 Hz, 2H), 0.39-0.37 (m, 4H).

MS: m/z 480.1 (M+1).

Hydrochloride salt of (R)-2'-(3-(4-([1,1'-biphenyl]-4-yl)piperazin-1-yl)cyclopent-1-en-1-yl)-7',8'-dihydro-3'H-spiro[cyclopropane-1,6'-quinazolin]-4'(5'H)-one (Compound 158 hydrochloride salt)

$^1$H NMR (400 MHz, DMSO-d$_6$): δ 11.66 (s, 1H, D$_2$O exchangeable), 7.70-7.55 (m, 4H), 7.42 (t, J=7.6 Hz, 2H), 7.29 (t, J=7.3 Hz, 1H), 7.11 (d, J=8.4 Hz, 2H), 7.02 (d, J=2.6 Hz, 1H), 4.75-4.65 (m, 1H), 4.00-3.90 (m, 2H), 3.65-3.50 (m, 2H), 3.35-3.10 (m, 4H), 2.90-2.75 (m, 2H), 2.70-2.55 (m, 2H), 2.40-2.28 (m, 2H), 2.26-2.22 (m, 2H), 1.54 (t, J=6.3 Hz, 2H), 0.39-0.37 (m, 4H).

MS: m/z 479.1 (M+1).

Hydrochloride salt of 2'-(3-(3-(4-chlorophenyl)-3,8-diazabicyclo[3.2.1]octan-8-yl)cyclopent-1-en-1-yl)-7',8'-dihydro-3'H-spiro[cyclopropane-1,6'-quinazolin]-4'(5'H)-one (Compound 159 hydrochloride salt)

$^1$H NMR (400 MHz, DMSO-d$_6$): δ 10.79 (bs, 1H, D$_2$O exchangeable), 7.28 (d, J=8.2 Hz, 2H), 7.09 (s, 1H), 6.95 (d, J=8.7 Hz, 2H), 4.50-4.42 (m, 1H), 4.30-4.19 (m, 2H), 3.79-3.72 (m, 2H), 3.49-3.32 (m, 4H), 3.02 (t, J=12.2 Hz, 1H), 2.81-2.71 (m, 1H), 2.63 (d, J=6.4 Hz, 2H), 2.27 (s, 4H), 2.06-1.97 (m, 2H), 1.54 (t, J=6.4 Hz, 2H), 0.43-0.35 (m, 4H).

MS: m/z 463.11 (M+).

EXAMPLE 14

Synthesis of 2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one hydrochloride salt (Compound 118 hydrochloride salt)

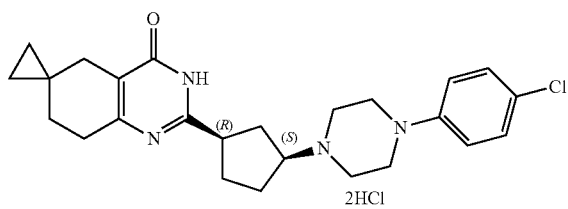

and

2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one hydrochloride salt (Compound 119 hydrochloride salt)

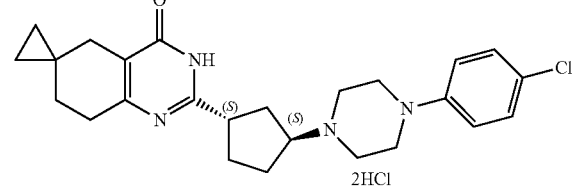

Step 1: (1R,3S)-methyl 3-aminocyclopentanecarboxylate hydrochloride

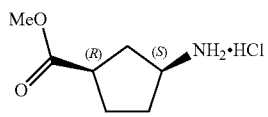

To a solution of (1R,3S)-3-aminocyclopentanecarboxylic acid hydrochloride (2.5 g, 15.09 mmol) in dry methanol (10 ml) under N$_2$ at 0° C. was added thionyl chloride (5.51 ml, 75 mmol) dropwise. The reaction mixture was slowly warmed to room temperature and stirred overnight. The reaction was concentrated in vacuo. The resultant residue was washed with anhydrous diethyl ether (3×30 ml) and dried under high vacuum to afford of (1S,3R)-3-aminocyclopentanecarboxylic acid methyl ester (2.65 g 98%) as the hydrochloride salt that was used in a subsequent reaction without purification.

GCMS m/z: 179.29.

$^1$H NMR (400 MHz, DMSO-d$_6$): δ 8.27 (s, 2H), 3.61 (s, 3H), 3.46-3.41 (m, 1H), 2.87-2.81 (m, 1H), 2.28-2.21 (m, 1H), 1.96-1.86 (m, 3H), 1.78-1.62 (m, 2H).

Step 2: (1R,3S)-methyl 3-(4-(4-chlorophenyl)piperazin-1-yl)cyclopentanecarboxylate

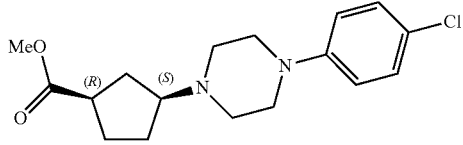

(1R,3S)-methyl 3-aminocyclopentanecarboxylate hydrochloride (1.5 g, 8.35 mmol), 4-chloro-N,N-bis(2-chloroethyl)aniline (2.32 g, 9.18 mmol), sodium hydrogencarbonate (4.91 g, 58.4 mmol), and potassium iodide (0.14 g, 0.83 mmol) were suspended in n-butanol (50 mL). The reaction mixture was stirred at 110° C. for overnight. Upon completion, the reaction mixture was evaporated under vacuo. The resulting crude residue was purified by column chromatography using ethyl acetate in hexane as eluent to obtain (1R,3S)-methyl 3-(4-(4-chlorophenyl)piperazin-1-yl)cyclopentanecarboxylate (1.5 g, 55.6%).

MS m/z: 323.1 (M+1).

$^1$H NMR (400 MHz, DMSO-d$_6$): δ 7.24-7.16 (m, 2H), 6.94-6.75 (m, 2H), 3.60 (s, 3H), 3.11-3.09 (m, 4H), 2.86-2.77 (m, 1H), 2.58-2.49 (m, 4H), 2.16-2.09 (m, 1H), 1.87-1.76 (m, 3H), 1.60-1.49 (m, 3H).

Step 3: (1R,3S)-3-(4-(4-chlorophenyl)piperazin-1-yl) cyclopentane carboxylic acid

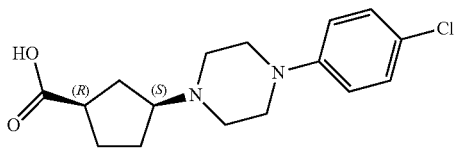

To a stirred solution of (1R,3S)-methyl 3-(4-(4-chlorophenyl)piperazin-1-yl)cyclopentanecarboxylate (1.5 g, 4.65 mmol) in tetrahudrofuran:water (4:1) was added a solution of lithium hydroxide monohydrate (0.58 g, 13.94 mmol) in 5 ml water. Reaction mixture was allowed to stir at room temperature for 20 h. Upon completion, the reaction mixture was concentrated under reduced pressure to remove tetrahudrofuran. The resulting residue was diluted with 10 ml of water followed by washing with diethyl ether (3×20 ml). The aqueous layer was acidified at 0° C. with 1N hydrochloric acid to pH 6-7 and the mixture was extracted with ethyl acetate (2×50 ml). The organic layer was separated and dried over sodium sulphate and concentrated under reduced pressure to obtain (1R,3S)-3-(4-(4-chlorophenyl)piperazin-1-yl)cyclopentanecarboxylic acid (1.0 g, 69.7%).

MS m/z: 309.1 (M+1).

$^1$H NMR (400 MHz, DMSO-$d_6$): δ 7.27-7.13 (m, 2H), 6.96-6.91 (m, 2H), 3.11-3.09 (m, 4H), 2.86-2.77 (m, 1H), 2.58-2.49 (m, 4H), 2.14-2.09 (m, 1H), 1.84-1.76 (m, 3H), 1.59-1.46 (m, 3H).

Step 4: ethyl 6-((1R,3S)-3-(4-(4-chlorophenyl)piperazin-1-yl)cyclopentane carboxamido)spiro[2.5]oct-5-ene-5-carboxylate

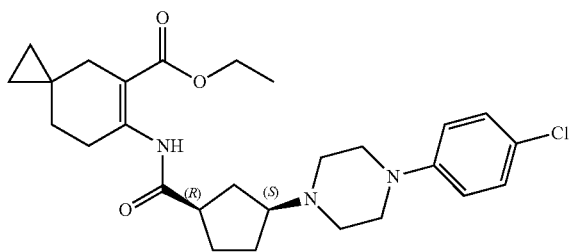

To an ice cold solution of ethyl 2-aminocyclohex-1-enecarboxylate (1.27 g, 6.48 mmol) in pyridine (5 ml), phosphorus trichloride (0.18 ml, 2.10 mmol) was added. After 15 min, (1R,3S)-3-(4-(4-chlorophenyl)piperazin-1-yl)cyclopentanecarboxylic acid (0.5 g, 1.62 mmol) was added at room temperature to the mixture, followed by stirring at temperature for 6 h. Upon completion, the reaction mixture was diluted with chloroform and the organic layer was washed with saturated aqueous sodium hydrogencarbonate solution, The organic layer was separated, dried over sodium sulphate and concentrated under reduced pressure. The residue obtained was purified by silica gel column chromatography using ethyl acetate in hexane as eluent to afford ethyl 6-((1R,3S)-3-(4-(4-chlorophenyl)piperazin-1-yl)cyclopentanecarboxamido) spiro[2.5]oct-5-ene-5-carboxylate (300 mg, 38.1%).

MS m/z: 486

$^1$H NMR (400 MHz, DMSO-$d_6$): δ 11.32 (s, 1H), 7.22 (d, J=8 Hz, 2H), 6.93 (d, J=8 Hz, 2H), 4.12 (q, 2H), 3.11-3.09 (m, 4H), 2.91-2.78 (m, 1H), 2.58-2.49 (m, 4H), 2.14-2.09 (m, 3H), 1.99 (s, 3H), 1.84-1.76 (m, 3H), 1.59-1.46 (m, 3H), 1.20 (s, 3H), 0.44-0.33 (m, 4H).

Step 5: 6-((1R,3S)-3-(4-(4-chlorophenyl)piperazin-1-yl)cyclopentane carboxamido)spiro[2.5]oct-5-ene-5-carboxylic acid

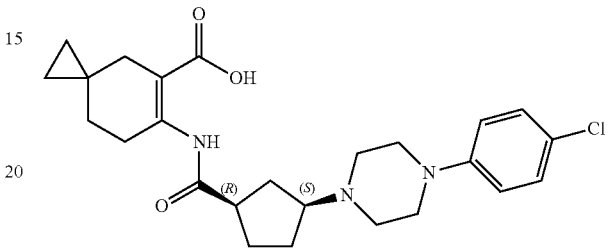

Ethyl 6-((1R,3S)-3-(4-(4-chlorophenyl)piperazin-1-yl)cyclopentane carboxamido)spiro[2.5]oct-5-ene-5-carboxylate (0.3 g, 0.62 mmol) was dissolved in 10 ml of tetrahudrofuran/methanol/water (3:1:1). To this solution was added lithium hydroxide (0.12 g, 2.8 mmol). The mixture was stirred at room temperature overnight, concentrated, and acidified using 1 N hydrochloric acid to pH 6. To the resulting white slurry was added water (20 ml). The mixture was extracted with dichloromethane (2×50 ml). The organic layer was dried over sodium sulfate and concentrated to afford the title compound 6-((1R,3S)-3-(4-(4-chlorophenyl)piperazin-1-yl)cyclopentane carboxamido)spiro[2.5]oct-5-ene-5-carboxylic acid along with its corresponding diastereomer 6-((1S,3S)-3-(4-(4-chlorophenyl) piperazin-1-yl)cyclopentanecarboxamido)spiro[2.5]oct-5-ene-5-carboxylic acid as observed on the HPLC column.

Yield: (0.25 g, 88%)

MS m/z: 458.4 (M+1)

$^1$H NMR (400 MHz, DMSO-$d_6$): δ 11.72 (s, 1H), 7.25-7.22 (m, 2H), 6.98-6.94 (m, 2H), 3.11-3.09 (m, 4H), 2.93-2.90 (m, 3H), 2.80-2.73 (m, 4H), 2.14-2.09 (m, 3H), 1.88-1.80 (m, 3H), 1.40-1.37 (m, 3H), 1.26-1.24 (m, 2H), 0.33-0.30 (m, 4H).

Step 6: 2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one

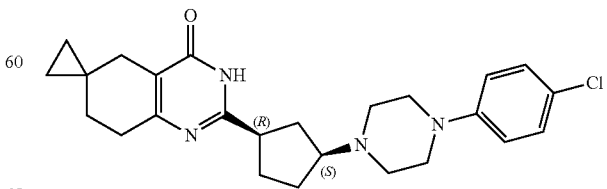

2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one

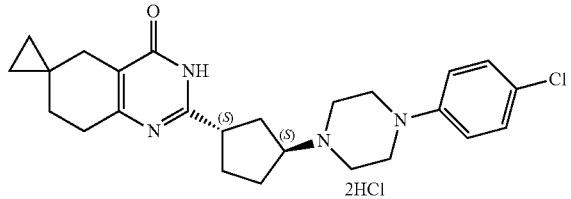

To an ice cooled solution of the diastereomeric mixture obtained from step 5 (0.25 g, 0.55 mmol) in tetrahudrofuran (10 ml), acetic anhydride (0.16 ml, 1.64 mmol) was added. The mixture was refluxed for an hour. Thereafter, the reaction mixture was cooled under ice bath and ammonia (1.56 ml, 10.92 mmol) (7N solution in methanol) was added to the mixture. The reaction mixture was refluxed for 10-20 min. Upon completion, the reaction mixture was concentrated under reduced pressure. The residue obtained was purified over neutral alumina (chloroform: methanol=99:1) to afford title compound 2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one (90 mg, 37.5%) and the corresponding minor diastereomer 2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one (40 mg, 16.6%) as observed on the HPLC Column.

MS m/z: 439.1 (M+1).

2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one $^1$H NMR (400 MHz, DMSO-$d_6$)(Major diastereomer): δ 12.41 (s, 1H), 7.22 (d, J=8 Hz, 2H), 6.94 (d, J=8 Hz, 2H), 3.32-3.28 (m, 2H), 3.16 (s, 3H), 3.03-2.99 (m, 2H), 2.60-2.56 (m, 3H), 2.17-2.11 (m, 2H), 1.99-181 (m, 3H), 1.50 (t, J=6.3 Hz, 3H), 1.34 (s, 1H), 1.26-1.23 (m, 3H), 0.37-0.35 (m, 4H).

MS m/z: 439.1 (M+1).

2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one $^1$H NMR (400 MHz, DMSO-$d_6$) (Minor diastereomer): δ 11.36 (s, 1H), 7.25-7.22 (m, 2H), 6.88-6.84 (m, 2H), 3.25 (bs, 5H), 3.03-2.70 (m, 5H), 2.38 (bs, 2H), 2.26-2.13 (m, 4H), 2.04-1.88 (m, 2H), 1.61-1.58 (m, 4H), 0.47-0.41 (m, 4H).

Step 7: Hydrochloride salt of 2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one (Compound 118 hydrochloride salt)

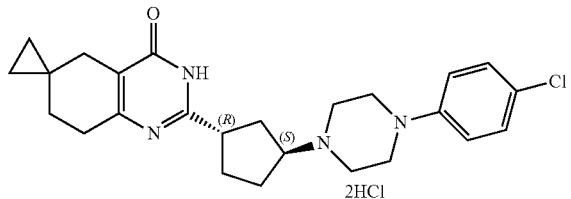

Hydrochloride salt of 2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one (Compound 119 hydrochloride)

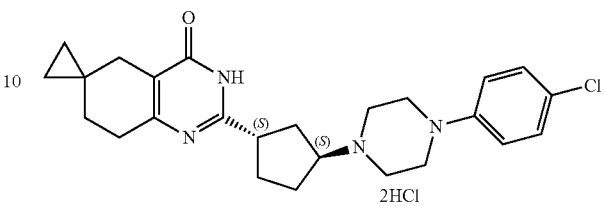

To a stirred solution of 2'-((1R,3S)-3-(4-(4-chlorophenyl)piperazin-1-yl)cyclopentyl)-7',8'-dihydro-3'H-spiro[cyclopropane-1,6'-quinazolin]-4'(5'H)-one or 2'-((1S,3S)-3-(4-(4-chlorophenyl)piperazin-1-yl)cyclopentyl)-7',8'-dihydro-3'H-spiro[cyclopropane-1,6'-quinazolin]-4'(5'H)-one (50 mg, 0.11 mmol) in dichloromethane (5 ml), hydrochloric acid (solution 2.0 M in diethyl ether) (2.28 ml, 4.56 mmol) was added at 0° C. The reaction mixture was stirred at room temperature for 1 h. The reaction mixture was concentrated under reduced pressure and the resulting solid was washed with diethyl ether (2×5 ml) to obtain (50 mg, 86%) of title compound.

Compound 118 hydrochloride salt:
$^1$H NMR (400 MHz, DMSO-$d_6$): δ 10.95 (bs, 1H), 7.36-7.28 (m, 2H), 7.05-7.02 (m, 2H), 3.83-3.58 (m, 5H), 3.15 (s, 4H), 2.64 (t, 2H), 2.45-2.38 (m, 1H), 2.28-2.19 (m, 2H), 2.09-2.00 (m, 3H), 1.53 (t, 2H), 1.26-1.22 (m, 3H), 0.40-0.36 (m, 4H).

Compound 119 hydrochloride salt:
$^1$H NMR (400 MHz, DMSO-$d_6$): δ 11.18 (bs, 1H), 7.32-7.28 (m, 2H), 7.06-7.02 (m, 2H), 3.84-3.57 (m, 3H), 3.57-3.55 (m, 2H), 3.39-3.31 (m, 1H), 3.19-3.10 (m, 4H), 2.63 (t, 2H), 2.43-2.35 (m, 1H), 2.28-2.16 (m, 2H), 1.99-1.92 (m, 1H), 1.89-1.81 (m, 1H), 1.52 (t, 2H), 1.26-1.22 (m, 2H), 0.42-0.36 (m, 4H).

EXAMPLE 15

The following compounds were prepared according to the procedures described above in example 14 with appropriate changes in the reactants and reaction conditions.

Hydrochloride salt of 2'-((1S,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 120 hydrochloride salt)

MS (EI) m/z: 439.18 (M+1).
$^1$H NMR (400 MHz, DMSO-$d_6$): δ 11.21 (bs, 1H), 7.30 (d, J=8 Hz, 2H), 7.30 (d, J=8 Hz, 2H), 3.83-3.54 (m, 5H), 3.24-3.17 (m, 5H), 2.69-2.66 (m, 2H), 2.47-2.41 (m, 1H), 2.33-2.23 (m, 3H), 2.08-2.02 (m, 4H), 1.54 (t, J=6.3 Hz, 2H), 0.41-0.39 (m, 4H).

Hydrochloride salt of 2'-((1R,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 121 hydrochloride salt)

MS (EI) m/z: 439.1 (M+1).
$^1$H NMR (400 MHz, DMSO-$d_6$): δ 11.47 (bs, 1H), 7.32-7.28 (m, 2H), 7.06-7.01 (m, 2H), 3.86-3.78 (m, 3H), 3.56-3.54 (m, 2H), 3.45-3.39 (m, 1H), 3.20-3.13 (m, 4H), 2.69-2.65 (m, 2H), 2.48-2.40 (m, 2H), 2.27-2.18 (m, 4H), 2.05-1.85 (m, 2H), 1.53 (t, J=6.3 Hz, 2H), 0.43-0.37 (m, 4H).

EXAMPLE 16

Synthesis of 2'-((1S,3S)-3-(4-(4-fluorophenyl)piperazin-1-yl)cyclopentyl)-7',8'-dihydro-3'H-spiro[cyclopropane-1,6'-quinazolin]-4'(5'H)-one hydrochloride salt (Compound 149 hydrochloride salt)

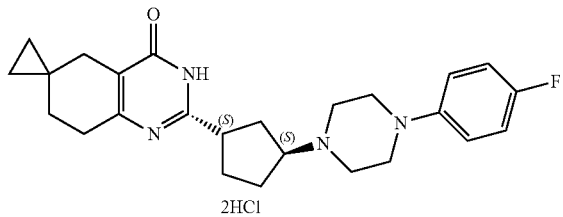

Step 1: (S)-benzyl 8,8-dimethyl-6,10-dioxaspiro[4.5]decane-2-carboxylate

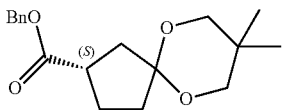

Benzyl alcohol (7.28 ml, 70.0 mmol), DCC (0.43 g, 2.1 mmol) and a catalytic amount of 4-dimethylammino pyridine (0.20 g, 1.68 mmol) were successively added to a solution of (S)-8,8-dimethyl-6,10-dioxaspiro[4.5]decane-2-carboxylic acid (Synthesized following procedure as described in DE4312832 and US20080161564, 3 g, 14.00 mmol) in anhydrous Dichloromethane (50 ml). The reaction mixture was stirred for 24 h at 25-30° C. and then acetone (10 ml) was added. The resulting suspension was filtered and subsequently concentrated under vacuum. The residue was purified by silica gel column chromatography using ethyl acetate in hexane as eluents to obtain (S)-benzyl 8,8-dimethyl-6,10-dioxaspiro[4.5]decane-2-carboxylate (3.5 g, 82%).

MS m/z: 305.0

$^1$H NMR (400 MHz, CDCl$_3$) δ 7.43-7.29 (m, 5H), 5.21-5.12 (m, 2H), 3.57-3.40 (m, 4H), 3.02-2.89 (m, 1H), 2.37-2.26 (m, 1H), 2.23-2.12 (m, 1H), 2.09-1.88 (m, 4H), 1.01 (s, 3H), 0.94 (s, 3H).

Step 2: (S)-benzyl 3-oxocyclopentanecarboxylate

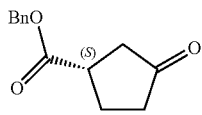

To a solution of (S)-benzyl 8,8-dimethyl-6,10-dioxaspiro[4.5]decane-2-carboxylate (3.5 g, 11.50 mmol) in ethanol (50 ml) at 0° C. was added 0.1 N hydrochloric acid (17.5 ml) drop wise. The reaction was stirred at 25° C. for overnight. Upon completion, the reaction mixture was concentrated under reduced pressure; the residue was dissolved in dichloromethane (50 ml) and diluted with water (25 ml). The organic mass was extracted using dichloromethane (2×50 ml) and the combined organic layer was dried over sodium sulfate and concentrated under reduced pressure. The crude product was purified by column chromatography over silica gel using ethyl acetate in hexane as eluents to obtain (S)-benzyl 3-oxocyclopentanecarboxylate (2 g, 80%).

GCMS m/z: 218.13.

$^1$H NMR (400 MHz, CDCl$_3$): δ 7.47-7.26 (m, 5H), 5.18 (s, 2H), 3.26-3.11 (m, 1H), 2.62-2.09 (m, 6H).

Step 3: (1S,3R)-benzyl 3-hydroxycyclopentanecarboxylate

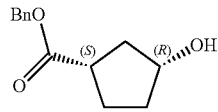

To a solution of (S)-benzyl 3-oxocyclopentanecarboxylate (2 g, 9.16 mmol) in methanol (40 ml) was added sodium borohydride (0.35 g, 9.16 mmol) in portion wise manner at 0° C. and the reaction was allowed to stir at 0° C. for 20 min. Upon completion, acetic acid (0.57 ml, 10.08 mmol) was added to the reaction mixture and stirring was continued for 5 min. Methanol was removed under reduced pressure and to the residue was added water (50 ml). The organic mass was extracted using ethyl acetate (2×50 ml). Combined organic layer was dried over sodium sulfate and concentrated under reduced pressure to obtain a crude compound, which was purified by column chromatography over silica gel using ethyl acetate in hexane as eluents to obtain (1S)-benzyl 3-hydroxycyclopentanecarboxylate as a diastereomeric mixture (75:25) of title compound (1.6 g, 79%).

GCMS m/z: 220.08

Step 4: (1S,3R)-benzyl 3-(((4-(trifluoromethyl)phenyl)sulfonyl)oxy)cyclopentanecarboxylate

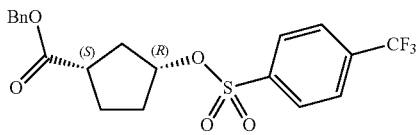

To a solution of diastereomeric mixture, step 3 (1.5 g, 6.81 mmol) in dichloromethane (20 ml) at 0° C., was added triethylamine (1.42 ml, 10.21 mmol) and 4-dimethylammino pyridine (1.25 g, 10.21 mmol), followed by 4-(trifluoromethyl)benzene-1-sulfonyl chloride (2.50 g, 10.21 mmol). After stirring at 0° C. for 15 min and then at room temperature for 3-4 h, the reaction mixture was partitioned between dichloromethane and saturated solution of sodium bicarbonate. The organic layer was washed with brine, dried over Na$_2$SO$_4$, and concentrated. The residue was purified by column chromatography over silica gel using ethyl acetate in hexane as eluents to obtain (1S)-benzyl 3-(((4-(trifluoromethyl)phenyl)sulfonyl)oxy)cyclopentanecarboxylate as a diastereomeric mixture of title compound (1.7 g, 58.3%).

MS m/z: 429 (M+1).

Step 5: (1S,3S)-benzyl 3-(4-(4-fluorophenyl)piperazin-1-yl)cyclopentanecarboxylate

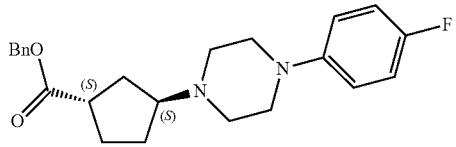

To the diastereomeric mixture, step 4 (1.7 g, 3.97 mmol) dissolved in acetonitrile (15 ml), powdered potassium carbonate (1.09 g, 7.94 mmol) and 1-(4-fluorophenyl)piperazine (0.72 ml, 3.97 mmol) was added. The reaction mixture was stirred at reflux until the completion (typically 18 h). The reaction mixture was cooled to R.T. filtered through a pad of celite, washed with acetonitrile (20 ml), and concentrated. The residue was purified by column chromatography over silica gel using ethyl acetate in hexane as eluents to obtain (1S)-benzyl 3-(4-(4-fluorophenyl)piperazin-1-yl)cyclopentanecarboxylate as a diastereomeric mixture (75:22) of title compound (1.2 g, 79%).

The above diastereomeric mixture was purified by chiral column to obtain (1S,3S)-benzyl 3-(4-(4-fluorophenyl)piperazin-1-yl)cyclopentanecarboxylate (0.7 g, 46.1%) as the major diastereomer.

MS m/z: 383.4 (M+1)

$^1$H NMR (400 MHz, CDCl$_3$): δ 7.47-7.26 (m, 5H), 7.01-6.95 (m, 2H), 6.92-6.85 (m, 2H), 5.18 (s, 2H), 3.28-3.22 (m, 4H), 3.06-2.82 (m, 5H), 2.30 (bs, 1H), 2.16-2.06 (m, 3H), 1.86-1.80 (m, 3H).

Step 6: (1S,3S)-3-(4-(4-fluorophenyl)piperazin-1-yl)cyclopentanecarboxylic acid

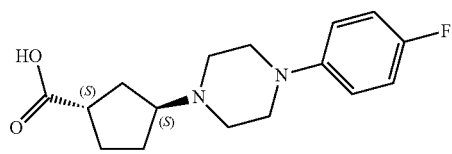

To a solution of (1S,3S)-benzyl 3-(4-(4-fluorophenyl)piperazin-1-yl)cyclopentanecarboxylate (0.6 g, 0.52 mmol) in methanol (15 ml) was added 10% palladium on charcoal (60 mg). The reaction mixture was stirred at room temperature under H$_2$ atmosphere at atmospheric pressure for 2 h. Upon completion, the reaction mixture was filtered through a pad of celite, and washed with methanol (15 ml). The filtrate was concentrated under reduced pressure to afford the title compound (0.4 g, 87%), which was used further without purification.

MS m/z: 293.07 (M+1)

$^1$H NMR (400 MHz, CDCl$_3$): δ 7.01-6.96 (m, 2H), 6.91-6.86 (m, 2H), 3.29-3.23 (m, 4H), 3.06-2.80 (m, 5H), 2.28 (bs, 1H), 2.16-2.06 (m, 3H), 1.86-1.80 (m, 3H).

Step 7: ethyl 6-((1S,3S)-3-(4-(4-fluorophenyl)piperazin-1-yl)cyclopentanecarboxamido)spiro[2.5]oct-5-ene-5-carboxylate

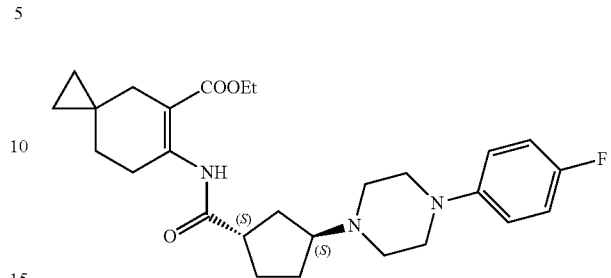

Title compound was prepared in manner as depicted in step 4 of Example 14.

MS (EI) m/z: 470.0 (M+1).

Step 8: 6-((1S,3S)-3-(4-(4-fluorophenyl)piperazin-1-yl)cyclopentanecarboxamido)spiro[2.5]oct-5-ene-5-carboxylic acid

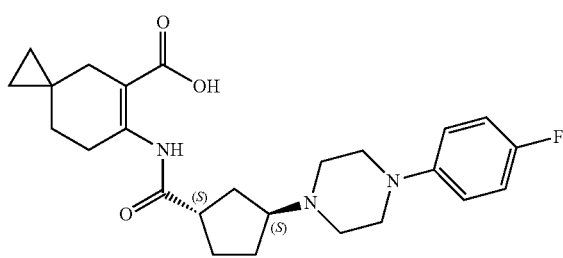

MS (EI) m/z: 442.11 (M+1).

This compound were prepared in manner as depicted in step 5 of Example 14.

Step 9: 2'-((1S,3S)-3-(4-(4-fluorophenyl)piperazin-1-yl)cyclopentyl)-7',8'-dihydro-3'H-spiro[cyclopropane-1,6'-quinazolin]-4'(5'H)-one and 2'-((1R,3S)-3-(4-(4-fluorophenyl)piperazin-1-yl)cyclopentyl)-7',8'-dihydro-3'H-spiro[cyclopropane-1,6'-quinazolin]-4'(5'H)-one

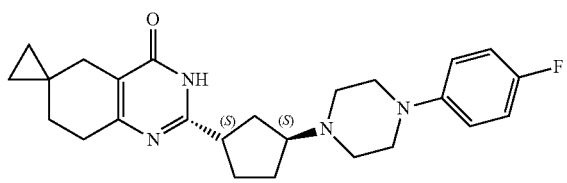

MS (EI) m/z: 423.17 (M+1).

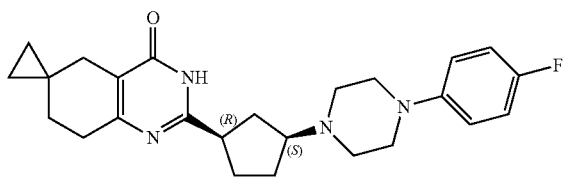

MS (EI) m/z: 423.1 (M+1).

Title compounds were prepared in manner as depicted in step 6 of Example 14.

Step 10: Hydrochloride salt of 2'-((1S,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 149 hydrochloride salt)

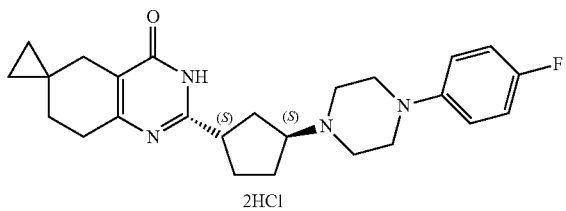

and

Hydrochloride salt of 2'-((1R,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 150 hydrochloride salt)

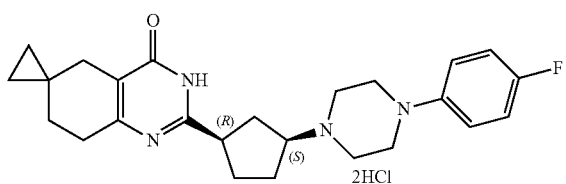

Compound 149 hydrochloride salt:

MS (EI) m/z: 423.17 (M+1). free base $^1$H NMR (400 MHz, DMSO-$d_6$): δ 11.37 (bs, 1H), 7.36-7.02 (m, 4H), 3.84-3.82 (m, 1H), 3.75-3.72 (m, 2H), 3.57-3.55 (m, 2H), 3.43-3.41 (m, 1H), 3.17-3.15 (m, 4H), 2.69-2.60 (m, 2H), 2.60-2.43 (s, 1H), 2.23 (s, 3H), 2.03-1.98 (m, 3H), 1.55-1.51 (m, 2H), 1.21 (s, 1H), 0.42-0.40 (m, 4H).

Compound 150 hydrochloride salt:

MS (EI) m/z: 423.17 (M+1). free base $^1$H NMR (400 MHz, DMSO-$d_6$): δ 7.32-7.02 (m, 4H), 3.60-2.67 (m, 8H), 2.60-2.55 (m, 2H), 2.47-2.37 (m, 2H), 2.25-2.21 (m, 3H), 2.11-1.95 (m, 4H), 1.54-1.51 (m, 2H), 1.26-1.22 (m, 1H), 0.40-0.39 (m, 4H).

Title compounds were prepared in manner as depicted in step 7 of Example 14.

EXAMPLE 17

Synthesis of 2'-((1S,3R)-3-(4-(4-fluorophenyl)piperazin-1-yl)cyclopentyl)-7',8'-dihydro-3'H-spiro[cyclopropane-1,6'-quinazolin]-4'(5'H)-one hydrochloride salt. (Compound 151 hydrochloride salt)

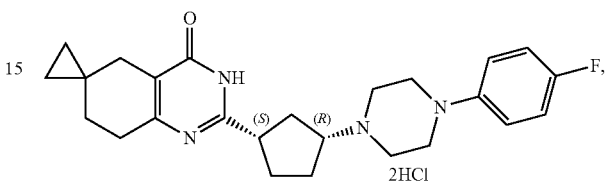

and

2'-((1R,3R)-3-(4-(4-fluorophenyl)piperazin-1-yl)cyclopentyl)-7',8'-dihydro-3'H-spiro[cyclopropane-1,6'-quinazolin]-4'(5'H)-one hydrochloride salt. (Compound 152 hydrochloride salt)

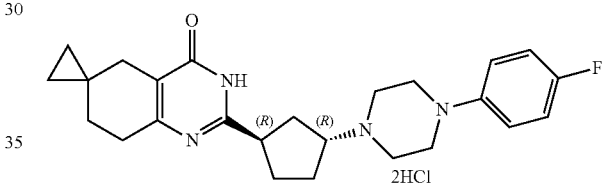

Step 1: (S)-ethyl 6-(8,8-dimethyl-6,10-dioxaspiro[4.5]decane-2-carboxamido)spiro[2.5]oct-5-ene-5-carboxylate

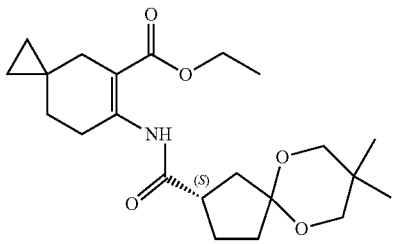

To a stirred solution of (S)-8,8-dimethyl-6,10-dioxaspiro[4.5]decane-2-carboxylic acid (1.5 g, 7.0 mmol) and NMM (1.15 ml, 10.50 mmol) in acetonitrile (35 ml), isobutyl chloroformate (1 ml, 7.70 mmol) was added drop wise at −5 to −10° C. After 1 h, a solution of ethyl 6-aminospiro[2.5]oct-5-ene-5-carboxylate (3.42 g, 17.50 mmol) in acetonitrile (15 ml) was added and the reaction was allowed to stir at 0° C. to −5° C. for 1 h followed by stirring overnight at 25-30° C. Upon completion, the reaction mixture was quenched by addition of water (10 ml). Organic solvent was removed under reduced pressure and the residue was diluted with ethyl acetate (50 ml) and 10% sodium bicarbonate (25 ml). The organic mass was extracted using ethyl acetate (3×50 ml). Combined organic layer was dried over sodium sulfate and concentrated under reduced pressure to afford a crude solid, which was purified by column chromatography over silica gel using ethyl acetate in hexane as eluents to obtain the title compound (1.55 g, 56.6%).

MS m/z: 392 (M+1)

$^1$H NMR (400 MHz, CDCl$_3$): δ 12.29 (s, 1H), 4.17 (q, 2H), 3.57-3.40 (m, 4H), 3.02-2.89 (m, 2H), 2.88 (s, 1H), 2.36-2.33 (m, 1H), 2.19-2.16 (m, 3H), 2.13-1.90 (m, 3H), 2.09-1.88 (m, 3H), 1.43 (t, 2H), 1.29 (t, 3H), 1.01 (s, 3H), 0.94 (s, 3H), 0.37-0.31 (m, 4H).

Step 2: (S)-ethyl 6-(3-oxocyclopentanecarboxamido) spiro[2.5]oct-5-ene-5-carboxylate

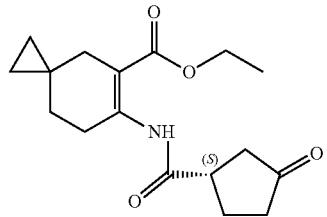

To a solution of (S)-ethyl 6-(8,8-dimethyl-6,10-dioxaspiro [4.5]decane-2-carboxamido)spiro[2.5]oct-5-ene-5-carboxylate. (1.5 g, 11.50 mmol) in ethanol (25 ml) was added 1 N hydrochloric acid (7.5 ml) in portion wise manner at 0° C. and the reaction was allowed to stir at 25° C. for overnight. Organic solvent was removed under reduced pressure; the residue was diluted with dichloromethane (50 ml) and water (25 ml). The organic mass was extracted using dichloromethane (3×50 ml). Combined organic layer was dried over sodium sulfate and concentrated under reduced pressure to obtain a crude compound, which was purified by column chromatography over silica gel using ethyl acetate in hexane as eluents to obtain (S)-ethyl 6-(3-oxocyclopentanecarboxamido)spiro[2.5]oct-5-ene-5-carboxylate. (1 g, 85%).

MS m/z: 306 (M+1)

$^1$H NMR (400 MHz, DMSO-d$_6$): δ 11.35 (s, 1H), 4.13 (q, 2H), 3.19-3.14 (m, 1H), 2.91-2.87 (m, 2H), 2.40-2.30 (m, 2H), 2.26-2.19 (m, 3H), 2.16-2.14 (m, 2H), 2.01-1.91 (s, 1H), 1.39 (t, 2H), 1.21 (t, 3H), 0.37-0.31 (m, 4H).

Step 3: ethyl 6-((1S,3R)-3-(4-(4-fluorophenyl)piperazin-1-yl)cyclopentanecarboxamido)spiro[2.5]oct-5-ene-5-carboxylate

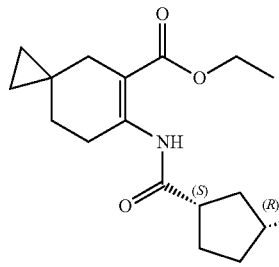

To a solution of (S)-ethyl 6-(3-oxocyclopentanecarboxamido)spiro[2.5]oct-5-ene-5-carboxylate (0.7 g, 2.23 mmol) in 1,2-dichloroethane (10 ml) were added 1-(4-fluorophenyl) piperazine (0.43 g, 2.40 mmol), glacial acetic acid (0.14 g, 2.40 mmol) and sodium triacetoxy borohydride (0.7 g, 3.44 mmol). The mixture was stirred at RT for 24 h before removal of the solvent. The residue was treated with saturated sodium bicarbonate, extracted with ethyl acetate and washed with brine. The organic layer was dried over sodium sulfate, filtered, and concentrated under reduced pressure to afford the crude residue which was purified by column chromatography over silica gel using ethyl acetate in hexane as eluents to obtain a diastereomeric mixture (7:3) of title compound (0.9 g, 84%).

Separation of the diastereomeric mixture was carried out using chiral column to obtain major diastereomer i.e ethyl 6-((1S,3R)-3-(4-(4-fluorophenyl)piperazin-1-yl)cyclopentane carboxamido)spiro[2.5]oct-5-ene-5-carboxylate (0.5 g, 46.4%).

MS m/z: 470.11 (M+1)

$^1$H NMR (400 MHz, DMSO-d$_6$): δ 11.73 (s, 1H), 7.01-6.88 (m, 4H), 4.13 (q, 2H), 3.22-3.07 (m, 5H), 2.78 (bs, 5H), 2.30 (bs, 2H), 2.19-2.13 (m, 4H), 1.98-1.87 (m, 2H), 2.01-1.91 (s, 2H), 1.44 (t, 2H), 1.30 (t, 3H), 0.37-0.35 (m, 4H).

Step 4: 6-((1S,3R)-3-(4-(4-fluorophenyl)piperazin-1-yl)cyclopentane carboxamido)spiro[2.5]oct-5-ene-5-carboxylic acid.

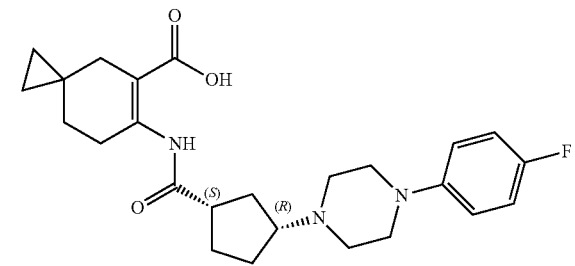

Title compound was prepared in manner as depicted in step 5 of Example 14.

MS m/z: 442.11 (M+1).

Step 5: 2'-((1S,3R)-3-(4-(4-fluorophenyl)piperazin-1-yl)cyclopentyl)-7',8'-dihydro-3'H-spiro[cyclopropane-1,6'-quinazolin]-4'(5'H)-one, & 2'-((1R,3R)-3-(4-(4-fluorophenyl)piperazin-1-yl)cyclopentyl)-7',8'-dihydro-3'H-spiro[cyclopropane-1,6'-quinazolin]-4'(5'H)-one

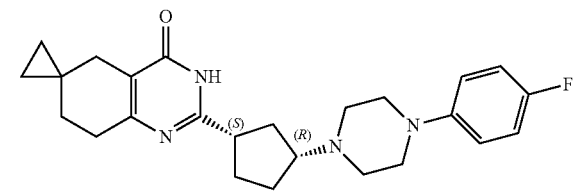

MS (EI) m/z: 423.17 (M+1).

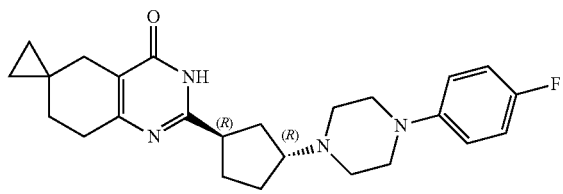

MS (EI) m/z: 423.12 (M+1).

Title compounds were prepared in manner as depicted in step 6 of Example 14.

Step 6: Hydrochloride salt of 2'-((1S,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 151 hydrochloride salt), and Hydrochloride salt of 2'-((1R,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 152 hydrochloride salt).

Title compounds were prepared in manner as depicted in step 7 of Example 14.

Compound 151 hydrochloride salt:
$^1$H NMR (400 MHz, DMSO-$d_6$): δ 11.05 (s, 1H), 7.14-7.09 (m, 2H), 7.06-7.02 (m, 2H), 3.76-3.70 (m, 3H), 3.59-3.51 (m, 2H), 3.20-3.11 (m, 6H), 2.68-2.66 (m, 2H), 2.31-2.22 (m, 3H), 2.15-2.07 (m, 4H), 1.55-1.52 (m, 2H), 0.40-0.37 (m, 4H).
MS (EI) m/z: 423.29 (M+1). free base Compound 152 hydrochloride salt:
$^1$H NMR (400 MHz, DMSO-$d_6$): δ 11.16 (bs, 1H), 7.14-7.10 (m, 2H), 7.05-7.02 (m, 2H), 3.82-3.76 (m, 3H), 3.58-3.55 (m, 2H), 3.39-3.07 (m, 6H), 2.65-2.62 (m, 2H), 2.47-2.36 (m, 1H), 2.27-2.16 (m, 4H), 2.00-1.96 (m, 2H), 1.54-1.51 (m, 2H), 0.40-0.37 (m, 4H).
MS (EI) m/z: 423.29 (M+1). free base

EXAMPLE 18

Synthesis of 2'-((1R,3S)-3-(4-(3-fluorophenyl)piperazin-1-yl)cyclopentyl)-7',8'-dihydro-3'H-spiro[cyclopropane-1,6'-quinazolin]-4'(5'H)-one hydrochloride salt. (Compound 153 hydrochloride salt)

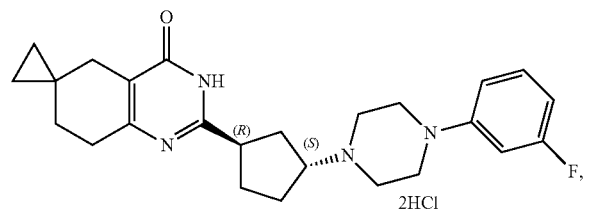

and

2'-((1S,3S)-3-(4-(3-fluorophenyl)piperazin-1-yl)cyclopentyl)-7',8'-dihydro-3'H-spiro[cyclopropane-1,6'-quinazolin]-4'(5'H)-one hydrochloride salt. (Compound 154 hydrochloride salt)

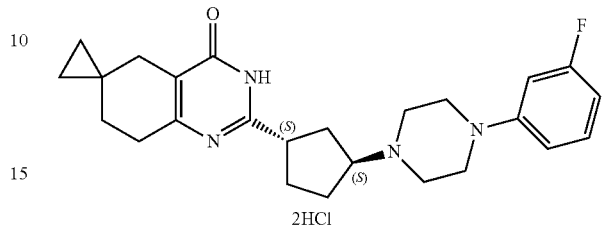

Step 1: (R)-benzyl 8,8-dimethyl-6,10-dioxaspiro[4.5]decane-2-carboxylate

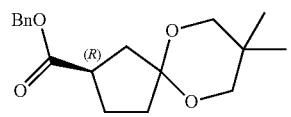

The title compound was made from (R)-8,8-dimethyl-6,10-dioxaspiro[4.5]decane-2-carboxylic acid (prepared following process provided in U.S. Pat. No. 5,675,005 and US20080161564) following the procedure described in Step 1 of Example 16
MS m/z: 305.0
$^1$H NMR (400 MHz, CDCl$_3$): δ 7.39-7.33 (m, 5H), 5.09 (s, 2H), 3.42-3.41 (m, 2H), 3.38-3.36 (m, 2H), 2.96-2.87 (m, 1H), 2.22-2.17 (m, 1H), 2.04-1.91 (m, 1H), 1.83-1.77 (m, 4H), 0.89 (s, 3H), 0.86 (s, 3H).

Step 2: (R)-benzyl 3-oxocyclopentanecarboxylate

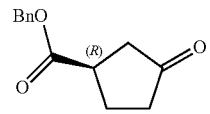

The title compound was made by following the procedure described in Step 2 of Example 16.
GCMS m/z: 218.20.
$^1$H NMR (400 MHz, CDCl$_3$): δ 7.41-7.35 (m, 5H), 5.18 (s, 2H), 3.21-3.18 (m, 1H), 2.55-2.13 (m, 6H).

Step 3: (1R,3S)-benzyl 3-(4-(3-fluorophenyl)piperazin-1-yl)cyclopentanecarboxylate

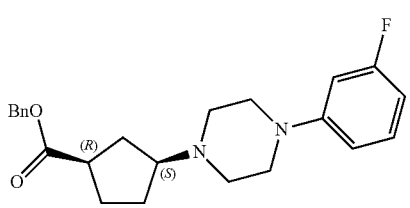

To a solution of (R)-benzyl 3-oxocyclopentanecarboxylate (1.5 g, 6.87 mmol), 1-(3-fluorophenyl)piperazine (1.36 g, 7.56 mmol) in 1,2-dichloroethane (25 ml) were added 1-(3-fluorophenyl)piperazine (1.36 g, 7.56 mmol), glacial acetic acid (0.4 ml, 6.87 mmol) and Sodium triacetoxy borohydride (2.18 g, 10.31 mmol). The mixture was stirred at 25° C. for 24 h before removal of the solvent. The residue was treated with saturated sodium bicarbonate, extracted with ethyl acetate and washed with brine. The organic layer was dried over sodium sulfate, filtered, and concentrated under reduced pressure to afford the crude residue which was purified by column chromatography over silica gel using ethyl acetate in hexane as eluents to obtain the title compound as the major diastereomer (1.2 g, 45.7%).

MS m/z: 383.29 (M+1)

$^1$H NMR (400 MHz, CDCl$_3$): δ 7.39-7.35 (m, 5H), 7.21-7.19 (m, 1H), 6.75-6.69 (m, 2H), 6.55-6.51 (m, 1H), 5.10 (s, 2H), 3.17-3.13 (m, 4H), 2.92-2.86 (m, 1H), 2.57-2.53 (m, 5H), 2.12-2.07 (m, 1H), 1.87-1.83 (m, 3H), 1.51-1.46 (m, 2H).

Step 4: (1R,3S)-3-(4-(4-fluorophenyl)piperazin-1-yl)cyclopentanecarboxylic acid

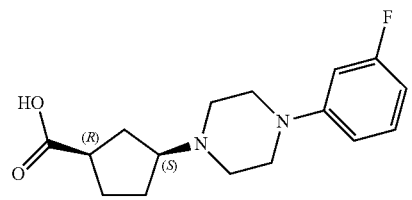

The title compound was made by following the procedure described in Step 6 of Example 16.

MS m/z: 293.40 (M+1)

$^1$H NMR (400 MHz, CDCl$_3$): δ 7.23-7.17 (m, 1H), 6.76-6.69 (m, 2H), 6.55-6.51 (m, 1H), 3.17-3.13 (m, 4H), 2.73-2.68 (m, 1H), 2.57-2.53 (m, 5H), 2.12-2.07 (m, 1H), 1.87-1.83 (m, 3H), 1.51-1.46 (m, 2H).

Step 5: ethyl 6-((1R,3S)-3-(4-(3-fluorophenyl)piperazin-1-yl)cyclopentanecarboxamido)spiro[2.5]oct-5-ene-5-carboxylate

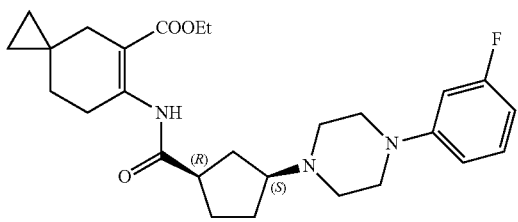

The title compound was made by following the procedure described in step 4 of Example 14.

MS (EI) m/z: 470.0 (M+1).

Step 6: 6-((1R,3S)-3-(4-(3-fluorophenyl)piperazin-1-yl)cyclopentanecarboxamido)spiro[2.5]oct-5-ene-5-carboxylic acid

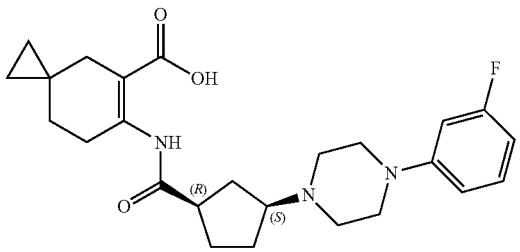

The title compound was made by following the procedure described in step 5 of Example 14.

MS (EI) m/z: 442.11 (M+1).

Step 7: 2'-((1R,3S)-3-(4-(3-fluorophenyl)piperazin-1-yl)cyclopentyl)-7',8'-dihydro-3'H-spiro[cyclopropane-1,6'-quinazolin]-4'(5'H)-one. and 2'-((1S,3S)-3-(4-(3-fluorophenyl)piperazin-1-yl)cyclopentyl)-7',8'-dihydro-3'H-spiro[cyclopropane-1,6'-quinazolin]-4'(5'H)-one.

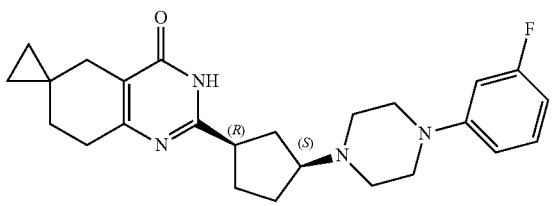

MS (EI) m/z: 423.17 (M+1).

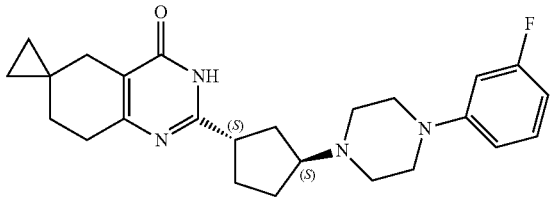

MS (EI) m/z: 423.1 (M+1).

The title compounds were made following the procedure described in step 6 of Example 14.

Step 8: Hydrochloride salt of 2'-((1R,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 153 hydrochloride salt), and Hydrochloride salt of 2'-((1S,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 154 hydrochloride salt).

The title compounds were made by following the procedure described in step 7 of Example 14.

Compound 153 hydrochloride salt:
¹H NMR (400 MHz, DMSO-d6): δ 11.06 (s, 1H), 7.31-7.25 (m, 1H), 6.89-6.84 (m, 2H), 6.67-6.63 (m, 1H), 3.91-3.90 (m, 2H), 3.75-3.71 (m, 1H), 3.57 (bs, 2H), 3.18-315 (m, 5H), 2.68-2.63 (m, 2H), 2.46-2.22 (m, 4H), 2.13-2.09 (m, 4H), 1.55-1.52 (m, 2H), 0.42-0.37 (m, 4H).
MS (EI) m/z: 423.17 (M+1) (free base).

Compound 154 hydrochloride salt:
¹H NMR (400 MHz, DMSO-d6): δ 11.06 (s, 1H), 7.31-7.27 (m, 1H), 6.89-6.84 (m, 2H), 6.68-6.63 (m, 1H), 3.94-3.82 (m, 2H), 3.80-3.76 (m, 1H), 3.57-3.55 (m, 2H), 3.34-3.30 (m, 1H), 3.16-3.14 (m, 4H), 2.68-2.60 (m, 2H), 2.46-2.32 (m, 2H), 2.29-2.15 (m, 4H), 2.00-1.90 (m, 1H), 1.87-1.80 (m, 1H), 1.53-1.50 (m, 2H), 0.41-0.36 (m, 4H).
MS (EI) m/z: 423.23 (M+1) (free base).

EXAMPLE 19

Synthesis of 2'-((1S,3R)-3-(4-(3-fluorophenyl)piperazin-1-yl)cyclopentyl)-7',8'-dihydro-3'H-spiro[cyclopropane-1,6'-quinazolin]-4'(5'H)-one hydrochloride salt. (Compound 155 hydrochloride salt)

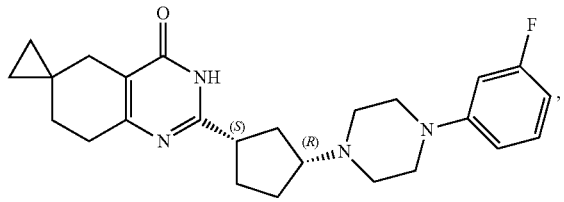

and

2'-((1R,3R)-3-(4-(3-fluorophenyl)piperazin-1-yl)cyclopentyl)-7',8'-dihydro-3'H-spiro[cyclopropane-1,6'-quinazolin]-4'(5'H)-one hydrochloride salt. (Compound 156 hydrochloride salt)

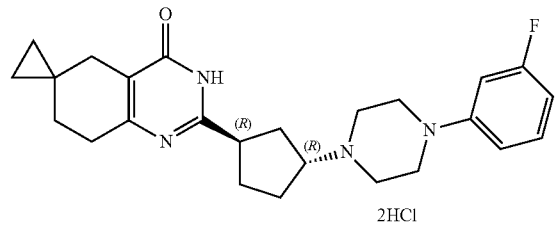

Step 1: (S)-ethyl 6-(8,8-dimethyl-6,10-dioxaspiro[4.5]decane-2-carboxamido)spiro[2.5]oct-5-ene-5-carboxylate.

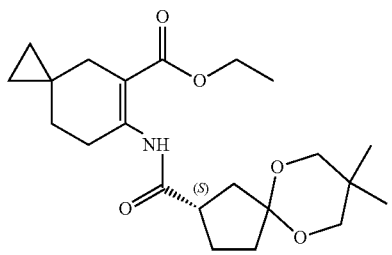

The title compound was made by following the procedure described in step 4 of Example 14 using (S)-8,8-dimethyl-6,10-dioxaspiro[4.5]decane-2-carboxylic acid as a starting material.
MS m/z: 392 (M+1).

Step 2: (S)-ethyl 6-(3-oxocyclopentanecarboxamido)spiro[2.5]oct-5-ene-5-carboxylate.

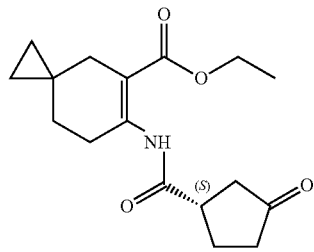

The title compound was made by following the procedure described Step 2 in Example 16.
MS m/z: 306 (M+1)

Step 3: ethyl 6-((1S,3R)-3-(4-(3-fluorophenyl)piperazin-1-yl)cyclopentanecarboxamido)spiro[2.5]oct-5-ene-5-carboxylate.

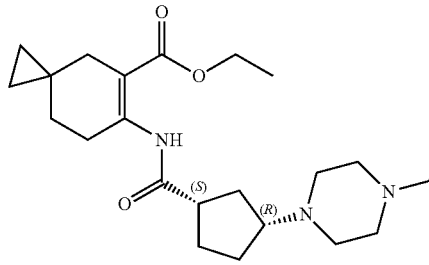

The title compound was made by following the procedure described in step 3 of Example 18.
MS m/z: 470.11 (M+1).

Step 4: 6-((1S,3R)-3-(4-(3-fluorophenyl)piperazin-1-yl)cyclopentanecarboxamido)spiro[2.5]oct-5-ene-5-carboxylic acid.

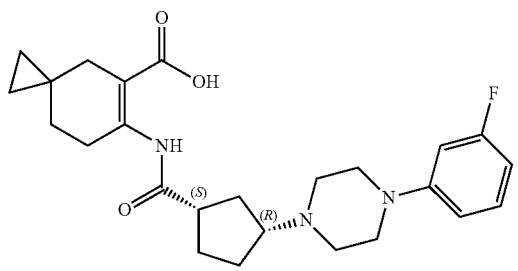

The title compound was made by following the procedure described in step 5 of Example 14.
MS m/z: 442.11 (M+1).

Step 5: ((1S,3R)-3-(4-(3-fluorophenyl)piperazin-1-yl)cyclopentyl)-7',8'-dihydro-3'H-spiro[cyclopropane-1,6'-quinazolin]-4'(5'H)-one & 2'-((1R,3R)-3-(4-(3-fluorophenyl)piperazin-1-yl)cyclopentyl)-7',8'-dihydro-3'H-spiro[cyclopropane-1,6'-quinazolin]-4'(5'H)-one.

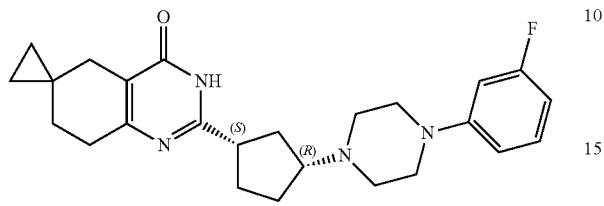

MS (EI) m/z: 423.17 (M+1).

MS (EI) m/z: 423.12 (M+1).

The title compounds were made by following the procedure described in step 6 of Example 14.

Step 6: Hydrochloride salt of 2'-((1S,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 155 hydrochloride salt). and hydrochloride salt of 2'-((1R,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 156 hydrochloride salt).

The title compounds were made by following the procedure described in step 7 in Example 14.

Compound 155 hydrochloride salt:

$^1$H NMR (400 MHz, DMSO-d6): δ 11.27 (bs, 1H), 7.31-7.25 (m, 1H), 6.89-6.84 (m, 2H) 6.67-6.62 (m, 1H), 3.90-3.45 (m, 5H), 3.21-3.18 (m, 5H), 2.70-2.68 (t, 2H), 2.47-2.43 (m, 2H), 2.30-2.23 (m, 3H), 2.13-2.04 (m, 3H), 1.54-1.52 (t, 2H), 0.41-0.37 (m, 4H).

MS (EI) m/z: 423.17 (M+1). free base

Compound 156 hydrochloride salt:

$^1$H NMR (400 MHz, DMSO-d$_6$): δ 11.16 (bs, 1H), 7.14-7.10 (m, 2H), 7.05-7.02 (m, 2H), 3.82-3.76 (m, 3H), 3.58-3.55 (m, 2H), 3.39-3.07 (m, 6H), 2.65-2.62 (m, 2H), 2.47-2.36 (m, 1H), 2.27-2.16 (m, 4H), 2.00-1.96 (m, 2H), 1.54-1.51 (m, 2H), 0.40-0.37 (m, 4H).

MS (EI) m/z: 423.07 (M+1). free base.

EXAMPLE 20

Preparation of 3-(4-(4-fluorophenyl) piperazin-1-yl)-4,4-dimethylcyclopent-1-enecarbonitrile

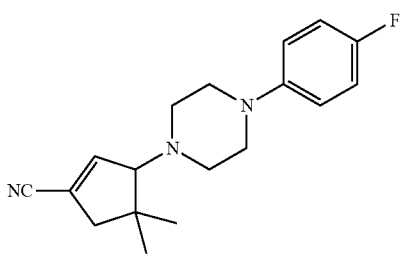 [SMILES: CC1(C)CC(C#N)=CC1N1CCN(c2ccc(F)cc2)CC1]

Step 1:
4,4-dimethyl-3-oxocyclopent-1-enecarbonitrile

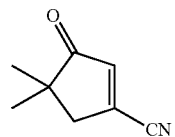

To a stirred solution of 2-bromo-5,5-dimethylcyclopent-2-enone (prepared according to procedure reported in Organic Letters 2002, 4, 71-74, 17 g, 90 mmol) in methanol (200 ml) was added acetic acid, (5.15 ml, 90 mmol) at 25-30° C. Solid potassium cyanide (11.71 g, 180 mmol) was added and continued stirring the reaction mass for 4-5 h at 25-30° C. The progress of reaction was monitored by TLC. After completion of reaction, filtered the reaction mass through cotton filter and then filtrate was concentrated under reduced pressure. A crude oily compound was dissolved in Ethyl acetate (500 ml) and washed with water (100 ml) to remove the unreacted potassium cyanide. Organic layer was dried over sodium sulphate and concentrated under reduced pressure till dryness. Crude compound was purified over silica gel (100-200 mesh) by using 10% ethylacetated in hexane as eluent to obtain title produced (7.1 g)

$^1$H NMR (400 MHz, CDCl$_3$): δ 6.73 (s, 1H), δ 2.76 (s, 2H) 1.19 (s, 6H)

Step 2:
3-hydroxy-4,4-dimethylcyclopent-1-enecarbonitrile.

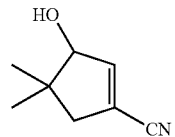

To a stirred solution of 4,4-dimethyl-3-oxocyclopent-1-enecarbonitrile (Step 1, 6 g, 44.4 mmol) in methanol (50 ml) was added sodium borohydride (2.52 g, 66.6 mmol) at 0° C. under nitrogen atmosphere. Reaction mixture was stirred at same temperature for 20 mins. Progress of reaction was monitored by TLC. After completion of reaction, distilled the reaction mixture was concentrated under reduced pressure. To crude reaction mass water (10 ml) was added followed by addition of 1 ml acetic acid. Aqueous reaction mixture was extracted in ethyl acetate (2×25 ml). Combined organic layer was dried on sodium sulphate and concentrated under reduced pressure to get oily compound which was directly used for next reaction without further purification (3.9 g).

$^1$H NMR (400 MHz, CDCl$_3$): δ 6.57 (s, 1H), δ 4.39 (d, J=1.2 Hz, 1H) 2.52-2.51 (m, 1H) 2.39-2.34 (m, 1H) 1.11 (s, 6H)

Step 3: 3-(4-(4-fluorophenyl) piperazin-1-yl)-4,4-dimethylcyclopent-1-enecarbonitrile.

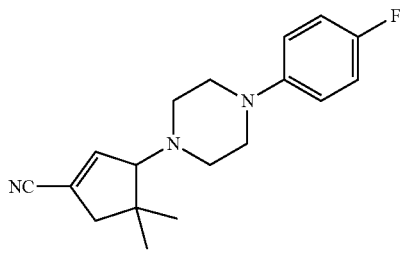 [SMILES: CC1(C)CC(C#N)=CC1N1CCN(c2ccc(F)cc2)CC1]

To a stirred solution of 3-hydroxy-4,4-dimethylcyclopent-1-enecarbonitrile (1.5 g, 10.93 mmol) in dichloromethane (20 ml) was added diisopropylethylamine, (5.73 ml, 32.8 mmol) under nitrogen atmosphere. Reaction mixture was cooled to 0-5° C. Methane sulfonyl chloride (1.278 ml, 16.40 mmol) in 2 ml dichloromethane was added drop wise at 0-5° C. in 10 mins. Reaction mixture was stirred at 0-5° C. for 3 h. Progress of reaction was monitored by TLC. Reaction mixture was diluted with dichloromethane (20 ml) and washed with water (2×10 ml), organic layer was dried on sodium sulfate and concentrated under reduced pressure to get sticky compound which was dissolved in dry N,N-dimethylformamide (15 ml) and cooled to 0-5° C. followed by addition of diisopropylethylamine (5.73 ml, 32.8 mmol) and 1-(4-fluorophenyl)piperazine (1.971 g, 10.93 mmol) under nitrogen atmosphere. Reaction mixture was gradually warmed to 25-30° C. and stirring continued for 16 h. Progress of reaction was monitored by TLC. Reaction mixture was concentrated under reduced pressure to obtain crude product which was dissolved in ethyl acetate (100 ml) and washed with water (3×25 ml). Combined organic layer was dried on sodium sulphate and concentrated under reduced pressure to get crude oily product. Crude compound was purified over silica gel (100-200 mesh) by flash column chromatography using 20% ethyl acetate in hexane to obtain title compound (0.260 g).

$^1$H NMR (400 MHz, CDCl$_3$): δ 6.97 (t, J=8.4 Hz, 2H), 6.88-6.85 (m, 2H) 6.78 (d, J=2 Hz, 1H) 3.29-3.27 (m, 1H) 3.11-3.08 (m, 4H) 2.76-2.74 (m, 4H) 2.47 (d, J=16 Hz, 1H) 2.32 (d, J=16 Hz, 1H) 1.12 (s, 6H)

MS: m/z 299.9 (M+1)

EXAMPLE 21

Synthesis of (R)-3-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzonitrile

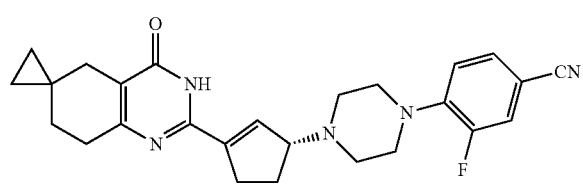 [SMILES: N#Cc1ccc(N2CCN([C@H]3C=C(c4nc5c(c(=O)[nH]4)CC4(CC5)CC4)CC3)CC2)c(F)c1]

To a stirred solution of (R)-2'-(3-(4-(2-fluoro-4-iodophenyl)piperazin-1-yl)cyclopent-1-en-1-yl)-7',8'-dihydro-3'H-spiro[cyclopropane-1,6'-quinazolin]-4'(5'H)-one (synthesis from (R)-3-aminocyclopent-1-enecarbonitrile and 2-fluoro-4-iodoaniline as described in example 11) (0.160 g, 0.293 mmol) in N,N-dimethylformamide (10 ml) was added dicyanozinc (0.344 g, 2.93 mmol) at 25° C. The reaction mixture was heated to 115-120° C. for 4 h. Progress of the reaction was monitored by TLC. After completion of reaction, reaction mixture was cooled and solvent was evaporated under reduced pressure to obtain crude product. Crude product was purified by flash column chromatography over silica gel (110-200 mesh) using 6% methanol in in dichloromethane as eluent to obtain title compound (0.045 g, 34.5%).

$^1$H NMR (400 MHz, DMSO-d$_6$) δ 10.40 (bs, 1H, D$_2$O exchangeable), 7.78 (d, J=13.1 Hz, 1H), 7.59 (d, J=8.5 Hz, 1H), 7.25 (t, J=8.6 Hz, 1H), 6.88 (s, 1H), 4.68 (m, 1H) 3.75-3.70 (m, 2H), 3.41-3.15 (m, 6H), 2.85-2.75 (m, 2H), 2.65-2.55 (m, 2H), 2.38-2.30 (m, 2H), 2.26 (s, 2H), 1.54 (t, J=6.1 Hz, 2H), 0.42-0.39 (m, 4H).

MS: m/z 446 (M+1)

EXAMPLE 22

PARP1 Biochemical Assay

The assay was performed using BPS Bioscience kit. The 96-well strip plate was coated with 50 µl of histone mixture and incubated at 4° C. overnight. Next day the wells were blocked by adding 100 µl of blocking buffer. The plate was washed and 25 µl of appropriate concentration of PARP1 (25-75 ng/well) was added in all the Test and Positive control wells. In Negative control wells enzyme was replaced with 25 µl of water. To it 5 µl each of 10×PARP assay buffer and activated DNA was added in all the wells (Test, Positive and Negative control wells). 10× concentration of test compounds were prepared and 5 µl test compounds were added respective wells. Reaction volume was made up to 45 µl by adding water to all the wells. Finally, 5 µl of 10×PARP assay mixture containing biotinilated NAD$^+$ was added in each well and the plate was incubated at ambient temperature (25° C.) for 60 min. After washing the plate 50 µl of Streptavidin-HRP was added in each well and incubated the plate at RT for 30 min. The plate was washed and the luminescence was read in PHERAStar plate reader after adding 100 µl of chemiluminescent substrate.

PARP inhibition was calculated using the following formula:

% PARP inhibition=100−[(RLU test compound treated sample−RLU negative control)/(RLU Positive control−RLU negative control)×100]

IC$_{50}$ values were calculated by plotting % inhibition against the respective concentrations of test compounds using GraphPad Prism 5.

PARP 1 inhibition IC$_{50}$ of the compounds of invention is provided in table 1 below: Compounds with IC$_{50}$ between 1 nM and 500 nM are grouped under group A, compounds with IC$_{50}$ between 501 nM and 5000 nM are grouped under group B, and compounds with IC$_{50}$ between 5001 nM and 500 µM are grouped under group C.

TABLE 1

| Group | Compound Nos |
|---|---|
| A | 1, 2, 3, 5, 6, 7, 9, 12, 14, 19, 21, 24, 27, 28, 29, 30, 32, 34, 37, 38, 39, 40, 42, 44, 46, 47, 48, 49, 50, 51, 52, 53, 54, 56, 57, 58, 61, 62, 63, 65, 68, 72, 73, 74, 75, 76, 77, 78, 79, 80, 82, 83, 84, 85, 86, 87, 88, 89, 90, 91, 92, 93, 94, 95, 96, 97, 98, 100, 101, 103, 104, 106, 107, 108, 109, 111, 113, 114, 116, 117, 119, 122, 123, 124, 125, 127, 129, 132, 133, 134, 137, 141, 142, 143, 145, 146, 147, 149, 150, 151, 154. |
| B | 4, 10, 11, 13, 25, 55, 60, 64, 81, 99, 102, 105, 110, 112, 115, 118, 120, 126, 130, 131, 136, 138, 140, 144, 148, 152, 155, 157, 158. |
| C | 8, 15, 16, 17, 18, 20, 22, 23, 26, 31, 33, 35, 36, 41, 43, 45, 59, 66, 67, 69, 70, 71, 121, 128, 135, 139, 153, 156, 159. |

The invention claimed is:

1. A compound of the general formula (I), its tautomeric form, its stereoisomer, or its pharmaceutically acceptable salt,

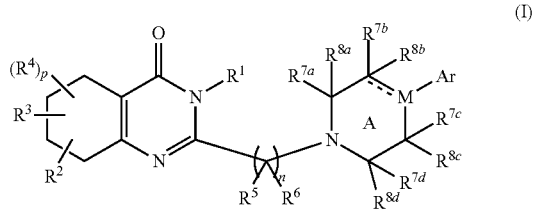

wherein,

M is selected from C, CH, and N;

===== is a single bond when M is selected as N, and ===== is either a single or a double bond when M is selected as CH or C respectively;

$R^1$ is selected from hydrogen, and substituted- or unsubstituted-alkyl;

$R^2$ and $R^3$ groups are attached either to the same carbon atom or adjacent or non-adjacent carbon atoms of the carbocylic ring, and $R^2$ and $R^3$ together with the carbon atom(s) to which they are attached form a substituted- or unsubstituted carbocycle;

$R^4$ is selected independently at each occurrence from halogen, cyano, substituted- or unsubstituted-alkyl, —$OR^9$, and —$N(R^{10})R^{11}$;

$R^5$ and $R^6$ are each independently selected from hydrogen, halogen, substituted- or unsubstituted-alkyl, perhaloalkyl, substituted- or unsubstituted-cycloalkyl, —$OR^9$, and —$N(R^{10})R^{11}$, or $R^5$ and $R^6$ together constitute oxo (=O), or both $R^5$ and $R^6$ attached to the same carbon atom or adjacent or non-adjacent carbon atoms together with the carbon atom(s) to which they are attached form a substituted- or unsubstituted-carbocycle, or when they are attached to adjacent carbon atoms, form a pi bond linking the said carbon atoms.

$R^{7a}$, $R^{8a}$, $R^{7b}$, $R^{8b}$, $R^{7c}$, $R^{8c}$, $R^{7d}$, and $R^{8d}$ are each independently selected from hydrogen, halogen, substituted- or unsubstituted-alkyl, —$OR^9$, and —$N(R^{10})R^{11}$; or any two groups out of $R^{7a}$, $R^{8a}$, $R^{7b}$, $R^{8b}$, $R^{7c}$, $R^{8c}$, $R^{7d}$, and $R^{8d}$ form oxo (=O), or any two groups out of $R^{7a}$, $R^{8a}$, $R^{7b}$, $R^{8b}$, $R^{7c}$, $R^{8c}$, $R^{7d}$, and $R^{8d}$ taken together with the carbon atom(s) to which they are attached form a substituted- or unsubstituted-carbocycle, or a substituted- or unsubstituted heterocycle, thereby making ring 'A' either a spiro-bicycle or a fused-bicycle or a bridged-bicycle;

Ar is selected from substituted- or unsubstituted-aryl and substituted- or unsubstituted heteroaryl;

p is an integer selected from 0, 1, 2 and 3;

n is an integer selected from 1, 2, 3, and 4;

$R^9$ is selected from hydrogen and substituted- or unsubstituted-alkyl;

$R^{10}$ and $R^{11}$ are each independently selected from hydrogen and substituted- or unsubstituted-alkyl;

when an alkyl group or alkenyl group is substituted, each of them is substituted with 1 to 4 substituents independently selected from oxo (=O), halogen, cyano, perhaloalkyl, cycloalkyl, cycloalkenyl, aryl, heteroaryl, heterocyclyl, —$OR^{12a}$, —$SO_2$(alkyl), —C(=O)O(alkyl), —C(=O)N(H)$R^{12}$, —C(=O)N(alkyl)$_2$, —N(H)C(=O)(alkyl), —N(H)$R^{12}$, and —N(alkyl)$R^{12}$;

when 'cycloalkyl', 'cycloalkenyl' and 'carbocycle' is substituted, the cycloalkyl, cycloalkenyl, or carbocycle group is substituted with 1 to 4 substituents independently selected from oxo (=O), halogen, cyano, alkyl, alkenyl, perhaloalkyl, —$OR^{12}$, —$SO_2$(alkyl), —C(=O)O(alkyl), —C(=O)N(H)$R^{12}$, —C(=O)N(alkyl)$R^{12}$, —N(H)C(=O)(alkyl), —N(H)$R^{12}$, and —N(alkyl)$_2$;

when the aryl group is substituted, it is substituted with 1 to 4 substituents independently selected from halogen, nitro, cyano, hydroxy, alkyl, alkenyl, perhaloalkyl, cycloalkyl, cycloalkenyl, heterocyclyl, aryl, heteroaryl, —O-alkyl, —O-perhaloalkyl, —N(alkyl)alkyl, —N(H)alkyl, —NH$_2$, 13 $SO_2$-alkyl, —$SO_2$-perhaloalkyl, —N(alkyl)C(=O)alkyl, —N(H)C(=O)alkyl, —C(=O)N(alkyl)alkyl, —C(=O)N(H)alkyl, —C(=O)N(H)cycloalkyl, —C(=O)NH$_2$, —$SO_2$N(alkyl)alkyl, —$SO_2$N(H)alkyl, —$SO_2$NH$_2$, —C(=O)OH, —C(=O)O-alkyl, —O(C=O)N(alkyl)H, —O(C=O)N(alkyl)$_2$, —O(C=O)N(cycloalkyl)H, —N(H)C(=O)N(aryl)H, —N(H)C(=O)N(alkyl)H, and —N(H)C(=O)NH$_2$;

when the heteroaryl group is substituted, it is substituted with 1 to 4 substituents independently selected from halogen, nitro, cyano, hydroxy, alkyl, alkenyl, perhaloalkyl, cycloalkyl, cycloalkenyl, heterocyclyl, aryl, heteroaryl, —O-alkyl, —O-perhaloalkyl, —N(alkyl)alkyl, —N(H)alkyl, —NH$_2$, —$SO_2$-alkyl, —$SO_2$-perhaloalkyl, —N(alkyl)C(=O)alkyl, —N(H)C(=O)alkyl, —C(=O)N(alkyl)alkyl, —C(=O)N(H)alkyl, —C(=O)N(H)cycloalkyl, —C(=O)NH$_2$, —$SO_2$N(alkyl)alkyl, —$SO_2$N(H)alkyl, —$SO_2$NH$_2$, —C(=O)OH, —C(=O)O-alkyl, —O(C=O)N(alkyl)H, —O(C=O)N(alkyl)$_2$, —O(C=O)N(cycloalkyl)H, —N(H)C(=O)N(aryl)H, —N(H)C(=O)N(alkyl)H, and —N(H)C(=O)NH$_2$;

when the heterocyclic group is substituted, it is substituted either on a ring carbon atom or on a ring hetero atom, and when it is substituted on a ring carbon atom, it is substituted with 1 to 4 substituents independently selected from oxo (=O), halogen, cyano, alkyl, alkenyl, perhaloalkyl, —$OR^{12}$, —$SO_2$(alkyl), —C(=O)O(alkyl), —C(=O)N(H)$R^{12}$, —C(=O)N(alkyl)$R^{12}$, —N(H)C(=O)(alkyl), —N(H)$R^{12}$, and —N(alkyl)$_2$; and when the heterocyclic group is substituted on a ring nitrogen, it is substituted with substituents independently selected from alkyl, alkenyl, cycloalkyl, cycloalkenyl, aryl, heteroaryl, —$SO_2$(alkyl), —C(=O)(alkyl), C(=O)O(alkyl), —C(=O)N(H)$R^{12}$, and —C(=O)N(alkyl)$R^{12}$;

$R^{12}$ is selected from hydrogen and alkyl; and $R^{12a}$ is selected from hydrogen, alkyl, alkenyl, and perhaloalkyl.

2. The compound of formula (I), its tautomeric form, its stereoisomer, or its pharmaceutically acceptable salt, as claimed in claim 1, wherein n is 3.

3. The compound of formula (I), its tautomeric form, its stereoisomer, or its pharmaceutically acceptable salt, as claimed in claim 1, wherein $R^5$ and $R^6$ are each independently selected from hydrogen and methyl.

4. The compound of formula (I), its tautomeric form, its stereoisomer, or its pharmaceutically acceptable salt, as claimed in claim 1, wherein $R^5$, $R^6$ and the carbon atoms to which they are attached together form a substituted- or unsubstituted carbocycle, the said substituted- or unsubstituted carbocycle is selected from

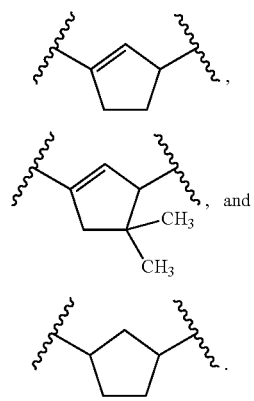

5. The compound of formula (I), its tautomeric form, its stereoisomer, or its pharmaceutically acceptable salt, as claimed in claim 1, wherein Ar is selected from substituted- or unsubstituted-phenyl, substituted- or unsubstituted-pyridinyl, substituted- or unsubstituted-thiazolyl, substituted- or unsubstituted-thiophenyl, and substituted- or unsubstituted-benzothiazolyl, wherein the substituted-phenyl, substituted-pyridinyl, substituted-thiazolyl, or substituted-benzothiazolyl group is substituted with 1-3 substituents independently selected from halo, cyano, thiophenyl, phenyl, methyl, ethyl, trifluoromethyl, methoxy, N-methylcarbamoyl, N,N-dimethylcarbamoyl, and N-cyclopropylcarbamoyl.

6. The compound of formula (I), its tautomeric form, its stereoisomer, or its pharmaceutically acceptable salt, as claimed in claim 1, wherein Ar is selected from

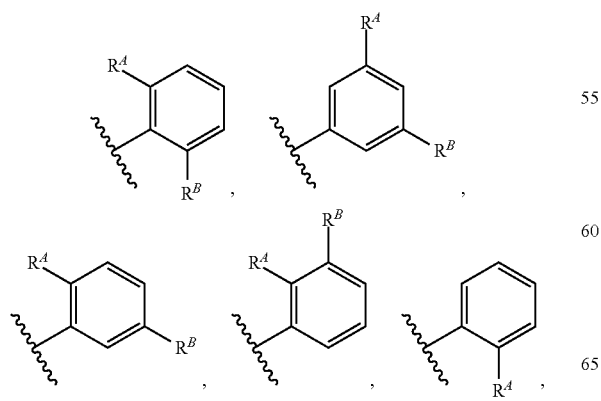

-continued

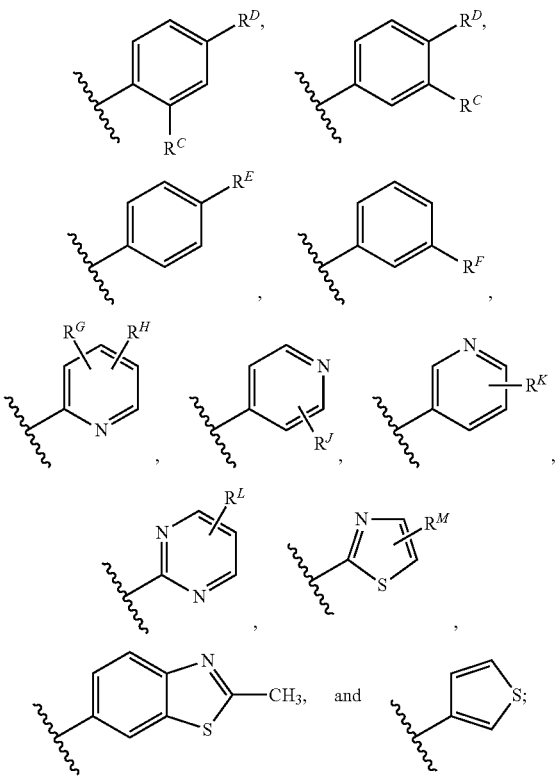

wherein, $R^A$ and $R^B$ are independently selected from halogen and methyl, $R^C$ is selected from halogen, methyl and methoxy, $R^D$ is selected from halogen, cyano, methyl, and N-methylcarbamoyl, $R^E$ is selected from hydrogen, halogen, methyl, N-cyclopropylcarbamoyl, N-methylcarbamoyl, N,N-dimethylcarbamoyl, and 3-thiophenyl, $R^F$ is selected from halogen, methyl, N-methylcarbamoyl, and trifluoromethyl, $R^G$ and $R^H$ are independently selected from hydrogen, halogen, methyl, and N-methylcarbamoyl, $R^J$ is selected from hydrogen and methyl, $R^K$ is selected from hydrogen, halogen, methyl and phenyl, $R^L$ is selected from hydrogen and ethyl, and $R^M$ is selected from hydrogen, methyl and N-methylcarbamoyl.

7. The compound of formula (I), its tautomeric form, its stereoisomer, or its pharmaceutically acceptable salt, as claimed in claim 1, wherein ring A is selected from

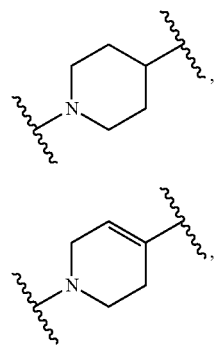

-continued

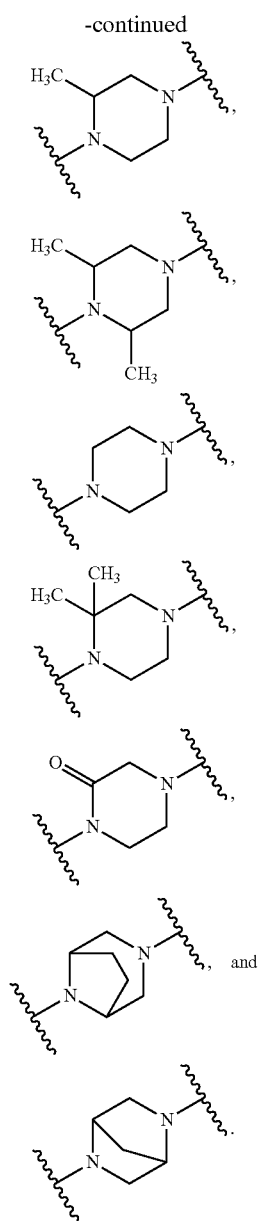

8. The compound of formula (I), its tautomeric form, its stereoisomer, or its pharmaceutically acceptable salt, as claimed in claim 1, wherein the compound is selected from:

2'-(3-(4-(4-fluorophenyl)piperazin-1-yl)propyl)-6',7'-dihydro-3'H-spiro[cyclopropane-1,8'-quinazolin]-4'(5'H)-one (Compound 1);

2'-(3-(4-(4-chlorophenyl)piperazin-1-yl)propyl)-6',7'-dihydro-3'H-spiro[cyclopropane-1,8'-quinazolin]-4'(5'H)-one (Compound 2);

2'-(3-(4-phenyl-5,6-dihydropyridin-1(2H)-yl)propyl)-6',7'-dihydro-3'H-spiro[cyclopropane-1,8'-quinazolin]-4'(5'H)-one (Compound 3);

2'-(3-(3-(4-fluorophenyl)-3,8-diazabicyclo[3.2.1]octan-8-yl)propyl)-4a',5',6',7'-tetrahydro-3'H-spiro[cyclopropane-1,8'-quinazolin]-4'(8a'H)-one (Compound 4);

2'-(3-(4-(4-fluorophenyl)piperazin-1-yl)propyl)-7',8'-dihydro-3'H-spiro[cyclopropane-1,6'-quinazolin]-4'(5'H)-one (Compound 5);

2'-(3-(4-(4-chlorophenyl)piperazin-1-yl)propyl)-7',8'-dihydro-3'H-spiro[cyclopropane-1,6'-quinazolin]-4'(5'H)-one (Compound 6);

2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one (Compound 7);

2'-(3-(8-(4-fluorophenyl)-3,8-diazabicyclo[3.2.1]octan-3-yl)propyl)-7',8'-dihydro-3'H-spiro[cyclopropane-1,6'-quinazolin]-4'(5'H)-one (Compound 8);

2'-(3-(4-(4-fluorophenyl)-5,6-dihydropyridin-1(2H)-yl)propyl)-7',8'-dihydro-3'H-spiro[cyclopropane-1,6'-quinazolin]-4'(5'H)-one (Compound 9);

2'-(3-(4-(3,4-dichlorophenyl)piperazin-1-yl)propyl)-7',8'-dihydro-3'H-spiro[cyclopropane-1,6'-quinazolin]-4'(5'H)-one (Compound 10);

2'-(3-(5-(4-fluorophenyl)-2,5-diazabicyclo[2.2.1]heptan-2-yl)propyl)-7',8'-dihydro-3'H-spiro[cyclopropane-1,6'-quinazolin]-4'(5'H)-one (Compound 11);

2'-(3-(3-(4-fluorophenyl)-3,8-diazabicyclo[3.2.1]octan-8-yl)propyl)-7',8'-dihydro-3'H-spiro[cyclopropane-1,6'-quinazolin]-4'(5'H)-one (Compound 12);

2'-(3-(4-phenylpiperazin-1-yl)propyl)-7',8'-dihydro-3'H-spiro[cyclopropane-1,6'-quinazolin]-4'(5'H)-one (Compound 13);

2'-(3-(4-(2-chlorophenyl)piperazin-1-yl)propyl)-7',8'-dihydro-3'H-spiro[cyclopropane-1,6'-quinazolin]-4'(5'H)-one (Compound 14);

2'-(3-(4-(4-fluorophenyl)piperazin-1-yl)propyl)-5',6'-dihydro-3'H-spiro[cyclopropane-1,7'-quinazolin]-4'(8'H)-one (Compound 15);

2'-(3-(4-(4-fluorophenyl)-5,6-dihydropyridin-1(2H)-yl)propyl)-5',6'-dihydro-3'H-spiro[cyclopropane-1,7'-quinazolin]-4'(8'H)-one (Compound 16);

2'-(3-(4-phenyl-5,6-dihydropyridin-1(2H)-yl)propyl)-5',6'-dihydro-3'H-spiro[cyclopropane-1,7'-quinazolin]-4'(8'H)-one (Compound 17);

2'-(3-(4-(3-chlorophenyl)piperazin-1-yl)propyl)-7',8'-dihydro-3'H-spiro[cyclopropane-1,6'-quinazolin]-4'(5'H)-one (Compound 18);

2'-(3-(4-phenylpiperidin-1-yl)propyl)-7',8'-dihydro-3'H-spiro[cyclopropane-1,6'-quinazolin]-4'(5'H)-one (Compound 19);

2'-(3-(4-(pyridin-2-yl)piperazin-1-yl)propyl)-7',8'-dihydro-3'H-spiro[cyclopropane-1,6'-quinazolin]-4'(5'H)-one (Compound 20);

2'-(3-(4-(4-fluorophenyl)piperazin-1-yl)butyl)-7',8'-dihydro-3'H-spiro[cyclopropane-1,6'-quinazolin]-4'(5'H)-one (Compound 21);

2'-(3-(4-(3-(trifluoromethyl)phenyl)piperazin-1-yl)propyl)-7',8'-dihydro-3'H-spiro[cyclopropane-1,6'-quinazolin]-4'(5'H)-one (Compound 22);

2'-(3-(4-(m-tolyl)piperazin-1-yl)propyl)-7',8'-dihydro-3'H-spiro[cyclopropane-1,6'-quinazolin]-4'(5'H)-one (Compound 23);

2-(3-(4-(4-fluorophenyl)piperazin-1-yl)propyl)-5a,6,6a,7-tetrahydro-3H-cyclopropa[g]quinazolin-4(5H)-one (Compound 24);

2-(3-(4-phenylpiperazin-1-yl)propyl)-5a,6,6a,7-tetrahydro-3H-cyclopropa[g]quinazolin-4(5H)-one (Compound 25);

2'-(3-(4-(4-fluorophenyl)-2,6-dimethylpiperazin-1-yl)propyl)-7',8'-dihydro-3'H-spiro[cyclopropane-1,6'-quinazolin]-4'(5'H)-one (Compound 26);

2'-(3-(4-(4-fluorophenyl)-2-methylpiperazin-1-yl)propyl)-7',8'-dihydro-3'H-spiro[cyclopropane-1,6'-quinazolin]-4'(5'H)-one (Compound 27);

2'-(3-(4-(2-fluorophenyl)piperazin-1-yl)propyl)-7',8'-dihydro-3'H-spiro[cyclopropane-1,6'-quinazolin]-4'(5'H)-one (Compound 28);

2'-(3-(4-(pyridin-4-yl)piperazin-1-yl)propyl)-7',8'-dihydro-3'H-spiro[cyclopropane-1,6'-quinazolin]-4'(5'H)-one (Compound 29);

2'-(3-(4-(4-fluorophenyl)piperazin-1-yl)-3-methylbutyl)-7',8'-dihydro-3'H-spiro[cyclopropane-1,6'-quinazolin]-4'(5'H)-one (Compound 30);

(E)-2'-(3-(4-(4-fluorophenyl)piperazin-1-yl)-3-methylbut-1-en-1-yl)-7',8'-dihydro-3'H-spiro[cyclopropane-1,6'-quinazolin]-4'(5'H)-one (Compound 31);

2'-(3-(4-(p-tolyl)piperazin-1-yl)propyl)-7',8'-dihydro-3'H-spiro[cyclopropane-1,6'quinazolin]-4'(5'H)-one (Compound 32);

2'-(3-(4-(4-fluorophenyl)-2-oxopiperazin-1-yl)propyl)-7',8'-dihydro-3'H-spiro[cyclopropane-1,6'-quinazolin]-4'(5'H)-one (Compound 33);

2'-(3-(4-(2,4-dichlorophenyl)piperazin-1-yl)propyl)-7',8'-dihydro-3'H-spiro[cyclopropane-1,6'-quinazolin]-4'(5'H)-one (Compound 34);

2-(3-(4-(4-fluorophenyl)piperazin-1-yl)propyl)-5,6,7,8-tetrahydro-5,8-methanoquinazolin-4(3H)-one (Compound 35);

2-(3-(4-(4-chlorophenyl)piperazin-1-yl)propyl)-5,6,7,8-tetrahydro-5,8-methanoquinazolin-4(3H)-one (Compound 36);

(R)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one (Compound 37);

(S)-2'-(3-(4-(4-chlorophenyl)piperazin-1-yl)cyclopent-1-en-1-yl)-7',8'-dihydro-3'H-spiro[cyclopropane-1,6'-quinazolin]-4'(5'H)-one (Compound 38);

2'-(3-(4-(pyridin-4-yl)piperazin-1-yl)cyclopent-1-en-1-yl)-7',8'-dihydro-3'H-spiro[cyclopropane-1,6'-quinazolin]-4'(5'H)-one (Compound 39);

(S)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 40);

(R)-2'-(3-(4-(4-chlorophenyl)piperazin-1-yl)cyclopent-1-en-1-yl)-6',7'-dihydro-3'H-spiro[cyclopropane-1,8'-quinazolin]-4'(5'H)-one (Compound 41);

(R)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 42);

(S)-2'-(3-(4-(4-fluorophenyl)piperazin-1-yl)cyclopent-1-en-1-yl)-7',8'-dihydro-3'H-spiro[cyclopropane-1,6'-quinazolin]-4'(5'H)-one (Compound 43);

N-cyclopropyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 44);

2'-(3-(4-(4-fluorophenyl)-3-oxopiperazin-1-yl)cyclopent-1-en-1-yl)-7',8'-dihydro-3'H-spiro[cyclopropane-1,6'-quinazolin]-4'(5'H)-one (Compound 45);

(R)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H )-one (Compound 46);

(S)-2'-(3-(4-(4-chlorophenyl)-5,6-dihydropyridin-1(2H)-yl)cyclopent-1-en-1-yl)-7',8'-dihydro-3'H-spiro[cyclopropane-1,6'-quinazolin]-4'(5'H )-one (Compound 47);

(R)-2'-(3-(4-(4-fluorophenyl)piperazin-1-yl)cyclopent-1-en-1-yl)-6',7'-dihydro-3'H-spiro[cyclopropane-1,8'-quinazolin]-4'(5'H)-one (Compound 48);

(S)-2'-(3-(4-(4-fluorophenyl)piperazin-1-yl)cyclopent-1-en-1-yl)-6',7'-dihydro-3'H-spiro[cyclopropane-1,8'-quinazolin]-4'(5'H)-one (Compound 49);

2'-(3-(4-(4-bromophenyl)piperazin-1-yl)cyclopent-1-en-1-yl)-7',8'-dihydro-3'H-spiro[cyclopropane-1,6'-quinazolin]-4'(5'H )-one (Compound 50);

(S)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H )-one (Compound 51);

(R)-2'-(3-(4-(4-fluorophenyl)-5,6-dihydropyridin-1(2H)-yl)cyclopent-1-en-1-yl)-7',8'-dihydro-3'H-spiro[cyclopropane-1,6'-quinazolin]-4'(5'H )-one (Compound 52);

(S)-N-methyl-4-(4-(3-(4'-oxo-',5',7',8'-tetrahydro-3'H-spiro[cyclopropane-1,6'-quinazolin]-2'-yl)cyclopent-2-en-1-yl)piperazin-1-yl)benzamide (Compound 53);

(R)-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 54);

(S)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 55);

(R)-2'-(3-(4-(4-chlorophenyl)piperidin-1-yl)cyclopent-1-en-1-yl)-7',8'-dihydro-3'H-spiro[cyclopropane-1,6'-quinazolin]-4'(5'H)-one (Compound 56);

(R)-2'-(3-(4-(5-chloropyridin-2-yl)piperazin-1-yl)cyclopent-1-en-1-yl)-7',8'-dihydro-3'H-spiro[cyclopropane-1,6'-quinazolin]-4'(5'H)-one (Compound 57);

(R)-2'-(3-(4-(5-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 58);

(R)-2'-(3-(4-(3,4-dichlorophenyl)piperazin-1-yl)cyclopent-1-en-1-yl)-7',8'-dihydro-3'H-spiro[cyclopropane-1,6'-quinazolin]-4'(5'H)-one (Compound 59);

(R)-2'-(3-(4-(3-chlorophenyl)piperazin-1-yl)cyclopent-1-en-1-yl)-7',8'-dihydro-3'H-spiro[cyclopropane-1,6'-quinazolin]-4'(5'H)-one (Compound 60);

(R)-2'-(3-(4-(2,4-difluorophenyl)piperazin-1-yl)cyclopent-1-en-1-yl)-7',8'-dihydro-3'H-spiro[cyclopropane-1,6'-quinazolin]-4'(5'H)-one (Compound 61);

(R)-2'-(3-(4-(3,4-difluorophenyl)piperazin-1-yl)cyclopent-1-en-1-yl)-7',8'-dihydro-3'H-spiro[cyclopropane-1,6'-quinazolin]-4'(5'H)-one (Compound 62);

(R)-2'-(3-(4-(4-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 63);

(R)-2'-(3-(4-(3-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 64);

(R)-2'-(3-(4-(2,4-dichlorophenyl)piperazin-1-yl)cyclopent-1-en-1-yl)-7',8'-dihydro-3'H-spiro[cyclopropane-1,6'-quinazolin]-4'(5'H)-one (Compound 65);

(R)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 66);

(R)-2'-(3-(4-(4-fluorophenyl)-2,2-dimethylpiperazin-1-yl)cyclopent-1-en-1-yl)-7',8'-dihydro-3'H-spiro[cyclopropane-1,6'-quinazolin]-4'(5'H)-one (Compound 67);

(R)-3-fluoro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 68);

(R)-N,N-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 69);

(R)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 70);

(S)-2'-(3-(4-(4-fluorophenyl)piperazin-1-yl)-4,4-dimethylcyclopent-1-en-1-yl)-7',8'-dihydro-3'H-spiro[cyclopropane-1,6'-quinazolin]-4'(5'H)-one (Compound 71);

(R)-N-methyl-4-(1-(3-(4'-oxo-4',5',7',8'-tetrahydro-3'H-spiro[cyclopropane-1,6'-quinazolin]-2'-yl)cyclopent-2-en-1-yl)-1,2,3,6-tetrahydropyridin-4-yl)benzamide (Compound 72);

(R)-2'-(3-(4-(p-tolyl)piperazin-1-yl)cyclopent-1-en-1-yl)-7',8'-dihydro-3'H-spiro[cyclopropane-1,6'-quinazolin]-4'(5'H)-one (Compound 73);

(R)-2'-(3-(4-(4-methoxyphenyl)piperazin-1-yl)cyclopent-1-en-1-yl)-7',8'-dihydro-3'H-spiro[cyclopropane-1,6'-quinazolin]-4'(5'H)-one (Compound 74);

(R)-2'-(3-(4-(4-fluorophenyl)piperidin-1-yl)cyclopent-1-en-1-yl)-7',8'-dihydro-3'H-spiro[cyclopropane-1,6'-quinazolin]-4'(5'H)-one (Compound 75);

(R)-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 76);

(R)-2'-(3-(4-(p-tolyl)piperidin-1-yl)cyclopent-1-en-1-yl)-7',8'-dihydro-3'H-spiro[cyclopropane-1,6'-quinazolin]-4'(5'H)-one (Compound 77);

(R)-2'-(3-(4-(3-fluorophenyl)piperazin-1-yl)cyclopent-1-en-1-yl)-7',8'-dihydro-3'H-spiro[cyclopropane-1,6'-quinazolin]-4'(5'H)-one (Compound 78);

(R)-2'-(3-(4-(2-chloro-4-fluorophenyl)piperazin-1-yl)cyclopent-1-en-1-yl)-7',8'-dihydro-3'H-spiro[cyclopropane-1,6'-quinazolin]-4'(5'H)-one (Compound 79);

(R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 80);

(R)-2'-(3-(4-(2-methylbenzo[d]thiazol-6-yl)piperazin-1-yl)cyclopent-1-en-1-yl)-7',8'-dihydro-3'H-spiro[cyclopropane-1,6'-quinazolin]-4'(5'H)-one (Compound 81);

(R)-2'-(3-(4-(3-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 82);

(R)-2'-(3-(4-(4-fluoro-3-methylphenyl)piperazin-1-yl)cyclopent-1-en-1-yl)-7',8'-dihydro-3'H-spiro[cyclopropane-1,6'-quinazolin]-4'(5'H)-one (Compound 83);

(R)-2'-(3-(4-(3-fluoro-4-methylphenyl)piperazin-1-yl)cyclopent-1-en-1-yl)-7',8'-dihydro-3'H-spiro[cyclopropane-1,6'-quinazolin]-4'(5'H)-one (Compound 84);

(R)-2'-(3-(4-(m-tolyl)piperazin-1-yl)cyclopent-1-en-1-yl)-7',8'-dihydro-3'H-spiro[cyclopropane-1,6'-quinazolin]-4'(5'H)-one (Compound 85);

(R)-2'-(3-(4-(4-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 86);

(R)-N-methyl-3-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 87);

(R)-2'-(3-(4-(2-fluoro-4-methylphenyl)piperazin-1-yl)cyclopent-1-en-1-yl)-7',8'-dihydro-3'H-spiro[cyclopropane-1,6'-quinazolin]-4'(5'H)-one (Compound 88);

(R)-2-fluoro-N-methyl-4-(4-(3-(4'-oxo-4',5',7',8'-tetrahydro-3'H-spiro[cyclopropane-1,6'-quinazolin]-2'-y)cyclopent-2-en-1-yl)piperazin-1-yl)benzamide (Compound 89);

(R)-2'-(3-(4-(o-tolyl)piperazin-1-yl)cyclopent-1-en-1-yl)-7',8'-dihydro-3'H-spiro[cyclopropane-1,6'-quinazolin]-4'(5'H)-one (Compound 90);

(R)-2'-(3-(4-(thiophen-3-yl)piperazin-1-yl)cyclopent-1-en-1-yl)-7',8'-dihydro-3'H-spiro[cyclopropane-1,6'-quinazolin]-4'(5'H)-one (Compound 91);

(R)-2'-(3-(4-(2-chloro-4-methylphenyl)piperazin-1-yl)cyclopent-1-en-1-yl)-7',8'-dihydro-3'H-spiro[cyclopropane-1,6'-quinazolin]-4'(5'H)-one (Compound 92);

(R)-2'-(3-(4-(2-chloro-3-fluorophenyl)piperazin-1-yl)cyclopent-1-en-1-yl)-7',8'-dihydro-3'H-spiro[cyclopropane-1,6'-quinazolin]-4'(5'H)-one (Compound 93);

(R)-2-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 94);

(R)-2'-(3-(4-(4-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 95);

(R)-2'-(3-(4-(4-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 96);

(R)-N,3-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 97);

(R)-N,2-dimethyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 98);

(R)-2'-(3-(4-(3-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 99);

(R)-2'-(3-(4-(2,3-difluorophenyl)piperazin-1-yl)cyclopent-1-en-1-yl)-7',8'-dihydro-3'H-spiro[cyclopropane-1,6'-quinazolin]-4'(5'H)-one (Compound 100);

(R)-2'-(3-(4-(thiazol-2-yl)piperazin-1-yl)cyclopent-1-en-1-yl)-7',8'-dihydro-3'H-spiro[cyclopropane-1,6'-quinazolin]-4'(5'H)-one (Compound 101);

(R)-2'-(3-(4-(4-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 102);

(R)-5-chloro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 103);

(R)-N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-5-carboxamide (Compound 104);

(R)-N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)thiazole-4-carboxamide (Compound 105);

(R)-2'-(3-(4-(2,5-difluorophenyl)piperazin-1-yl)cyclopent-1-en-1-yl)-7',8'-dihydro-3'H-spiro[cyclopropane-1,6'-quinazolin]-4'(5'H)-one (Compound 106);

(R)-2'-(3-(4-(3,5-dichloropyridin-2-yl)piperazin-1-yl)cyclopent-1-en-1-yl)-7',8'-dihydro-3'H-spiro[cyclopropane-1,6'-quinazolin]-4'(5'H)-one (Compound 107);

(R)-2'-(3-(4-(3-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 108);

(R)-2'-(3-(4-(3,5-difluorophenyl)piperazin-1-yl)cyclopent-1-en-1-yl)-7',8'-dihydro-3'H-spiro[cyclopropane-1,6'-quinazolin]-4'(5'H)-one (Compound 109);

(R)-2'-(3-(4-(2,6-difluorophenyl)piperazin-1-yl)cyclopent-1-en-1-yl)-7',8'-dihydro-3'H-spiro[cyclopropane-1,6'-quinazolin]-4'(5'H)-one (Compound 110);

(R)-3-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzonitrile (Compound 111);

(R)-5-fluoro-N-methyl-6-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 112);

(R)-2'-(3-(4-(5-methylthiazol-2-yl)piperazin-1-yl)cyclopent-1-en-1-yl)-7',8'-dihydro-3'H-spiro[cyclopropane-1,6'-quinazolin]-4'(5'H)-one (Compound 113);

(R)-2'-(3-(4-(4-fluoro-3-methoxyphenyl)piperazin-1-yl)cyclopent-1-en-1-yl)-7',8'-dihydro-3'H-spiro[cyclopropane-1,6'-quinazolin]-4'(5'H)-one (Compound 114);

(R)-2'-(3-(4-(3-chloro-5-fluorophenyl)piperazin-1-yl)cyclopent-1-en-1-yl)-7',8'-dihydro-3'H-spiro[cyclopropane-1,6'-quinazolin]-4'(5'H)-one (Compound 115);

(R)-2'-(3-(4-(2-fluorophenyl)piperazin-1-yl)cyclopent-1-en-1-yl)-7',8'-dihydro-3'H-spiro[cyclopropane-1,6'-quinazolin]-4'(5'H)-one (Compound 116);

(R)-2'-(3-(4-phenylpiperazin-1-yl)cyclopent-1-en-1-yl)-7',8'-dihydro-3'H-spiro[cyclopropane-1,6'-quinazolin]-4'(5'H)-one (Compound 117);

2'-((1R,3 S)-3-(4-(4-chlorophenyl)piperazin-1-yl)cyclopentyl)-7',8'-dihydro-3'H-spiro[cyclopropane-1,6'-quinazolin]-4'(5'H)-one (Compound 118);

2'-((1 S ,3S)-3-(4-(4-chlorophenyl)piperazin-1-yl)cyclopentyl)-7',8'-dihydro-3'H-spiro[cyclopropane-1,6'-quinazolin]-4'(5'H)-one (Compound 119);

2'-((1S ,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 120);

2'-((1R,3R)-3-(4-(4-chlorophenyl)piperazin-1-yl)cyclopentyl)-7',8'-dihydro-3'H-spiro[cyclopropane-1,6'-quinazolin]-4'(5'H)-one (Compound 121);

(R)-2'-(3-(4-(2-chlorophenyl)piperazin-1-yl)cyclopent-1-en-1-yl)-7',8'-dihydro-3'H-spiro[cyclopropane-1,6'-quinazolin]-4'(5'H)-one (Compound 122);

(R)-2'-(3-(4-(5-fluoro-2-methylphenyl)piperazin-1-yl)cyclopent-1-en-1-yl)-7',8'-dihydro-3'H-spiro[cyclopropane-1,6'-quinazolin]-4'(5'H)-one (Compound 123);

(R)-2'-(3-(4-(5-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 124);

(R)-2'-(3-(4-(4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 125);

(R)-2'-(3-(4-(3-fluoro-5-methylphenyl)piperazin-1-yl)cyclopent-1-en-1-yl)-7',8'-dihydro-3'H-spiro[cyclopropane-1,6'-quinazolin]-4'(5'H)-one (Compound 126);

(R)-2-fluoro-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzonitrile (Compound 127);

(R)-2'-(3-(4-(pyrimidin-2-yl)piperazin-1yl)cyclopent-1-en-1-yl)-7',8'-dihydro-3'H-spiro[cyclopropane-1,6'-quinazolin]-4'(5'H)-one (Compound 128);

(R)-2'-(3-(4-(2-methylpyridin-3-yl)piperazin-1-yl)cyclopent-1-en-1-yl)-7',8'-dihydro-3'H-spiro[cyclopropane-1,6'-quinazolin]-4'(5'H)-one (Compound 129);

(R)-N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)isonicotinamide (Compound 130);

(R)-N-methyl-2-(4-(3-(4'-oxo-4',5',7',8'-tetrahydro-3'H-spiro[cyclopropane-1,6'-quinazolin]-2'-yl)cyclopent-2-en-1-yl)piperazin-1-yl)nicotinamide (Compound 131);

(R)-2'-(3-(4-(3-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 132);

(R)-2'-(3-(4-(4-fluoro-2-methoxyphenyl)piperazin-1-yl)cyclopent-1-en-1-yl)-7',8'-dihydro-3'H-spiro[cyclopropane-1,6'-quinazolin]-4'1(5'H)-one (Compound 133);

(R)-3-chloro-N-methyl-4-(4-(3-(4'-oxo-4',5',7',8'-tetrahydro-3'H-spiro[cyclopropane-1,6'-quinazolin]-2'-yl)cyclopent-2-en-1-yl)piperazin-1-yl)benzamide (Compound 134);

(R)-2'-(3-(4-(5-ethylpyrimidin-2-yl)piperazin-1-yl)cyclopent-1-en-1-yl)-7',8'-dihydro-3'H-spiro[cyclopropane-1,6'-quinazolin]-4'(5'H)-one (Compound 135);

(R)-2'-(3-(4-(3,4-dimethylphenyl)piperazin-1-yl)cyclopent-1-en-1-yl)-7',8'-dihydro-3'H-spiro[cyclopropane-1,6'-quinazolin]-4'(5'H)-one (Compound 136);

(R)-2'-(3-(4-(5-fluoro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 137);

(R)-2'-(3-(4-(5-chloro-2-fluorophenyl)piperazin-1-yl)cyclopent-1-en-1-yl)-7',8'-dihydro-3'H-spiro[cyclopropane-1,6'-quinazolin]-4'(5'H)-one (Compound 138);

(R)-2'-(3-(4-(2-chloro-6-fluorophenyl)piperazin-1-yl)cyclopent-1-en-1-yl)-7',8'-dihydro-3'H-spiro[cyclopropane-1,6'-quinazolin]-4'(5'H)-one (Compound 139);

(R)-2'-(3-(4-(2,3-dimethylphenyl)piperazin-1-yl)cyclopent-1-en-1-yl)-7',8'-dihydro-3'H-spiro[cyclopropane-1,6'-quinazolin]-4'(5'H)-one (Compound 140);

(R)-2'-(3-(4-(5-chloro-4-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 141);

(R)-2'-(3-(4-(5-fluoropyridin-3-yl)piperazin-1-yl)cyclopent-1-en-1-yl)-7',8'-dihydro-3'H-spiro[cyclopropane-1,6'-quinazolin]-4'(5'H)-one (Compound 142);

(R)-2'-(3-(4-(3-chloro-2-methylphenyl)piperazin-1-yl)cyclopent-1-en-1-yl)-7',8'-dihydro-3'H-spiro[cyclopropane-1,6'-quinazolin]-4'(5'H)-one (Compound 143);

(R)-2'-(3-(4-(2,5-dimethylphenyl)piperazin-1-yl)cyclopent-1-en-1-yl)-7',8'-dihydro-3'H-spiro[cyclopropane-1,6'-quinazolin]-4'(5'H)-one (Compound 144);

(R)-2'-(3-(4-(6-methylpyridin-2-yl)piperazin-1-yl)cyclopent-1-en-1-yl)-7',8'-dihydro-3'H-spiro[cyclopropane-1,6'-quinazolin]-4'(5'H)-one (Compound 145);

(R)-2'-(3-(4-(5-chloro-3-fluoropyridin-2-yl)piperazin-1-yl)cyclopent-1-en-1-yl)-7',8'-dihydro-3'H-spiro[cyclopropane-1,6'-quinazolin]-4'(5'H)-one (Compound 146);

(R)-2'-(3-(4-(2-methylpyridin-4-yl)piperazin-1-yl)cyclopent-1-en-1-yl)-7',8'-dihydro-3'H-spiro[cyclopropane-1,6'-quinazolin]-4'(5'H)-one (Compound 147);

(R)-2'-(3-(4-(4-(thiophen-3-yl)phenyl)piperazin-1-yl)cyclopent-1-en-1-yl)-7',8'-dihydro-3'H-spiro[cyclopropane-1,6'-quinazolin]-4'(5'H)-one (Compound 148);

2'-((1S,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 149);

2'-((1R,3S)-3-(4-(4-fluorophenyl)piperazin-1-yl)cyclopentyl)-7',8'-dihydro-3'H-spiro[cyclopropane-1,6'-quinazolin]-4'(5'H)-one (Compound 150);

2'-((1S,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 151);

2'-((1R,3R)-3-(4-(4-fluorophenyl)piperazin-1-yl)cyclopentyl)-7',8'-dihydro-3'H-spiro[cyclopropane-1,6'-quinazolin]-4'(5'H)-one (Compound 152);

2'-((1R,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 153);

2'-((1S,3S)-3-(4-(3-fluorophenyl)piperazin-1-yl)cyclopentyl)-7',8'-dihydro-3'H-spiro[cyclopropane-1,6'-quinazolin]-4'(5'H)-one (Compound 154);

2'-((1S,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 155);

2'-((1R,3R)-3-(4-(3-fluorophenyl)piperazin-1-yl)cyclopentyl)-7',8'-dihydro-3'H-spiro[cyclopropane-1,6'-quinazolin]-4'(5'H)-one (Compound 156);

(R)-2'-(3-(4-(6-phenylpyridin-3-yl)piperazin-1-yl)cyclopent-1-en-1-yl)-7',8'-dihydro-3'H-spiro[cyclopropane-1,6'-quinazolin]-4'(5'H)-one (Compound 157);

(R)-2'-(3-(4-([1,1'-biphenyl]-4-yl)piperazin-1-yl)cyclopent-1-en-1-yl)-7',8'-dihydro-3'H-spiro[cyclopropane-1,6'-quinazolin]-4'(5'H)-one (Compound 158); and 2'-(3-(3-(4-chlorophenyl)-3,8-diazabicyclo [3.2.1]octan-8-yl)cyclopent-1-en-1-yl)-7',8'-dihydro-3'H-spiro[cyclopropane-1,6'-quinazolin]-4'(5'H)-one (Compound 159).

9. A pharmaceutical composition comprising the compound of claim 1, its tautomeric form, its stereoisomer, or its pharmaceutically acceptable salt, and a pharmaceutically acceptable carrier.

10. The pharmaceutical composition of claim 9, further comprising at least one known anticancer agent, or a pharmaceutically acceptable salt of said agent.

11. The pharmaceutical composition of claim 9, further comprising at least one compound selected from busulfan, melphalan, chlorambucil, cyclophosphamide, ifosfamide, temozolomide, bendamustine, cisplatin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

12. A pharmaceutical composition comprising the compound of claim 2, its tautomeric form, its stereoisomer, or its pharmaceutically acceptable salt, and a pharmaceutically acceptable carrier.

13. A pharmaceutical composition comprising the compound of claim 8, its tautomeric form, its stereoisomer, or its pharmaceutically acceptable salt, and a pharmaceutically acceptable carrier.

14. A method of treating a cancer comprising administering to the mammal in need of such treatment a therapeutically effective amount of a compound, its tautomeric form, its stereoisomer, or its pharmaceutically acceptable sat, of claim 1 wherein the cancer is selected from liver cancer, melanoma, Hodgkin's disease, non-Hodgkin's lymphomas, acute or chronic lymphocytic leukaemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukaemia, primary brain carcinoma, small-cell king carcinoma, stomach carcinoma, colon carcinoma, malignant pancreatic insulinoma, malignant carcinoid carcinoma, malignant melanoma, chorio carcinoma, mycosis fungoide, head or neck carcinoma, osteogenic sarcoma, pancreatic carcinoma, acute granulocytic leukaemia, hairy cell leukaemia, neuroblastoma, rhabdomyosarcoma, Kaposi's sarcoma, genitourinary carcinoma, thyroid carcinoma, esophageal carcinoma, malignant hypercalcemia, cervca hyperplasia, renal cell carcinoma, endometrial carcinoma, polycythemia vera, essential thrombocytosis, adrenal cortex carcinoma, skin cancer, or prostatic carcinoma.

15. A method of potentiating the efficacy of chemotherapeutic regimen for a patient undergoing chemotherapeutic treatment comprising co-administering to the patient an effective amount of a compound, tautomer, stereoisomer, or salt of claim 1.

16. The method of claim 15, wherein the compound, tautomer, stereoisomer, or salt is co-administered simultaneously, sequentially, or cyclically with the anticancer agent.

17. The method of claim 16, wherein the anticancer agent is selected from busulfan, melphalan, chlorambucil, cyclophosphamide, ifosfamide, temozolomide, bendamustine, cisplatin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, panitumumab, ofatumumab, bevacizumab, trastuzumab, adalimumab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

18. A method for sensitizing a patient who has developed or is likely to develop resistance for chemotherapic agents comprising administering an effective amount of a compound, its tautomeric form, its stereoisomer, or its pharmaceutically acceptable salt, of claim 1.

19. A method of treating a cancer comprising administering to the mammal in need of such treatment a therapeutically effective amount of a compound, its tautomeric form, its stereoisorner, or its pharmaceutically acceptable salt, of claim 8 wherein the cancer is selected from liver cancer, melanoma, Hodgkin's disease, non-Hodgkin's lymphomas, acute or chronic lymphocytic leukaemia, multiple myeloma, neuroblastorna, breast carcinoma, ovarian carcinoma, lung carcinoma, Wilms' tumor, cervical carcinoma, testicular carcinoma, soft-tissue sarcoma, primary macroalobulinemia, bladder carcinoma, chronic granulocytic leukaemia, primary brain carcinoma, small-cell king carcinoma, stomach carcinoma, colon carcinoma, malignant pancreatic insulinoma, malignant carcinoid carcinoma, malignant melanoma, chorio carcinoma, mycosis fungoide, head or neck carcinoma, osteogenic sarcoma, pancreatic carcinoma, acute granulocytic leukaemia, hairy cell leukaemia, neuroblastoma, rhabdomyosarcoma. Kaposi's sarcoma, genitourinary carcinoma, thyroid carcinoma, esophageal carcinoma, malignant hypercalcemia, cervca hyperplasia, renal cell carcinoma, endometrial carcinoma, polycythemia vera, essential thrombocytosis, adrenal cortex carcinoma, skin cancer, or prostatic carcinoma.

* * * * *